United States Patent [19]

Ivanov et al.

[11] Patent Number: 5,661,954
[45] Date of Patent: Sep. 2, 1997

[54] NEEDLE FEED WHEEL AND NEEDLE TRANSFER MECHANISM

[75] Inventors: Konstantin Ivanov, Bound Brook; James Lotze, Skillman; Donald Pompei, Montville, all of N.J.; Manfred Reiser, Winenden-Hertmannsweiler, Germany; Jost Mucheyer; Erwin Bauder, both of Waiblingen, Germany

[73] Assignees: Ethicon, Inc., Somerville, N.J.; Harro Hofliger Verpackungsmaschinen GmbH

[21] Appl. No.: 523,521

[22] Filed: Aug. 31, 1995

[51] Int. Cl.⁶ .................................................. B65B 63/04
[52] U.S. Cl. .................. 53/430; 53/116; 53/118; 53/250; 53/281; 53/457; 53/468; 53/564
[58] Field of Search ............... 53/116, 118, 238, 53/249, 250, 281, 282, 287, 430, 457, 468, 471, 474, 564; 206/63.3

[56] References Cited

U.S. PATENT DOCUMENTS

| | | | |
|---|---|---|---|
| 5,213,210 | 5/1993 | Cascio et al. | 206/380 |
| 5,230,424 | 7/1993 | Alpern et al. | 206/63.3 |
| 5,469,689 | 11/1995 | Demarest et al. | 53/430 |
| 5,473,810 | 12/1995 | Demarest et al. | 53/118 X |
| 5,473,854 | 12/1995 | Demarest et al. | 53/116 |
| 5,477,609 | 12/1995 | Demarest et al. | 53/118 X |
| 5,487,212 | 1/1996 | Demarest et al. | 53/118 X |
| 5,487,216 | 1/1996 | Demarest et al. | 53/118 X |
| 5,491,954 | 2/1996 | Sobel | 53/116 |

*Primary Examiner*—Daniel Moon

[57] ABSTRACT

The specification discloses an automated apparatus and method for packaging surgical needles having sutures attached thereto wherein a bundle of needles and sutures are placed at a semi-automated separation station and an operator feeds the needles, one at a time, into a rotating needle feed wheel. As the feed wheel advances, the suture is tensioned and directed along a pre-determined path to separate it from the remaining sutures in the bundle. The apparatus has a plurality of individually rotatable tool nests which are sequentially spaced on a rotating or indexing turntable. These tool nests sequentially receive plastic packages for receiving the needle and suture at a first station. At a second station, a needle is inserted into the package by robotic fingers which have retrieved the needle and attached suture from the rotating needle feed wheel. The rotating needle feed wheel and the rotating tool nests are synchronized to step together as each advances. At a third station, the package and needle are rotated to tension the suture and position the package and the suture for automatic winding of the suture into the package. At a fourth station, the rotatable tool nest is rapidly rotated to wind the suture into a circumferential channel in the package which surrounds the needle.

45 Claims, 65 Drawing Sheets

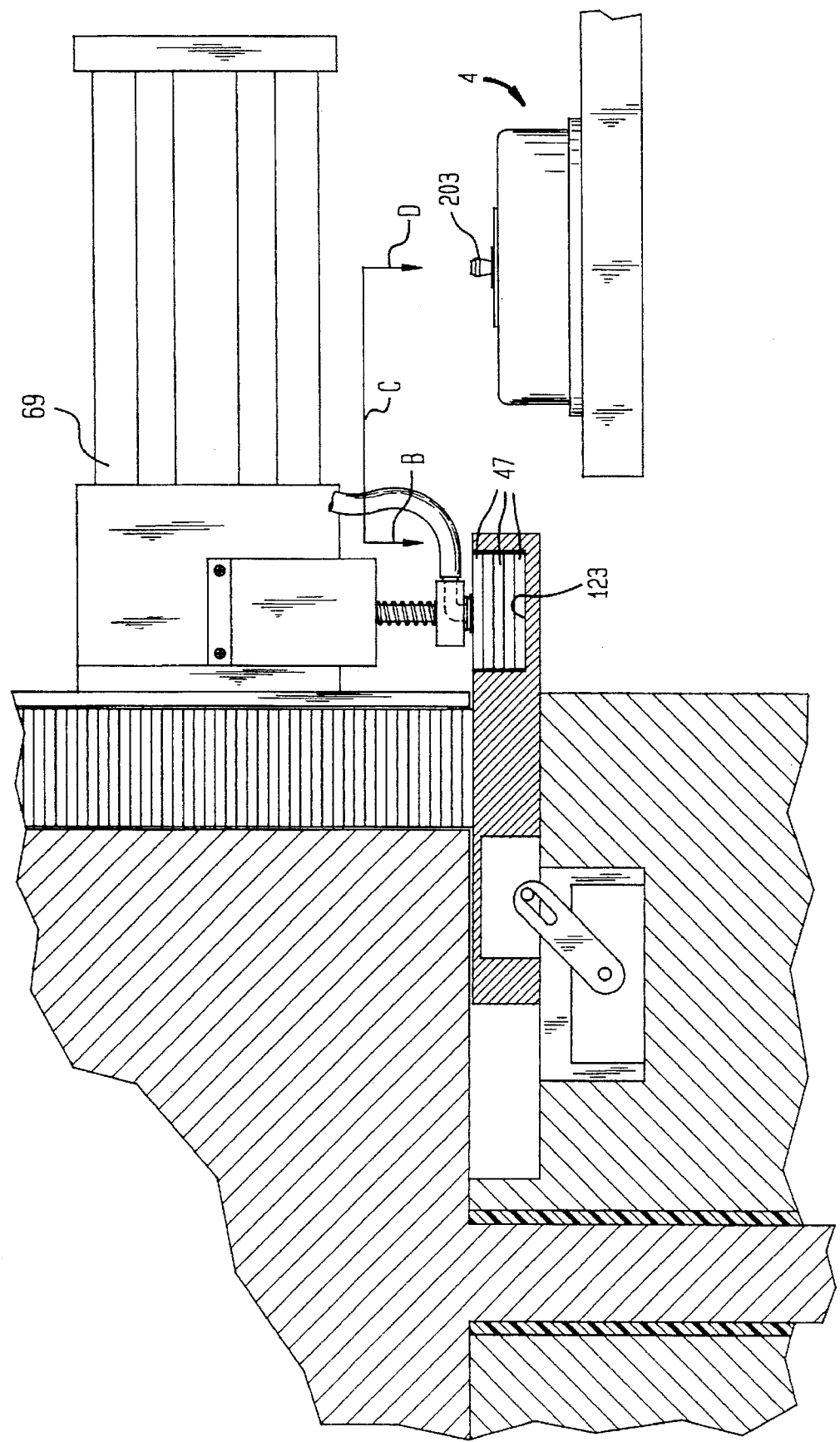

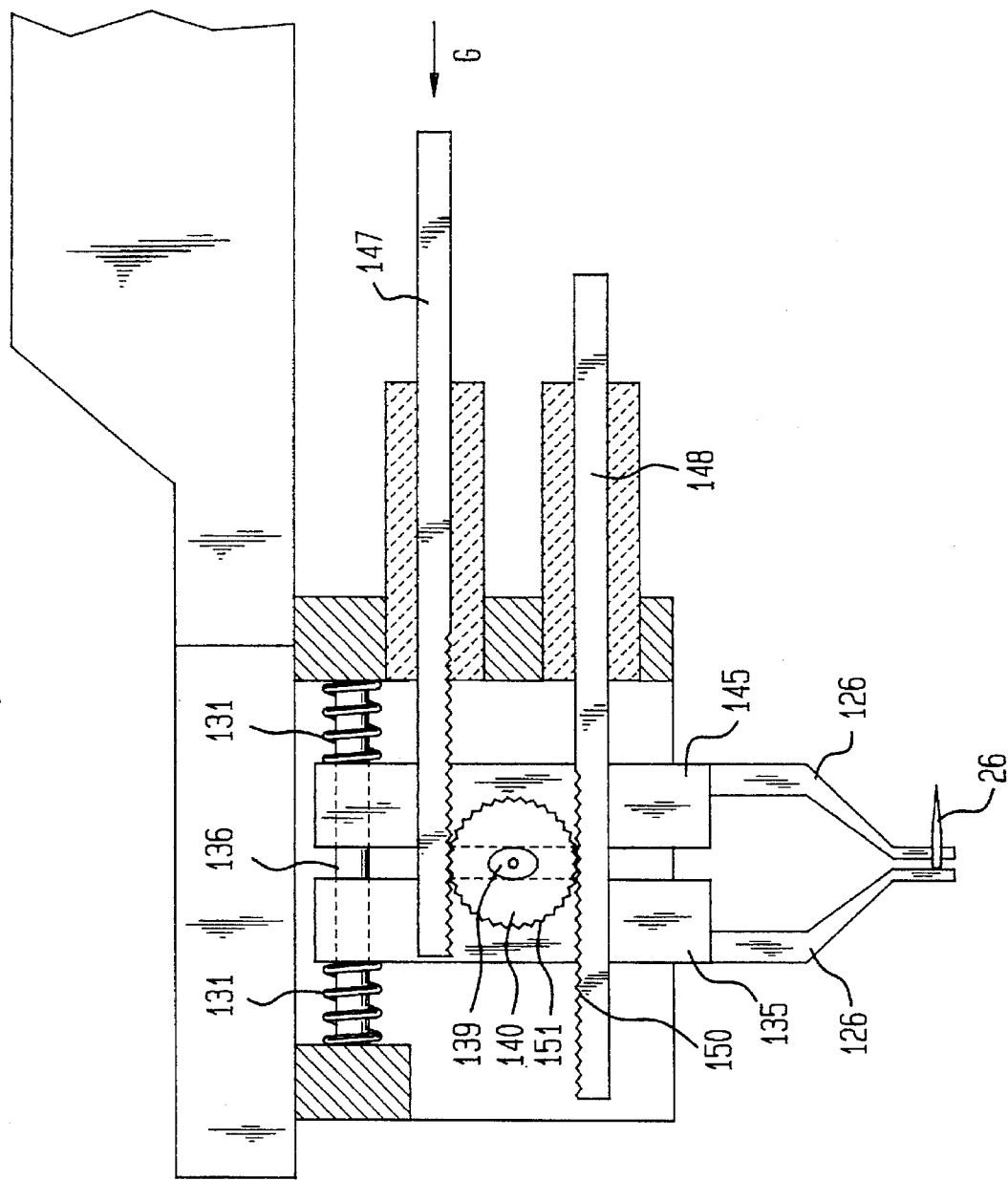

FIG. 37
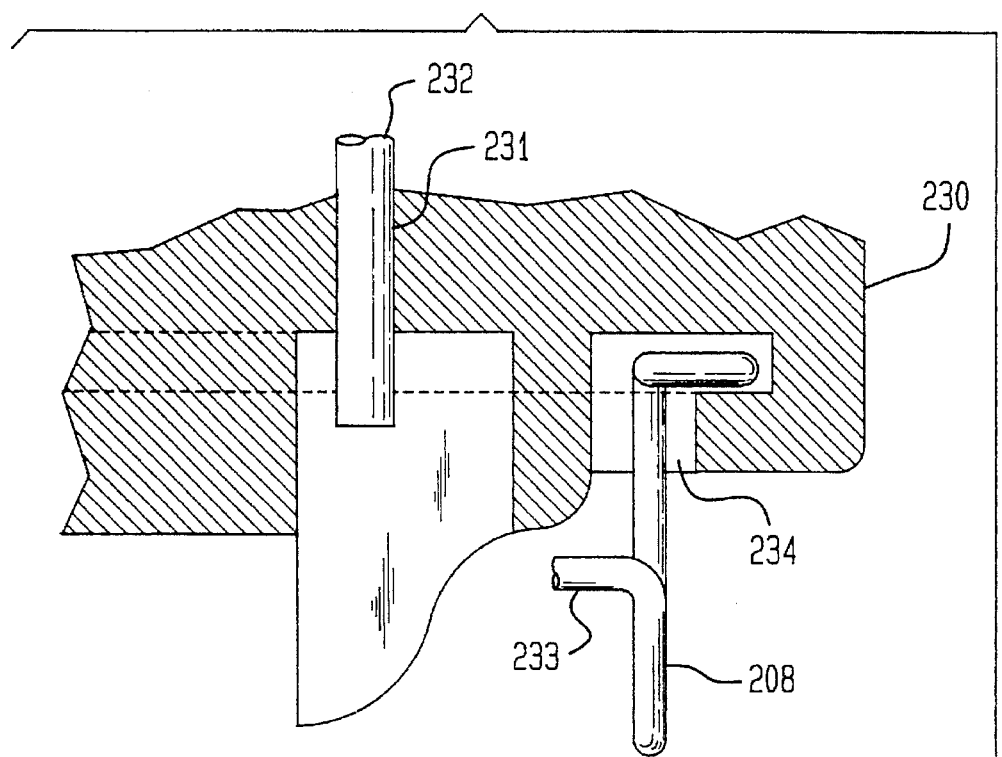
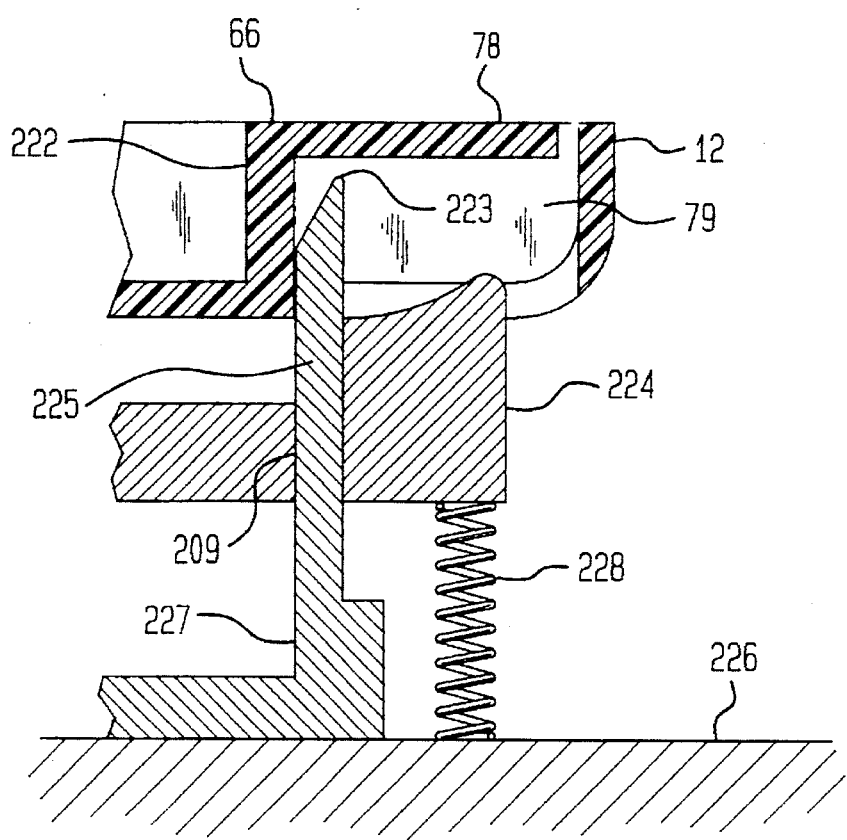

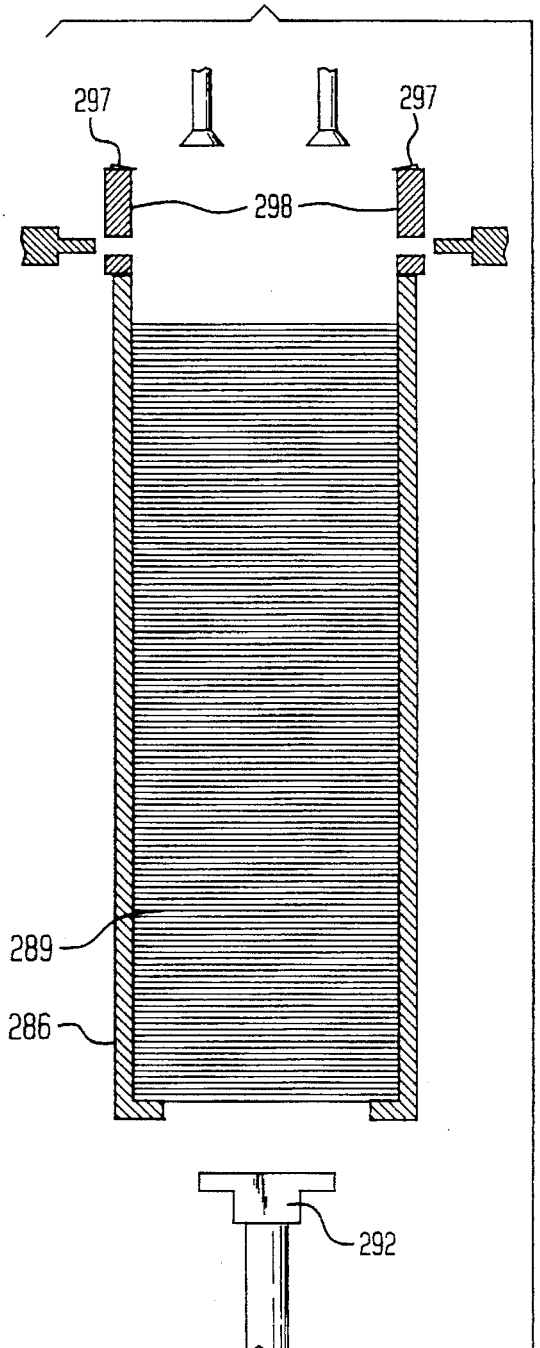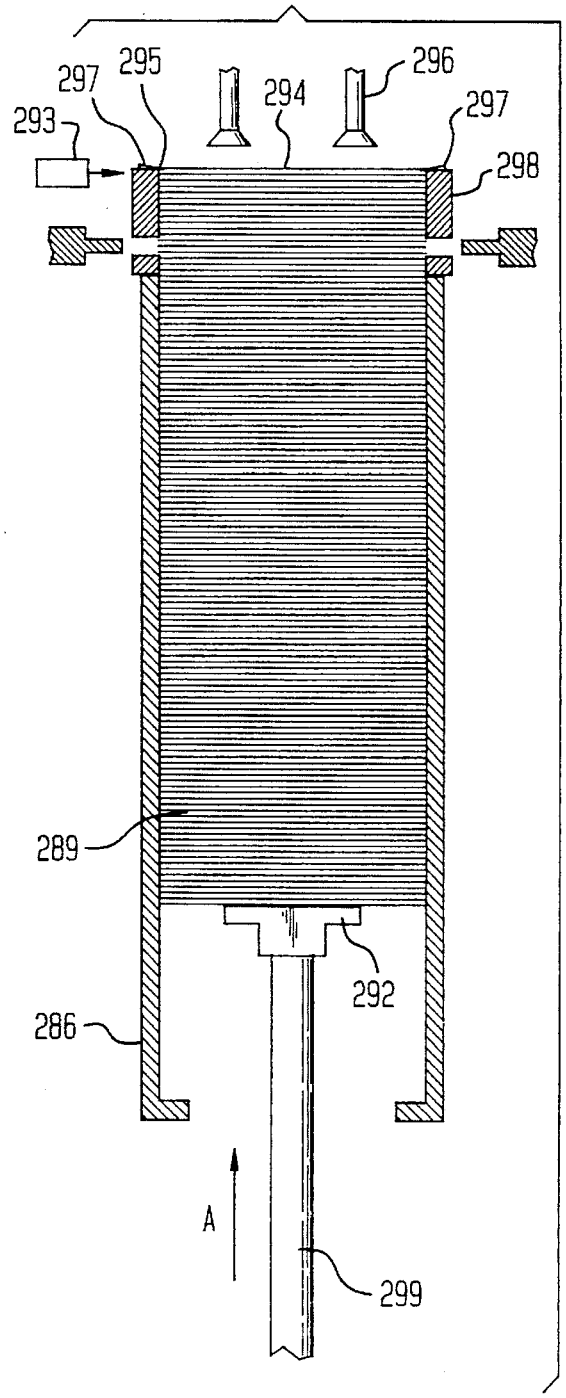

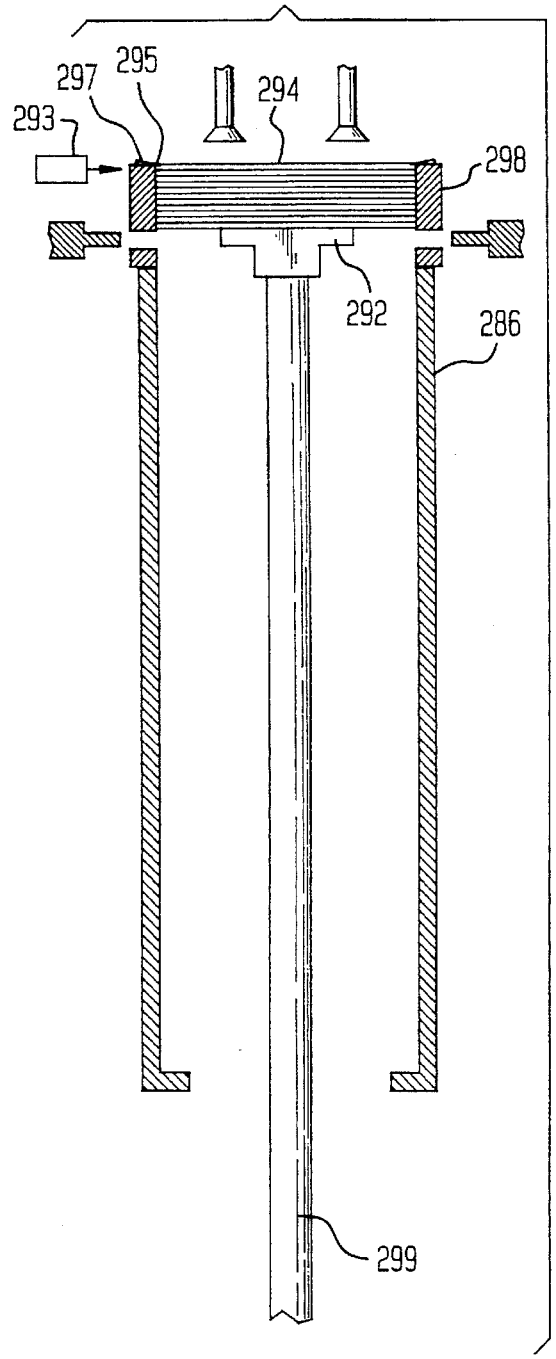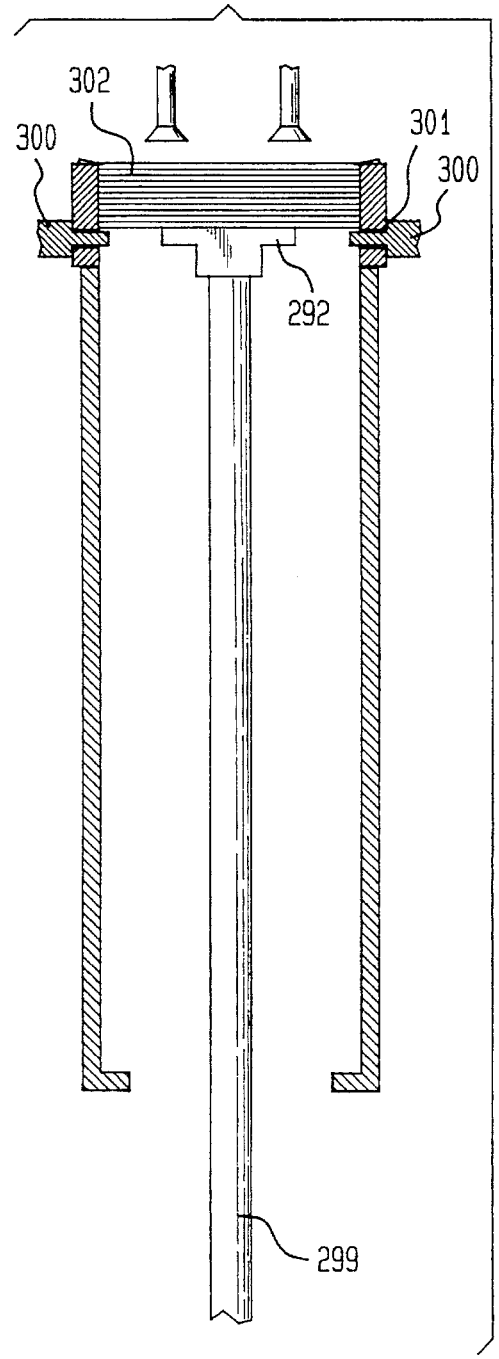

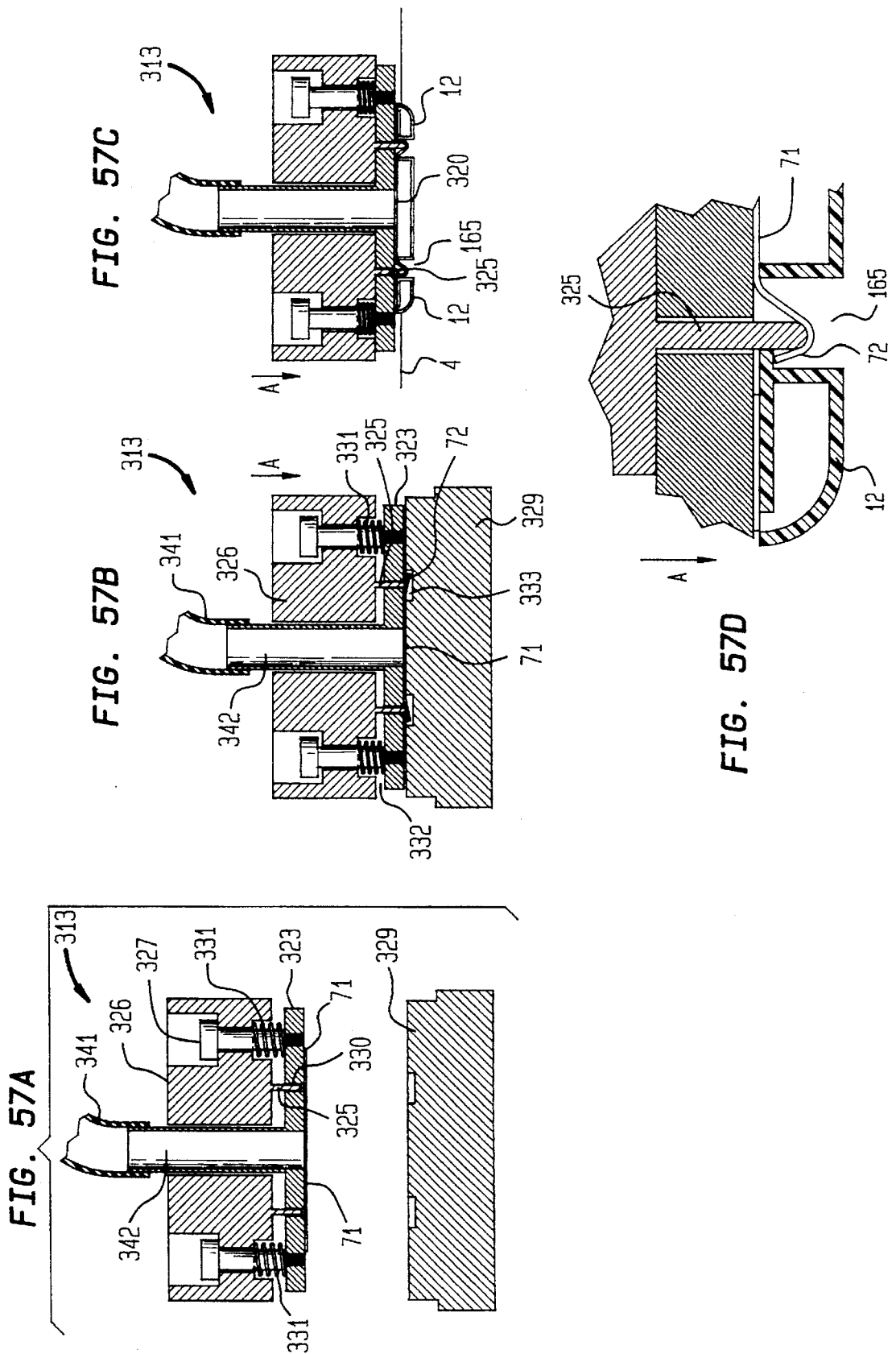

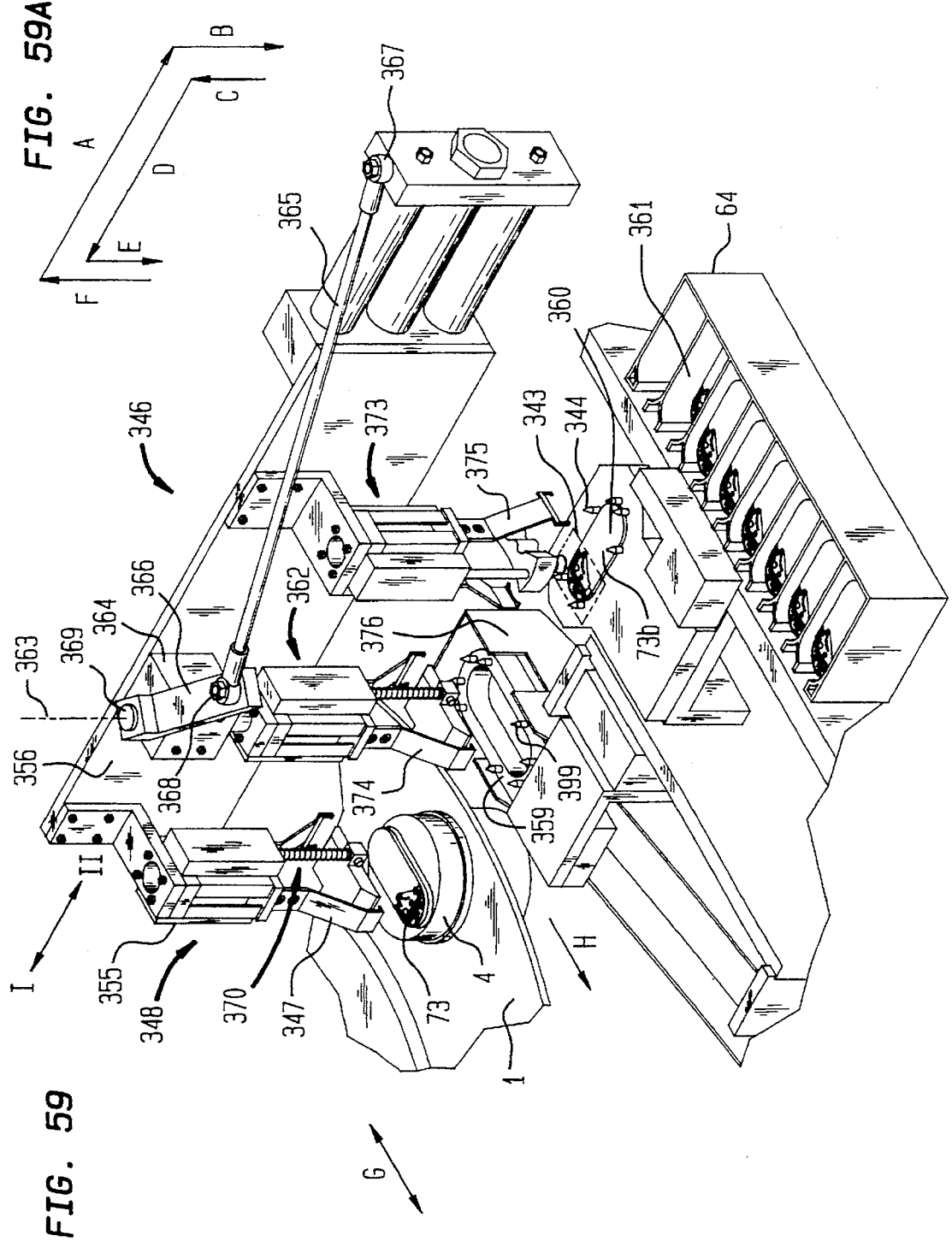

NEEDLE FEED WHEEL AND NEEDLE TRANSFER MECHANISM

FIELD OF THE INVENTION

The present invention relates to a method and machine for singulating and feeding surgical needles having sutures attached thereto and, more particularly, to a mechanism for feeding an automated machine for the high-speed packaging of surgical needles, each with an attached suture, into a tray with a detachable cover structure wherein the suture is wound into an annular channel around the exterior of the package.

BACKGROUND OF THE INVENTION

Currently, in the medical, surgical and health-related technology, a need has developed for the high-speed and efficient packaging of sutures attached to a surgical needle. This includes sutures swaged or similarly fastened thereto, in which such combined needle and suture is generally referred to as armed suture. This need has become increasingly important as the cost of sterile packaging for the armed suture approaches the cost of the armed suture itself.

Further, the rising demand of users for such combined surgical needles and attached sutures, and various diverse types of inexpensively manufactured suture packages for the containment of needles and attached sutures has created a need for the automatic packaging of armed sutures.

DISCUSSION OF THE PRIOR ART

The prior art discloses suture packages having a covered tray-shaped container designed to receive and fixedly retain therein a one or more needles and therewith attached sutures, in which the suture package, upon opening the cover, enables the reliable and simple withdrawal of the needle and its attached suture in a smooth and unobstructed manner.

When it is desired to remove the needle from the suture package, the needle is engaged by a surgeon or health professional, for example, by being gripped with a forceps and then pulled out of the suture tray. It is essential that the needle easily disengage from its restraint in the package, and that the suture attached to the needle be readily able to slip out of the tray without any binding or snagging.

Thus, in one prior art needle and suture package construction which, for example, includes an injection-molded plastic tray, the needles are generally engaged by a clamping structure located in the tray so as to be "parked" or retained in a central region of the tray. The suture extending from the needle to which it is attached, is then conducted into and deposited in a peripheral channel formed about the suture tray so as to extend along the peripheral length of the channel. This positioning of the needle, and particularly that of the suture within the peripheral channel of the tray is intended to eliminate tight bends or curves normally imposed on the sutures so as to facilitate their easy individual withdrawal from the suture package while eliminating any potential entanglement with the remaining turns of the suture or snagging on the structure of the tray or package.

Such a suture package is disclosed in U.S. Pat. No. 5,213,210 entitled "Easy Loading Suture Package", which is assigned to the assignee of the present application, which also includes therein, reference to several prior art armed suture packages, including U.S. Pat. No. 4,967,902 to Kalinski et al.

In the specific design of the flat tray-shaped plastic container having a peripheral channel as disclosed in the above-mentioned patent, the suture package is basically constituted of an oval and flat-bottomed injection-molded plastic tray having a flat central surface area including a raised needle clamping structure formed thereon for engaging and "parking" a needle in a predetermined position with respect to the perimeter of the package. A suture extends from the end of the needle into a channel extending about the perimeter or periphery of the suture tray and is placed into the channel so as to be essentially wound within the circumferential confines of the suture tray. The suture is positioned within the suture tray channel, so as to be protected against inadvertent outward displacement therefrom, by the presence of a multiplicity of contiguously positioned resilient fingers which are integrally molded with the suture tray, and which project outwardly above and below the confines of the channel along the length of the channel and, collectively, form a so-called "zipper structure" in which the inherently resilient nature of the fingers facilitates their temporary raising up to enable the introduction of the sutures into the suture tray channel by means of a suitable suture winding apparatus. As disclosed in U.S. Pat. No. 5,213,210, it was contemplated that the suture would be wound into the channel by successively raising the free end of each finger just before the suture is placed into position, and then allowing the free end of the needle to spring back into place to retain the suture.

A generally semi-automated winder machine has been developed for packaging surgical needles and attached sutures in a tray-like suture package, which is the subject matter of a copending patent application U.S. Ser. No. 181,591 entitled "Suture Winder Machine", commonly assigned to the assignee of the present application, and wherein at least some of the previously contemplated steps of successively raising individual fingers for placement of the suture has been semi-automated in order to be able to increase the output of needle and suture-containing packages while simultaneously reducing the number of manual procedures in effectuating the packaging of those particular items.

To that effect, the semi-automated winder machine, although necessitating the manual orientation of the trays for implementing the filling thereof with needles and attached sutures, includes a winding station which will to a considerable degree automate the winding process for the sutures so as to place the latter into a peripheral channel extending about the circumference of the tray. Also provided is a further therewith operatively associated device which will enable covers manually placed on the needle and suture-filled trays to be fastened thereto by means of a pressing die forming latchingly engaging interconnections between each of the covers and the trays, while concurrently producing from a portion of the cover a product-identifying label which remains permanently attached to the tray upon subsequent detachment of the cover. Although providing a considerable advance over the current state-of-the-art in the packaging of needles and sutures, the semi-automated winder machine as discussed hereinabove nevertheless necessitates the implementation of a considerable number of manual and labor-intensive handling steps in effectuating the filling of the trays with surgical needles and attached sutures, attaching the cover and, generally, producing complete suture packages.

Further, it has been found, that with low cost inexpensive plastic package trays, the winding of longer sutures requires several revolutions of the suture package, and several flexures of the plastic finger before the suture is completely wound. The number of flexures results in elastic deformation of the finger to the point that there is occasional permanent deformation or failure of individual fingers, which requires manual intervention to rectify.

SUMMARY OF THE INVENTION

Accordingly, the present invention, in a significant manner, improves upon the foregoing semi-automated needle and suture package-forming concept through the provision of a novel and unique substantially fully automated packaging machine adapted to, in a highly efficient and extremely rapid mode, continually fill successive trays of the type described hereinabove with an armed surgical needle having an attached suture, and subsequently cause the suture to be wound into the confines of the tray, such as into a peripheral suture channel extending about the tray. Thereafter, the packaging machine is designed to implement the automated positioning and fastening of covers to the needle and suture-filled trays to produce completed suture packages of the type described hereinabove, which are adapted to be transported to a suitable locale for either further processing, such as sterilizing, and/or overwrapping, as is required by this technology.

It is an object of the invention to provide an automated packaging machine for needles having sutures attached thereto which packages the needle in a package tray having a suture channel nominally closed by a plurality of resilient fingers, with the suture being wound into the suture channel. In the automatic machine, the package is indexed through a plurality of sequential automated workstations, which include a first workstations for mounting empty package trays on a plurality of rotatable support surfaces and a first means for advancing each of the rotatable support surfaces in an indexed manner through a plurality of sequential workstations. A second workstation receives a needle and attached suture, and inserts the needle and attached suture into the package tray in a predetermined orientation with a free end of the attached suture depending outwardly from said package tray. A second means imparts axial tension to said suture, while a third workstation opens the suture channel and imparts rotational movement to the rotatable support surface about an axis extending normal to the plane of said support surface to wind the free end of the suture into the suture channel. A fourth workstation for applies a cover to the package tray to form a suture package containing a needle and attached wound suture, with the fourth workstation imparting pressure to the cover to form a latching structure from the cover to fasten the cover to the package tray. Finally, a fifth workstation removes the suture package from the rotatable support surface for sterilization and secondary packaging. Optional inspection workstations and prewind stations may also be provided to insure that only correctly packaged needles and sutures are sent to secondary packaging.

In order to attain the foregoing essentially automated packaging of a surgical needle with an attached suture, the automated packaging machine pursuant to the invention contemplates the provision of a rotary turntable having a plurality of rotatable suture tray support surfaces circumferentially spaced so as to be distributed about the periphery thereof. The rotary turntable is rotated to cause the rotary support surfaces supporting the trays to be indexed forwardly so as to advance among the plurality of successive workstations which are adapted to, respectively, feed a package tray to the next rotatable support surface on the turntable, park an armed suture in the tray, rotate the package a half-wind and tension the suture, inspect the package to insure that an armed suture is present, wind the suture into the confines of each suture channel defined by the package tray, to attach a cover and form a latching structure between the cover and the tray and thereafter, to convey each completed suture package to suitable magazine or collection tray for further processing, sterilization, overwrapping or other disposition thereof.

A magazine feed device is mounted for synchrones feed with the indexing rotation of the rotary turntable. The magazine feed device is adapted to supply and automatically mount empty trays of the type described hereinabove on successive rotatable support surfaces. Thereafter, each tray is successively indexed forwardly by the rotating turntable to a workstation which will includes a pair of needle grippers to successively insert and position surgical needles with attached sutures into the successive trays for latching engagement with needle-clamping structure formed in the tray so as to fasten the needles therein with the sutures depending downwardly therefrom outwardly of the tray. The suture is gathered by a vacuum plenum to impart tension to the suture as the rotary turntable advances the rotatable support surface and supported package tray. As the needle and suture-filled tray is indexed forwardly, the suture is tensioned and gripped, under tension by a traveling tension member which will impart a continual drag when the suture is wound. The rotatable support surface and package tray is then rotated 180° to position the needle and suture for winding. At this station, the package is visually inspected by a vision system to verify the presence of a needle and suture in the package, and the correct position of the needle in the package. At the next workstation, the suture package is clamped by upper and lower cams to displace, simultaneously, all of the upper fingers upward with respect the tray, to enable the rotation of the rotary support surface and package tray to wind the suture into a suture channel formed in the cams by rotation of the rotary support member about a central axis perpendicular to the tray plane. As the upper and lower cams separate, a positive displacement mechanism insures that the upper fingers are returned to their original position to close the sutures within the channel.

Thereafter, the rotary support surface, mounting the tray with a needle parked therein, with the attached suture having been wound into the peripheral channel of the tray, is indexed forwardly to a further workstation at which an operating mechanism applies a cover onto the tray and, concurrently, a pressing die imparts pressure to the cover to form a plurality of latching structures in the cover which fasten the cover to the tray. Upon completion of this particular cover-attaching sequence, the resultingly formed complete suture package is indexed to a further workstation at which suitable grippers may engage the suture package to be conveyed to a magazine or other receiving unit to be readied for further processing, such as sterilizing, overwrapping or the like, as required.

The foregoing sequence of operative steps is continually repeated for each successive rotatable support on the rotary turntable. As one rotatable support member is receiving an empty tray, a preceding rotatable support member is undergoing the above-mentioned packaging cycle. Thus, a successive tray is always placed into a position of readiness at a preceding workstation and processed in a similar manner as before upon the following forward indexing advance of the rotary turntable. This ensures a continuous packaging cycle for successive suture packages in a highly efficient and high-speed operation without the need for any or at most only minimal manual intervention in the operation of the packaging machine.

Intermediate the various workstations as set forth hereinbefore, there may optionally be arranged other workstations adapted to enable the ascertaining of the presence of empty trays at the initial workstation, for a verification of the proper orientation of the needles inserted into the trays and for a visual inspection of the trays subsequent to the winding of the sutures into the tray channels.

Accordingly, it is a primary object of the present invention to provide a packaging machine facilitating the automated high-speed packaging of surgical needles having sutures attached thereto.

A more specific object of the present invention resides in the provision of a machine for the automated packaging of needles and attached sutures wherein the packaging is effected on a forwardly indexing rotary turntable having a plurality of circumferentially spaced tray-supporting rotatable support surfaces, and wherein empty trays positioned on the support surfaces are in succession filled with a needle and attached suture; indexed to a workstation which includes operative mechanism facilitating the winding of the sutures into a peripheral channel extending about each tray; and then indexed to a further workstation in which a cover is applied onto and fastened to the tray by a pressing die so as to form a suture package containing a needle and attached wound suture.

A more specific object of the present invention is to provide an automated machine for the packaging of surgical needles and attached sutures wherein the needles are automatically fed in succession and positioned in a predetermined position in an empty suture tray which is mounted on a rotatable support, the sutures being wound into the confines of a peripheral channel of the tray, and a cover fastened thereunto so as to form a needle and suture-containing package.

Yet another object of the present invention is to provide a machine for the automated packaging of a surgical needle and attached suture in a manner as described herein, which also incorporates workstations enabling the inspection of the trays to verify the presence of the trays and contents thereof.

The automated packaging machine also provides for a rotary turntable for the high-speed sequential loading of successive forwardly indexed trays, each with a needle and attached suture; the indexed advance of the needle and suture-filled tray to a suitable suture-winding station of the machine, the subsequent conveyance of the trays containing the needles and attached wound sutures to a cover-applying station of the machine to provide the suture packages, and the subsequent automated removal of the completed suture packages from the machine. The automated packaging machine is resultingly adapted to provide for the continuous and repetitive production of suture packages in a single high-speed production cycle without necessitating any manual manipulation thereof.

Furthermore, the present invention provides a novel semi-automated buffer for facilitating an interface between a plurality of manual needle swaging stations, or an automatic needle swag station having a different production rate cycle time. This buffer enables the manual placement of needles with attached sutures in a continuous revolving workstation that provides a precise pick-point for robotic grippers that place the needles and sutures into the package trays. The control system of the present invention enables the automated machine to skip cycles on a regular basis to compensate for variations in manual through-put, or to facilitate the merge of the automatic packaging machine of the present invention with an automated swag station having a different production rate.

The present invention also provides an automated magazine changer which enables a magazine of components to be interchanged, with the empty magazine removed, and a full magazine inserted, without slowing the production rate of the machine.

Furthermore, the present invention is also directed to the provision of a novel method for the automated packaging of multiple surgical needles and attached sutures into trays and the application of covers thereto in sequential production steps through the intermediary of the automated packaging machine.

BRIEF DESCRIPTION OF THE DRAWINGS

Reference may now be had to the following detailed description of an exemplary embodiment of a machine for the automated packaging of surgical needles and attached sutures, as described hereinabove, taken in conjunction with the accompanying drawings; in which:

FIGS. 16A through 16E illustrate in partially sectioned elevation views, the successive steps of the tray loading carrousel as it cycles through the mechanical load sequence for loading package trays on the rotatable tool nests;

FIG. 37 illustrates a schematic view of the winding tooling detail interacting with the tray suture channel and fingers in the open tool position prior to closure;

FIGS. 40A and B illustrate the needle hold plunger and suture hold down plunger as projected in the package, wherein FIG. 40A is a plan view and FIG. 40B is an elevation view;

FIGS. 48 through 52 illustrate the successive step of the operational sequence for the label magazine system;

FIG. 53A illustrates the relative motion of a portion of the label station illustrated in FIG. 53;

FIGS. 57A, B, and C, illustrates in a sequential manner the label pre-form and staking operations in sectioned elevation views;

FIG. 57D, is an enlarged detail of FIG. 57C to illustrate label staking;

FIG. 59 illustrates an isometric view of the unload mechanism at station VIII;

FIG. 59A illustrates the relative motion of a portion of the unload mechanism illustrated in FIG. 59;

DETAILED DESCRIPTION OF A PREFERRED EMBODIMENT

Description of Package for Needle with Attached Suture

FIGS. 1 through 8 illustrate the construction of the needle with attached suture and its relationship to the package assembled by the machine described herein.

Figure 1:
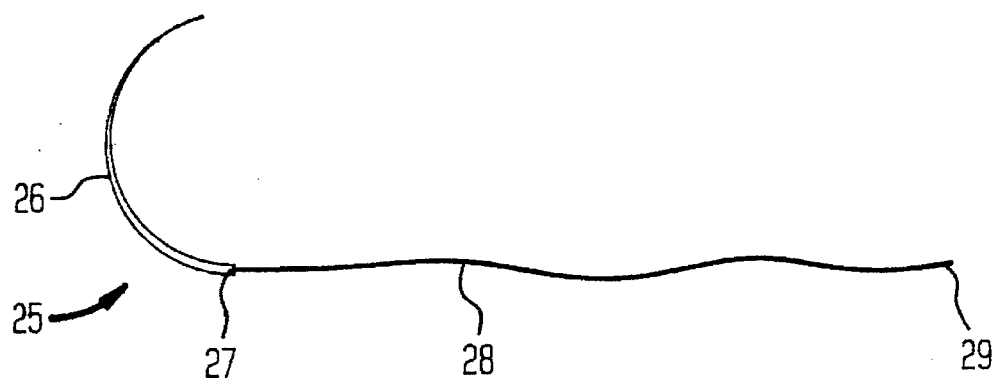
FIG. 1 illustrates a needle and attached suture.

FIG. 1 illustrates the needle with attached suture assembly 25, comprising the needle 26, butt or barrel end of the needle and the point of suture attachment 27, suture 28, and suture trailing end 29.

Figure 2:
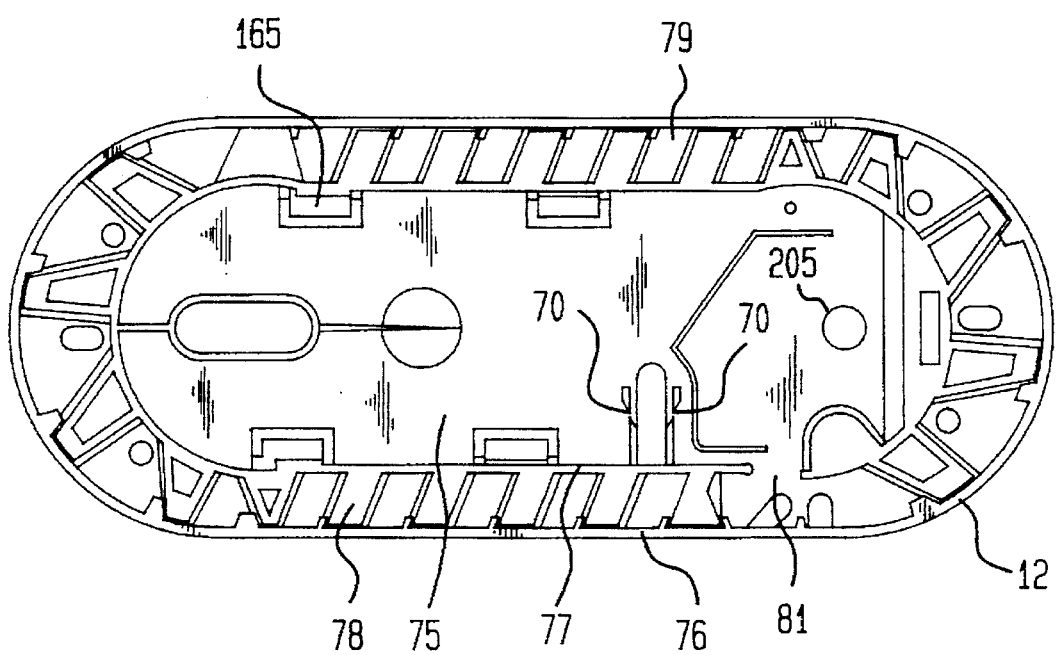
FIG. 2 illustrates an unassembled molded package tray.
Figure 3:
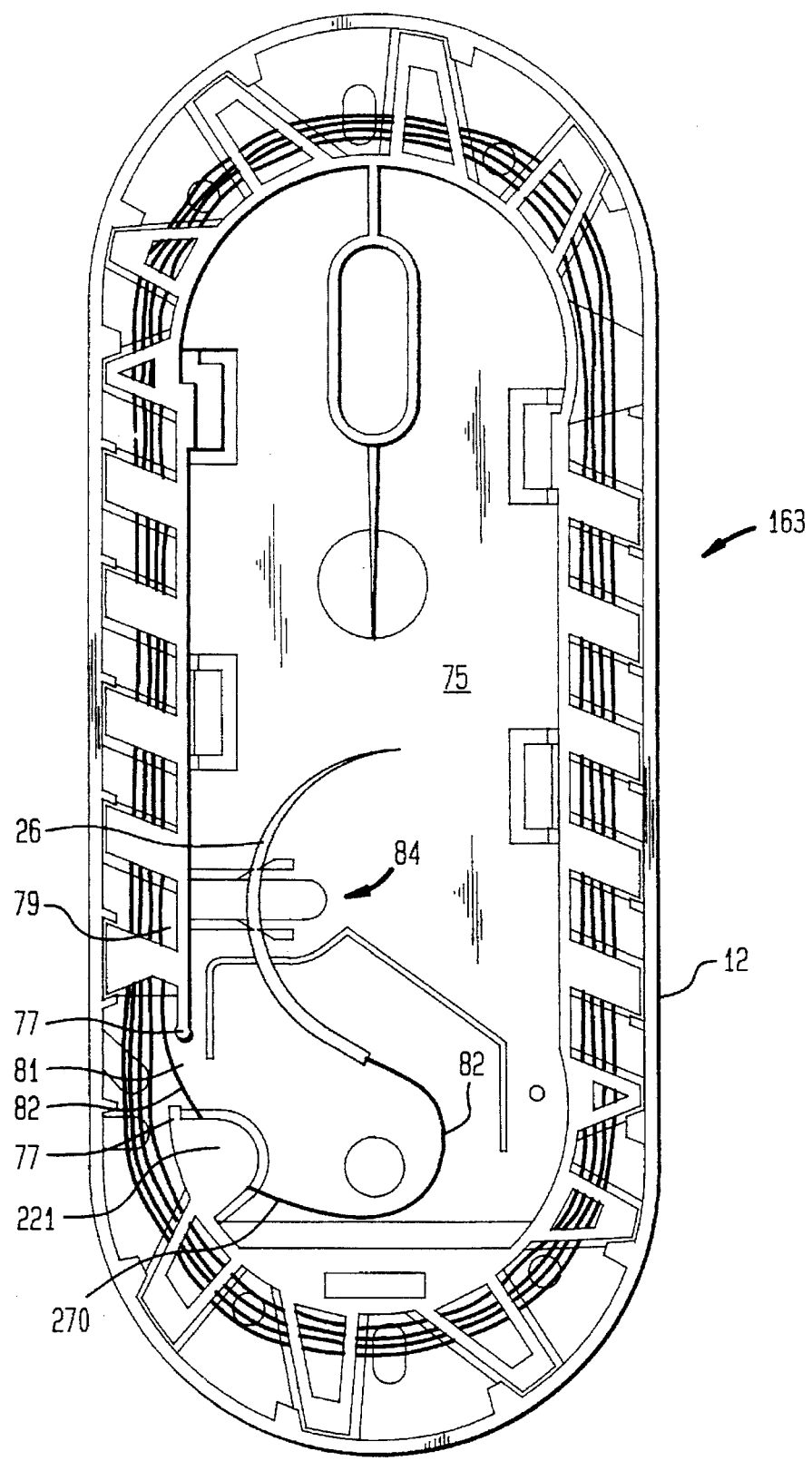
FIG. 3 illustrates a the package molding 12 with a needle and attached suture of FIG. 1 wound therein.
Figure 4:
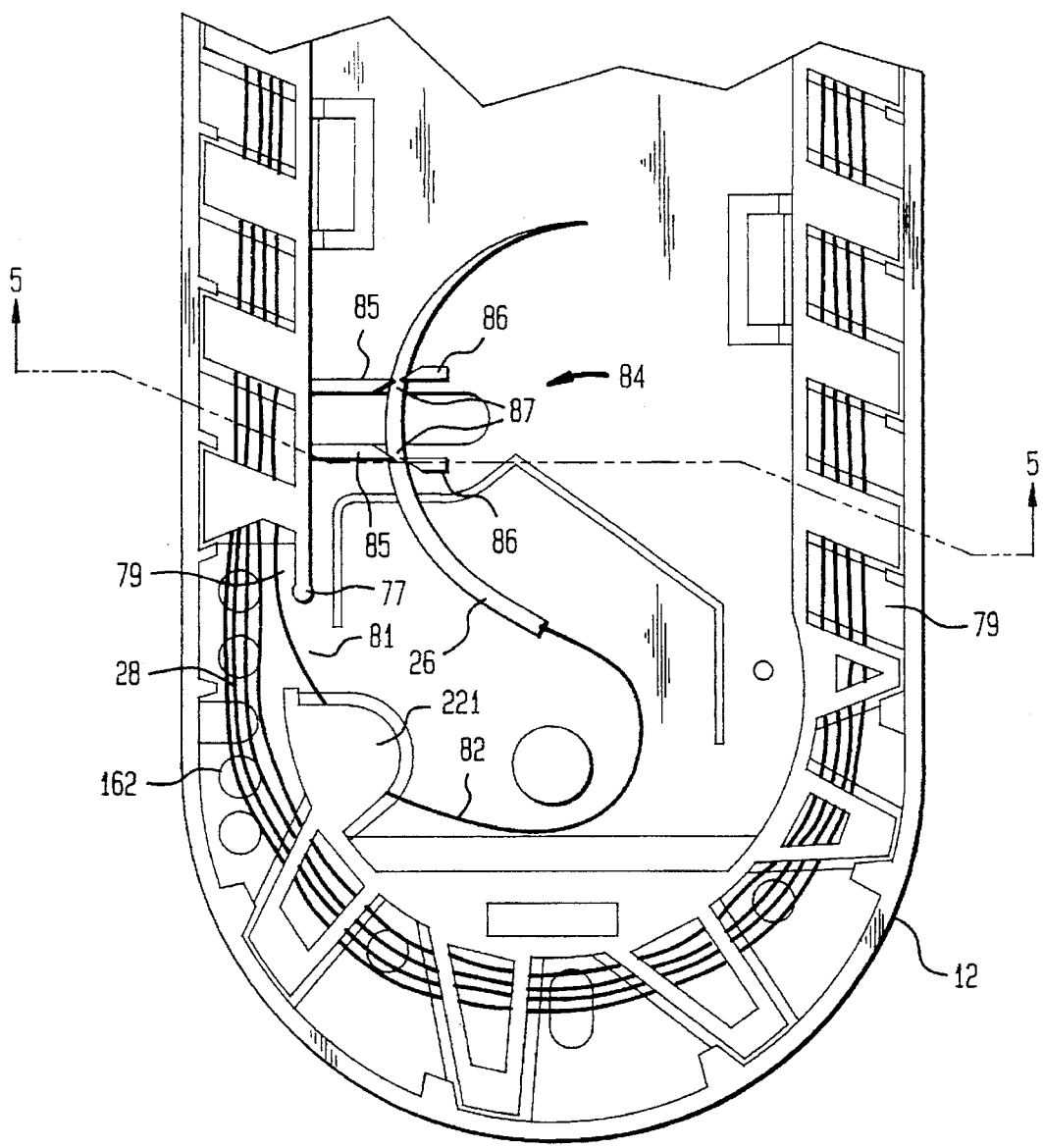
FIG. 4 illustrates an enlarged partial view of FIG. 3.
Figure 5:
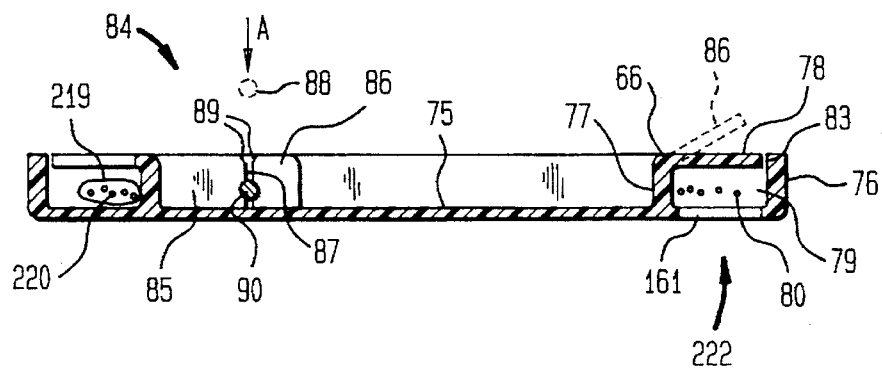
FIG. 5 illustrates an section through FIG. 4 in elevation view along section line 5—5.

FIG. 2 shows the empty package molded tray 12 that receives wound suture assembly 25. Referring also to FIGS. 3-5, tray 12 is comprised of a planar base 75, with parallel sides and essentially semicircular rounded ends. Vertical wall 76 is positioned on the periphery of base 75. Inward from and parallel thereto is a second vertical wall 77, and attached to and cantilevered from the top thereof, a plurality of flexible suture retaining fingers 78 extending generally radially outward to a point close to, but not touching, upper inner surface 83 of vertical wall 76. Base 75, outer wall 76, inner wall 77, and fingers 78 define a hollow peripheral channel structure 79 which confines suture wound spiral loops 80 therein as illustrated in FIG. 5. Tray 12 is made of resilient material such as plastic, thereby affording properties to suture retaining fingers 78 which allow being flexed hingedly about connection point 66 to position 86 shown in the dashed line illustration, of FIG. 5, and when released spring back to essentially original horizontal position 78, thereby facilitating insertion of suture 80 in the open position and containing the suture loops 80 therebeneath in channel 79 in the closed position. A plurality of openings 161, shaped similar to and spaced directly beneath each finger 78, is molded into tray 12 to permit access of tooling associated with suture insertion and a number of holes 162 are molded into tray 12 to permit vacuum assist. These are described hereinbelow where the winding operation is described in greater detail.

As illustrated in FIG. 3 and 4, a gap 81, inner wall 77 allows suture 82 to enter channel 79 for suture winding, and conversely exit for suture dispensing by the end user.

Located in the lower central portion of tray 12 is the needle holding means 84 referred to as a "needle park" illustrated in detail in FIGS. 4 and 5. It is comprised of two sets of generally opposing blades 85 and 86, with gap 87 therebetween, molded integrally in tray 12 and rising vertically from the floor of base 75. The functional qualities of this design for needle park 84 facilitate automatic loading by the relatively simple mechanical motion of pressing the needle wire diameter 88, shown in cross section, FIG. 5, downward in the direction of arrow A against chamfered surfaces 89, and, causing plastic deformation of blades 85 and 86, as the needle passes through gap 87, to position 90 indicated in FIG. 5. Needle 26 is thereby held securely by the plastic deformation forces in needle park blades 85 and 86 in the region surrounding needle position 90, and also permits relatively easy removal of needle 26 by the end user by sliding it axially from between blades 85 and 86 on a path coincident with the shape of needle curvature. Package tray 12 with assembled suture and attached needle, 163, is illustrated in FIG. 3.

Figure 6:
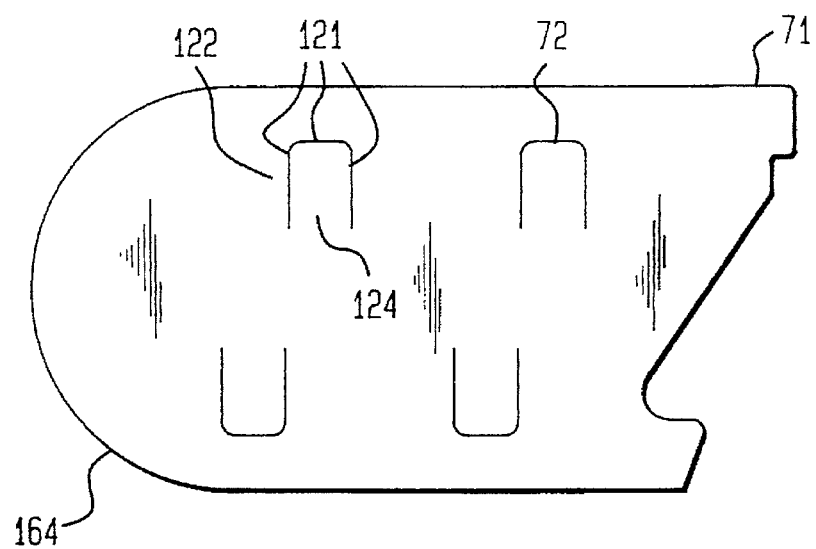
FIG. 6 illustrates the package label cover.

A package cover 71, as illustrated in FIG. 6, is made from paper or other sheet and material, is essentially a labeling surface and provides a protective shield for a portion of the package contents.

Figure 7:
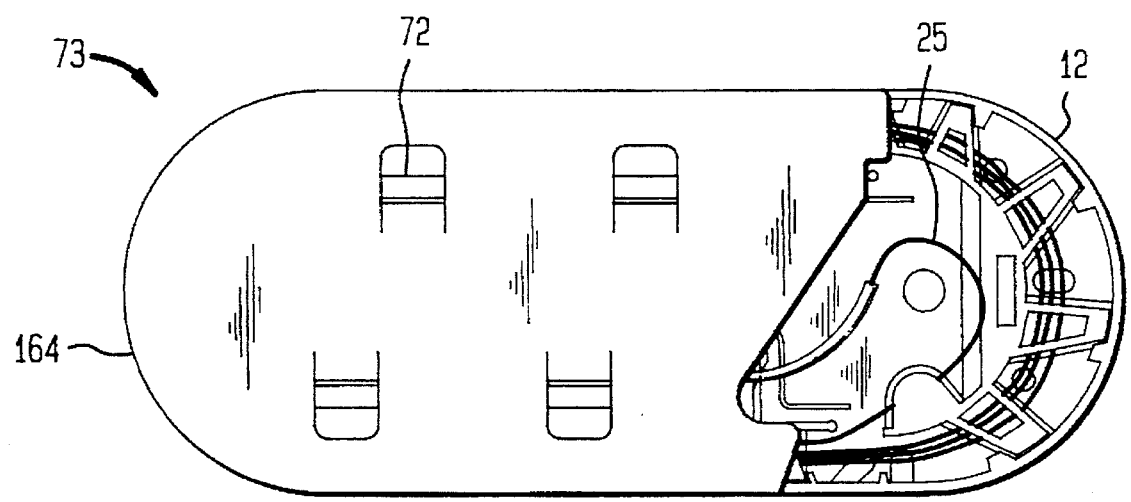
FIG. 7 illustrates the completely assembled package.

As illustrated in FIG. 7, cover 71 is attached to tray 12, by a plurality of tabs 72 which are defined by a diecuts 121 into cover material 122 on three sides. Package cover 71 is installed by locating parallel sided and radiused peripheral edge 164 above and coincident with the likewise shaped periphery of tray 12, such that the butt or barrel end 27 of the needle is exposed as illustrated in FIG. 7. Cover attachment is accomplished by staking locking tabs 72 into the coincident pockets 165 illustrated in FIG. 2 to the latch the cover to the molded tray 12 therebelow.

Figure 8:
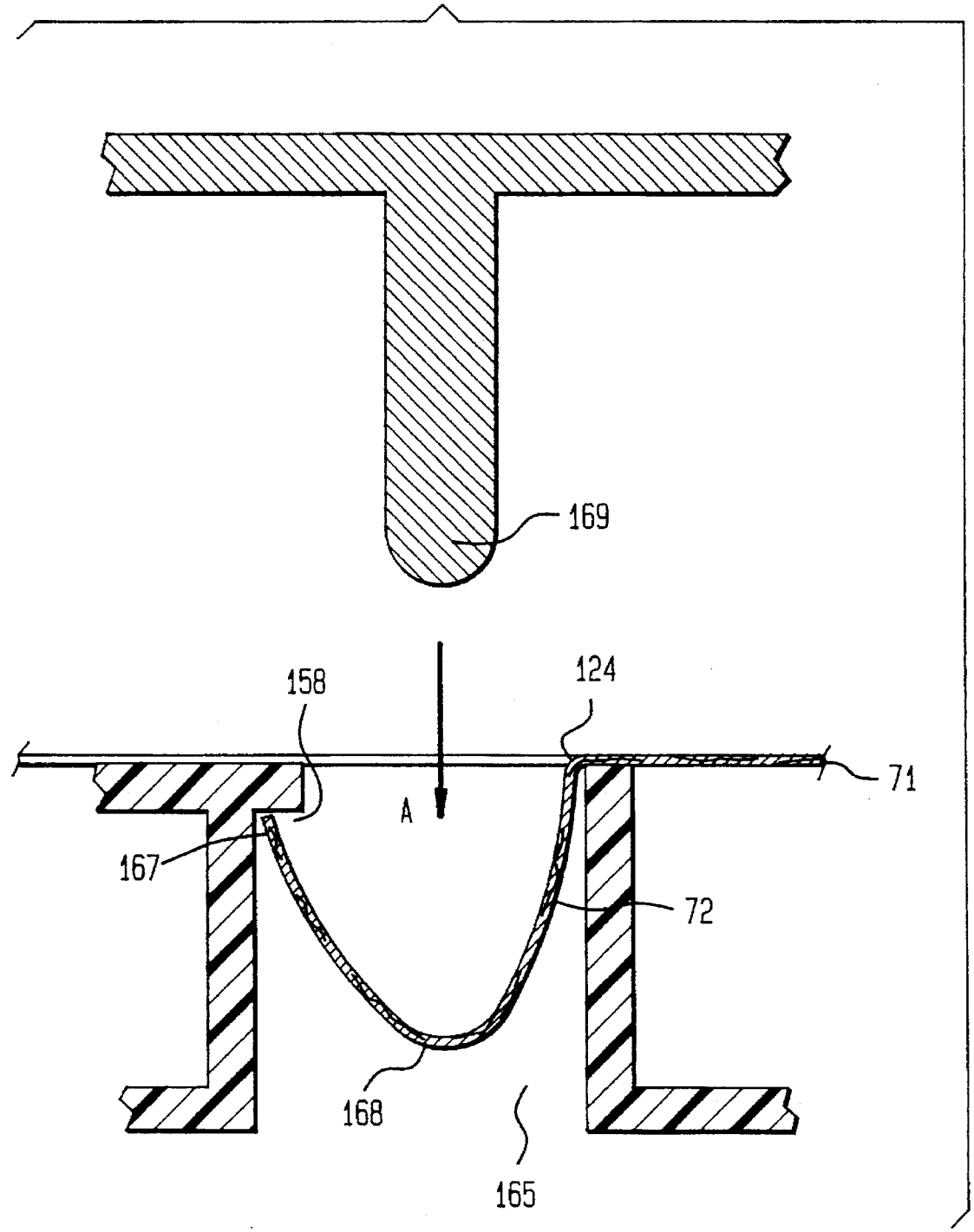
FIG. 8 illustrates an enlarged elevation view of a section through the staked label attachment tabs.

The locking tab function and installation is illustrated in FIG. 8. Tab pocket 165 is molded with shelf overhang 158 so positioned that tab end 167 is trapped to resist vertical upward movement after tab body 168 is staked and formed by staking tool 169 will be hereafter described in greater detail with respect to FIGS. 57A–D. The staking tool 169 is mounted on the assembly machine, and descends onto tab 72 and into pocket 165 in the direction of arrow A. Upon withdrawal of staking tool 169, tab 72 partially springs open resulting generally in the shape illustrated in FIG. 8.

Machine Overview

Figure 9:
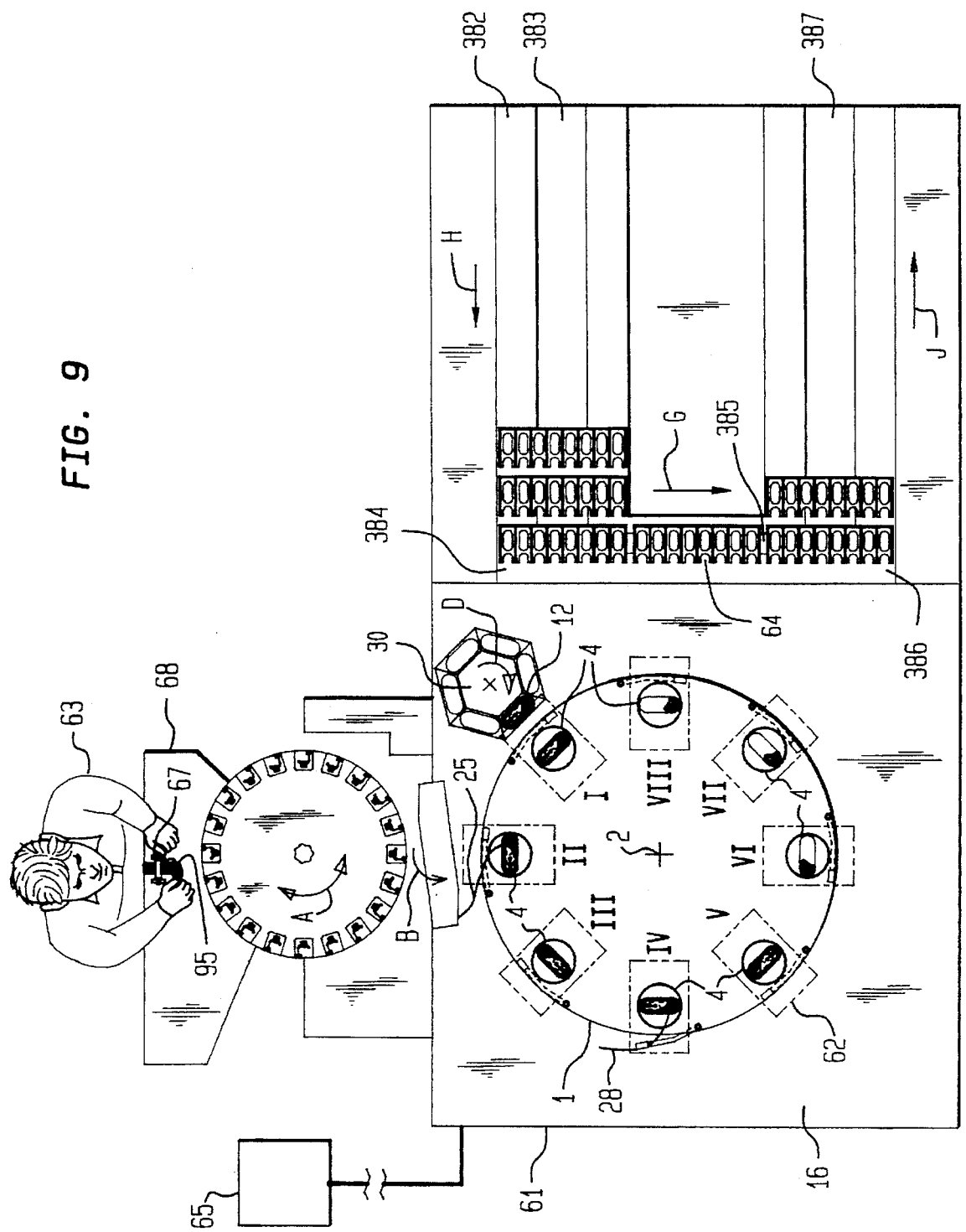
FIG. 9 illustrates a plan view of the entire machine.

Referring to FIG. 9, the suture winding machine is a rotary index assembly unit comprised of a machine frame and enclosure 61 which houses motion generating devices, a main rotary indexing disc shaped turret 1 with an equally spaced plurality of tool nests 4 mounted thereon. A plurality of corresponding package assembly mechanisms 62 are mounted stationarily on the machine top tool plate 16 positioned around the periphery of turret 1 and each are configured to perform a portion of the combined operations that comprise the complete assembly sequence. A programmable logic computer controller and supporting electronic systems 65 are housed in a control cabinet adjacent to the machine.

The sequence of assembly operations performed by the machine is herein described briefly for an overview. Continuing with reference to FIG. 9, machine station numbers referenced below correspond to position numerals I through VIII around the periphery of turret 1, and represent the sequence of assembly steps each tool nest 4 is exposed to as it is incrementally advanced by counterclockwise indexed rotation of turret 1 about vertical axis 2. In this embodiment of the packaging machine there are eight tool nests on turret 1, making the corresponding angular rotation index of turret 1 45° per machine cycle.

Figure 17:
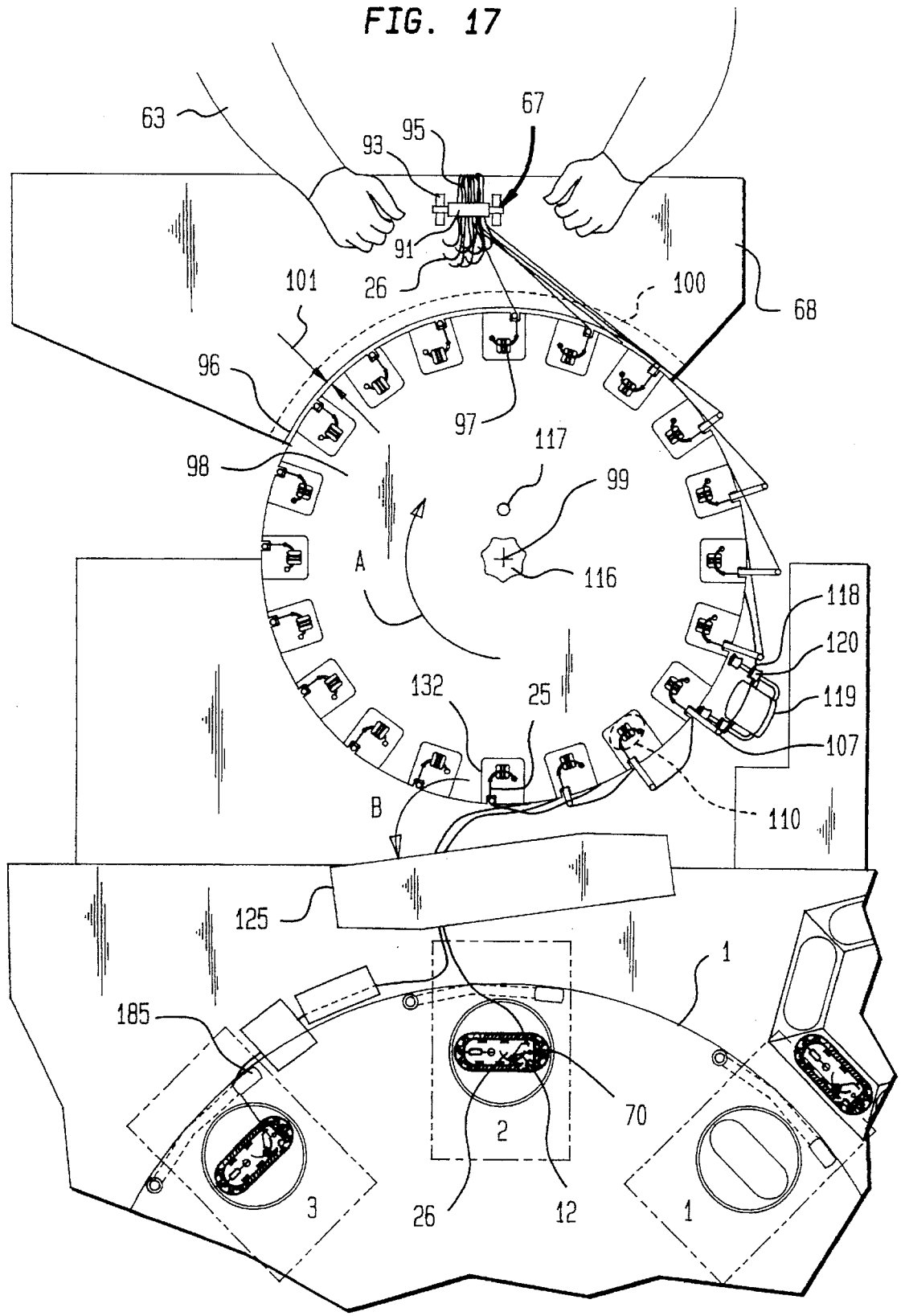
FIG. 17 illustrates an enlarged plan view of the machine focusing on the needle load station II.

Referring to FIG. 9 and the enlarged view of FIG. 17, the assembly operations of each automated workstation listed by machine station number around turret 1, are configured to perform the following operations:

(I) Load molded tray 12

(II) Transport needle with attached suture 25 to molded tray 12 and insert needle 26 into needle park 70 of molded tray 12.

(III) Rotate tool nest 4 with molded tray 12 partially to position suture 28 for the winding operation and secure the strand of suture 28 in post tensioner 185. This station includes machine artificial vision system inspection of needle placement.

(IV) Impart multiple rotations to tool nest 4 until suture 28 is completely wound in molded tray 12.

(V) Perform an optical inspection of needle and wound suture using machine artificial vision system with electronic digitizing camera.

(VI) Feed and place paper label cover 71 on molded tray 4 and secure to tray 4 by locking tabs 72 provided therein.

(VII) No operations performed.

(VIII) Unload completely assembled package 73 and place in material handling magazine 64 for the next factory operations. This position also removes defective packages to a reject bin, or on command, removes the completed package for manual inspection.

Following is a description of the above machine functions in detail, starting with the main turret:

Main Turret Description

Figure 11:
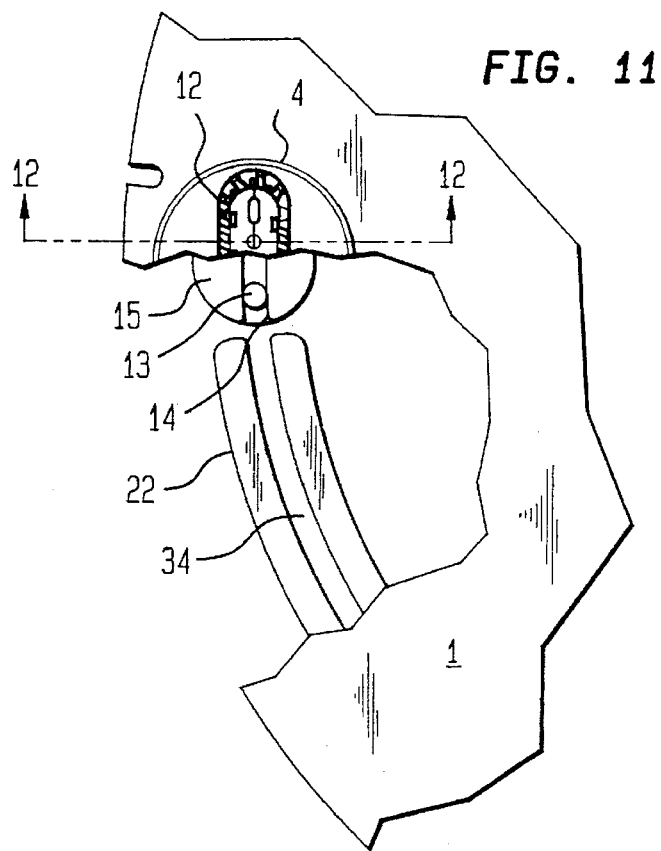
FIG. 11 illustrates a plan view of a tool nest on the main turret with a cutaway section showing a portion of the rotation system therebelow.

FIG. 11 illustrates the main assembly turret 5 or turntable 1, rotatably mounted about vertical axis 2 in machine frame 3. Turret 1 has a plurality of rotatable support members as tool nests 4 equally spaced about the periphery thereof and mounted rotatably thereon. Turntable 1 acts as a transport device to position, in stepped, indexed motion, each rotatable support member as tool nest adjacent to an assembly station mechanism that acts upon it at each index position. The succession of assembly operations performed on each tool nest resulting from this sequence produces a completed package assembly for each cycle of the machine, and operates at a relatively high cycle rate because multiple assembly steps are completed at the same time.

Tool Nest Description

Tool nest 4 receives the empty tray molding FIG. 2, at station 1, and carries it through the machine to complete the assembly illustrated in FIG. 7. Its many functions are described throughout the description for each machine station hereinbelow. Summarizing these, referring to FIGS. 14A and B, the tool nest is configured to:

1. Provide the lower tooling 224, 227, for winding the package.
2. Provide a rotation capability with rotatable bearing mounting 6 and cam roller drive 13. Provide a pilot pin 203 for precise tray location.
3. Provide a plurality of pockets, two of which are illustrated at 128 for staking the label cover tabs.
4. Provide a lower track 152 to guide a tail tucking stylus as will be hereinafter described.
5. Provide ejector rods 350 to raise the tray off tooling for unload grippers.
6. Provide spring loading as illustrated at 228 to provide compliance when locating the package tray against the upper tooling.

7. Provide a lock up means, which includes rods 334, to disable the spring loading 228 when staking the label on the package.

8. Provide vacuum porting 153 within to assist suture control during winding.

Figure 14A:
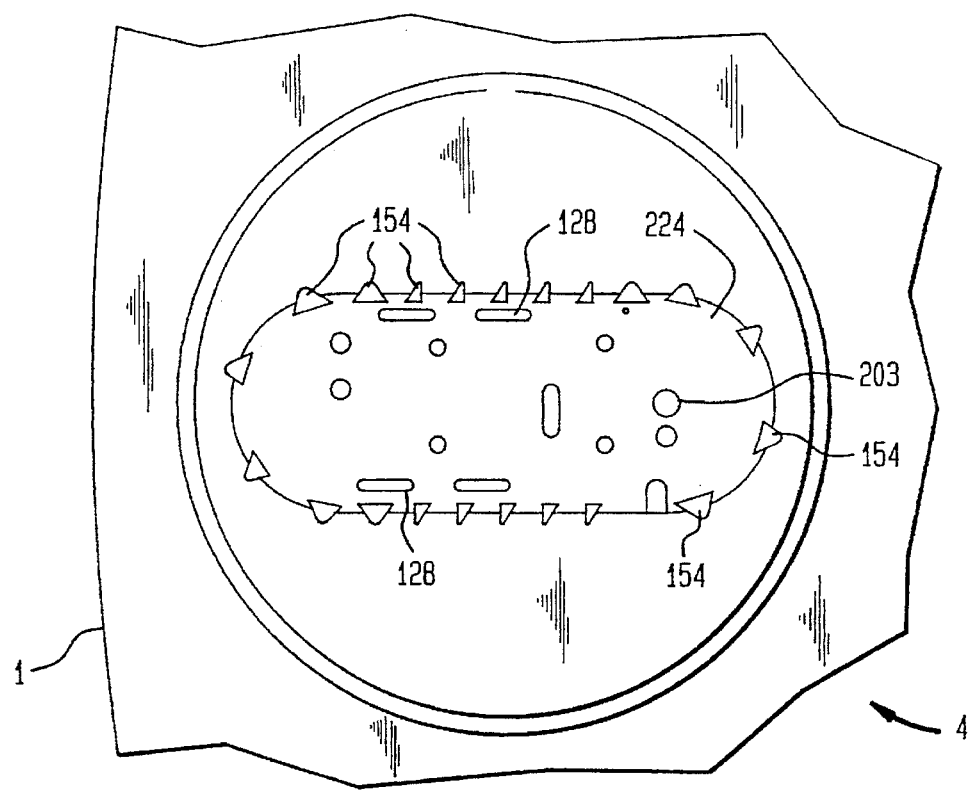
FIG. 14A illustrates a plan view of the tool nest.
Figure 14B:
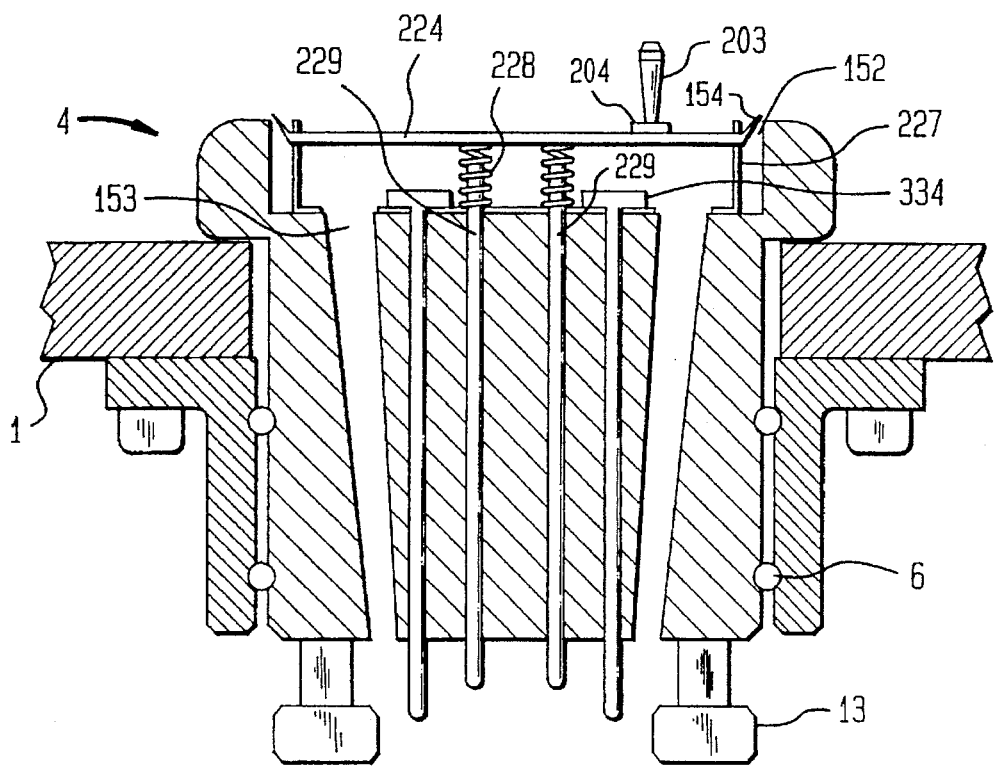
FIG. 14B illustrates a cross-sectioned view of the tool nest illustrated in FIG. 14A.

FIG. 14A is a plan view of one tool nest 4 on turret 1. It is understood that there are 8 such nests spaced evenly around the periphery thereof in the preferred embodiments, the tool nests are spaced on index table 1 to match that of the stationary assembly workstations 62 which interact therewith.

FIG. 14A and B illustrate the pilot pin 203 and tapered shape thereof which assists in keeping the suture loop controlled. The base of pin 203 has a shoulder 204 which is sized to be an interference fit with the mating hole 205 on the molded package tray 12 (illustrated in FIG. 2) which thereby anchors tray 12 to tool nest 4.

Figure 14C:
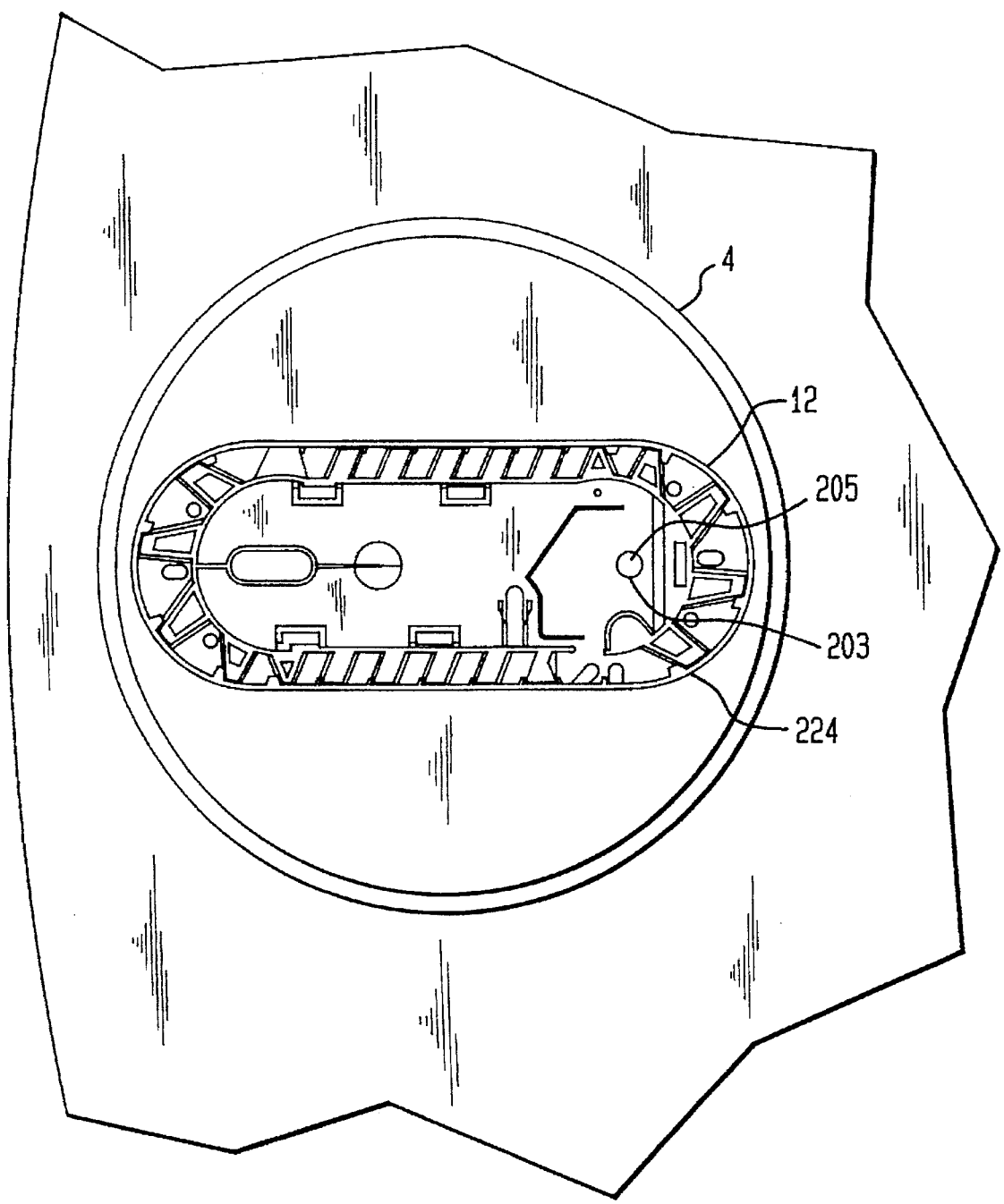
FIG. 14C illustrates a plan view of the tool nest with a package molding loaded thereon.

For most of the operating time of the machine, tool nest 4 has a tray 12 positioned thereon, in various stages of package assembly, which is supported on lower tool platform 224, as illustrated in FIG. 14C. Tray 12 is secured to platform 224 by an interference fit of the base 205 of pilot pin 203 in tray opening 205, and the plurality of lower platform fingers 154 which engage the bottom openings in the tray 12.

Each of the tool nests 4, are positioned on the periphery of turret 1, and are thereby enabled to sweep a curved path as turret 1 rotates in indexed increments described above. Tool nest 4 is also enabled to be driven in rotation about its own vertical axis to wind the suture assembled thereto.

Figure 12:
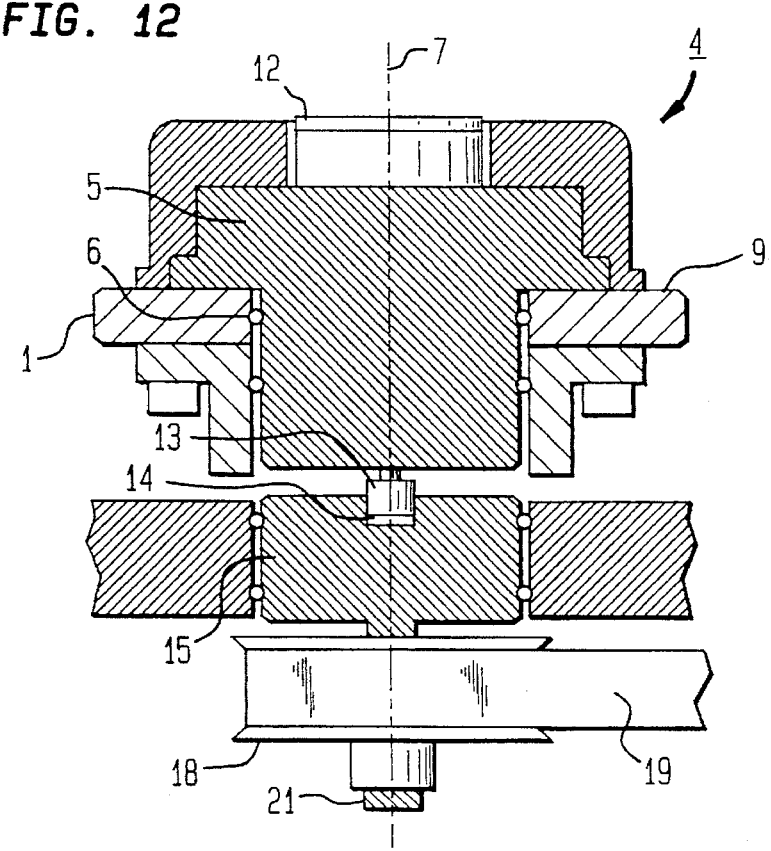
FIG. 12 illustrates a cross-sectioned elevation view of the tool nest rotation drive mechanism.

FIGS. 11A and 12B illustrate this multiple rotation mode capability plan and elevation views respectively. Referring to the sectioned elevation view in FIG. 12B, tool nest assembly 4 houses rotor 5 which is supported on bearings 6 and is rotatable about vertical axis 7 in turret 1. Package molding 12 is nested within and rotates with rotor 5 and is driven in rotation or held from rotation in certain rotational positions about axis 7 as required by the assembly process. This rotational control is transmitted through cam follower rollers 13, fixedly attached to the underside of rotor 5. The rolling elements of cam follower rollers 13 engage in a spindle slot 14 when turret 1 is in a rotationally dwelled position about vertical axis 2 (of turret 1). This dwell stage of the machine cycle positions all tool nests 4 at their respective operating assembly stations on the machine. Spindle 15 is driven by a suitably controlled motor, and in the preferred embodiment, is driven by timing belt sprocket 18, fixed to spindle shaft 21, which is inturn, driven by timing belt 19, which is correspondingly driven by an electronic servo motor controlled by logic controller 65.

Referring to FIG. 11, the drive system is illustrated in cutaway plan view. This illustration shows a portion of turret 1 with tool nest 4 mounted thereon, and package molded tray 12 positioned on tool nest 4 in typical position as required for the package assembly operation. The cutaway view under turret 1 illustrates elements shown also in FIG. 12B, including motor driven spindle 15 with spindle slot 14 therein. Cam follower rollers 13 are rollingly engaged in slot 14, positioned on the underside of rotor 5 for rotation thereof by drive spindle 15. The cam followed rollers 13 can also sweep circumferentially the open groove 34 in stationary guide rail 22 when the tool rest 4 is indexed between stations.

Figure 13C:
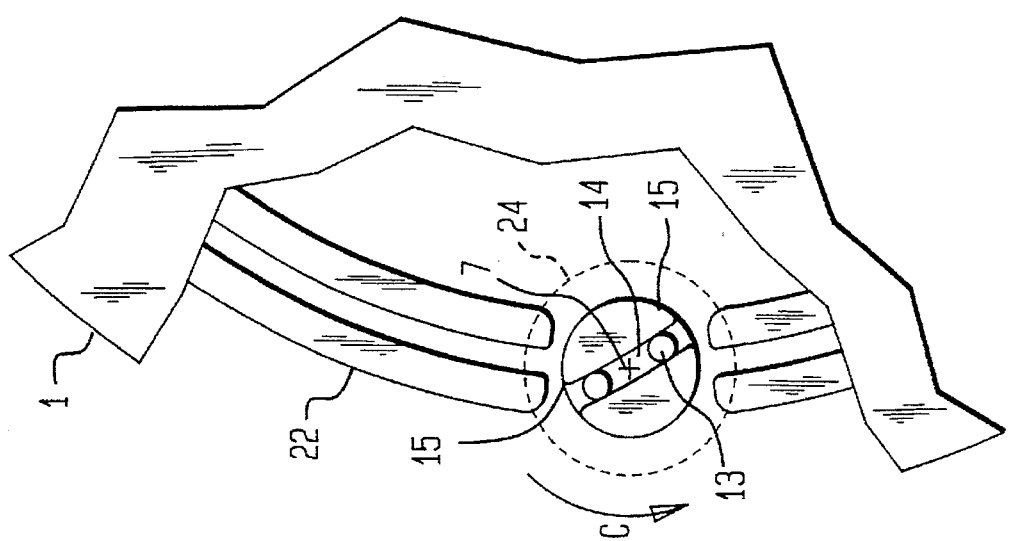
FIGS. 13A through 13C illustrate in successive Figures, a series of plan views of which illustrate the engagement of the tool nest rotation arrangement, sectioned to view under the main machine turret.
Figure 13B:
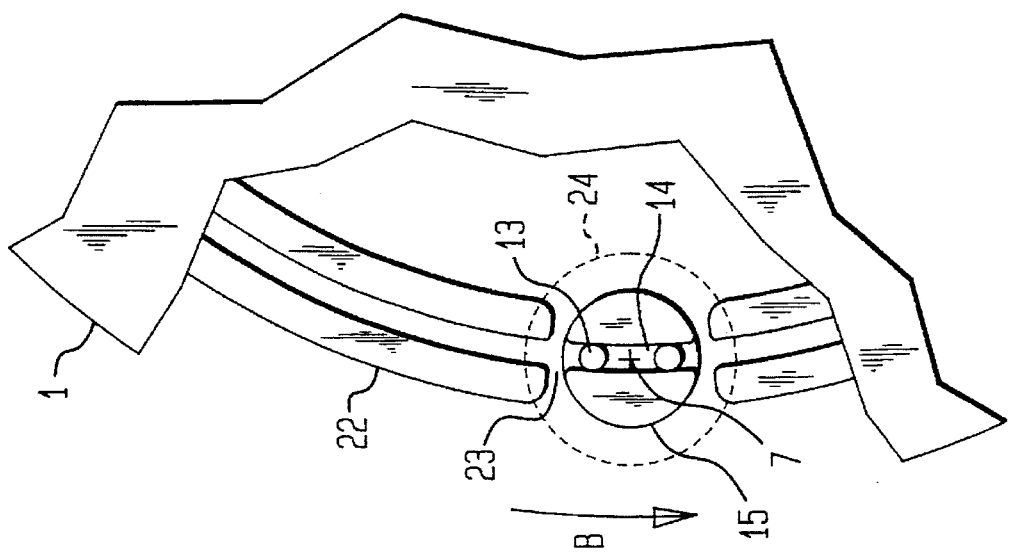
Figure 13A:
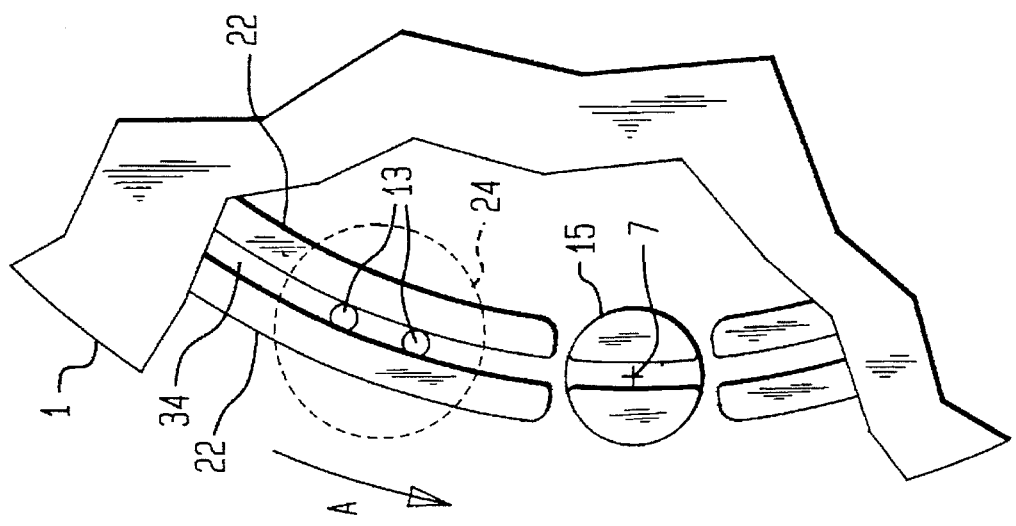

FIGS. 13A through 13C illustrate the interaction of the above elements in a typical machine cycle at a machine station requiring package rotation. A dashed line silhouette 24 of tool nest rotor 5 is illustrated in FIG. 13A, as it is nearing the dwell position over spindle 15 as main turret 1 advances in incremental rotation about its axis 2 (not shown) in the direction of arrow A. Cam followers 13 are rollingly captive in groove 34, confined and precisely located by side rails 22. FIG. 13B illustrates further rotation of turret 1 indicated by arrow B until reaching the dwell position shown, thereby positioning vertical rotation axis 7 of tool nest 24 coincident with the vertical axis of driving spindle 15 as previously described with respect to FIG. 12. Note that this has required rollers 13 to cross open gap 23 in transitioning from track groove 34 to spindle slot 14. FIG. 13C illustrates the spinning of tool nest rotor 24, driven in rotation about vertical axis 7 indicated by arrow C, by motor driven spindle slot 14 imparting similar rotary motion to tool nest rotor 5 through cam follower rollers 13. When the spindle 15 stops rotation, at the end of the machine cycle, spindle slot 14 is aligned with slot 34 to enable the tool nest and rotor 24 to be advanced to the next station 62.

Station (I)

Figure 15:
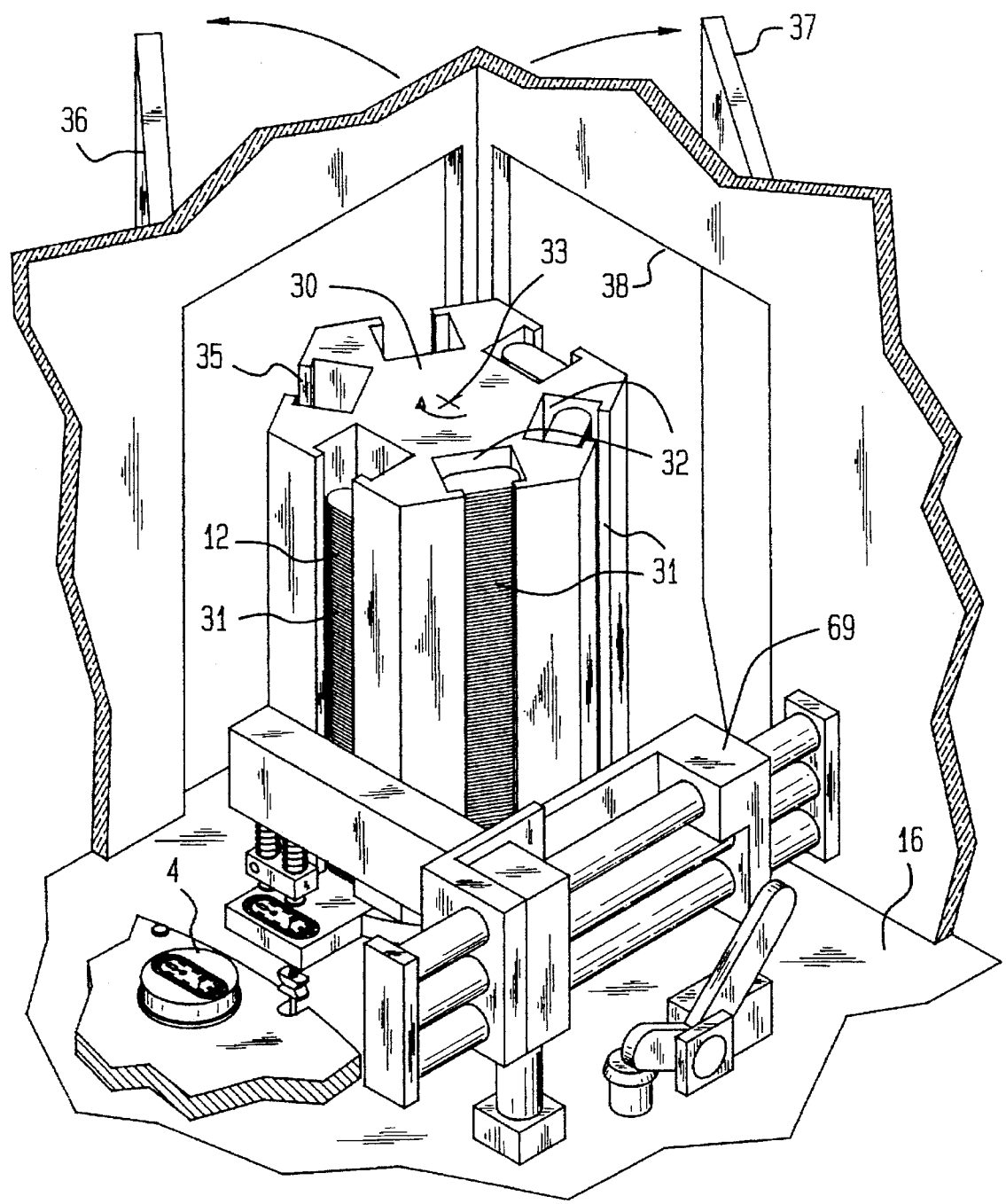
FIG. 15 illustrates an isometric view of the tray loading carrousel and associated mechanisms.

A loading station for inserting the empty molded tray to be assembled into a completed package is illustrated in FIG. 15. A primary objective of this station is to store and feed a sufficient quantity of trays to allow the machine to operate for an extended period of time without operator attention to reloading trays.

Tray carrousel 30, contains a plurality of vertical chambers 32 equally spaced in a generally hexagonal shaped structure. Carrousel 30 is incrementally indexed rotatingly about axis 33, in a clockwise direction indicated by arrow D, in 60° angular rotation segments by a cam controlled indexing transmission (not shown) below stationary tool plate 16. Each of the vertical chamber locations in FIG. 15 contain stacks 31 of empty trays to be fed to the machine. Vertical chamber 35, has been emptied and will be refilled at the next appropriate interval.

Provision is made to permit manual replenishment of depleted tray stacks into empty vertical chambers 35 without interrupting machine operation. This is accomplished by a machine attendant who may open doors 36 and 37, which are hingedly attached to stationary vertical wall 38 of the machine enclosure.

The following illustrates the operational sequence for carrousel 30 as pictured in FIG. 15. Carrousel 30 is configured so that the feeding out of trays 12 from the bottom of stack 31, when exhausted, causes a detector (not shown) to be energized, further causing carrousel 30 to index clockwise one 60° increment. In this manner, as the vertical cavities at all positions on carrousel 30 are emptied, they sequentially pass through the locations which are in close proximity to access doors 36 and 37 in the machine guard barrier to allow the attendant operator to manually refill them with a new stack of trays 31. Each vertical stack of trays 31 is of sufficient tray count to permit adequate time for stack replenishment before index motion of carrousel 30 is required, thereby minimizing the chance of a rotary index motion during the manual reloading process. If an index of carrousel 30 were to occur during manual stack replenishment, the index speed is sufficiently slow to not pose a hazard to the operator.

Trays are individually fed from the bottom of vertical stack 31 in carrousel 30, which positions the stack over the tray dispensing mechanism described hereinbelow.

Figure 16A:
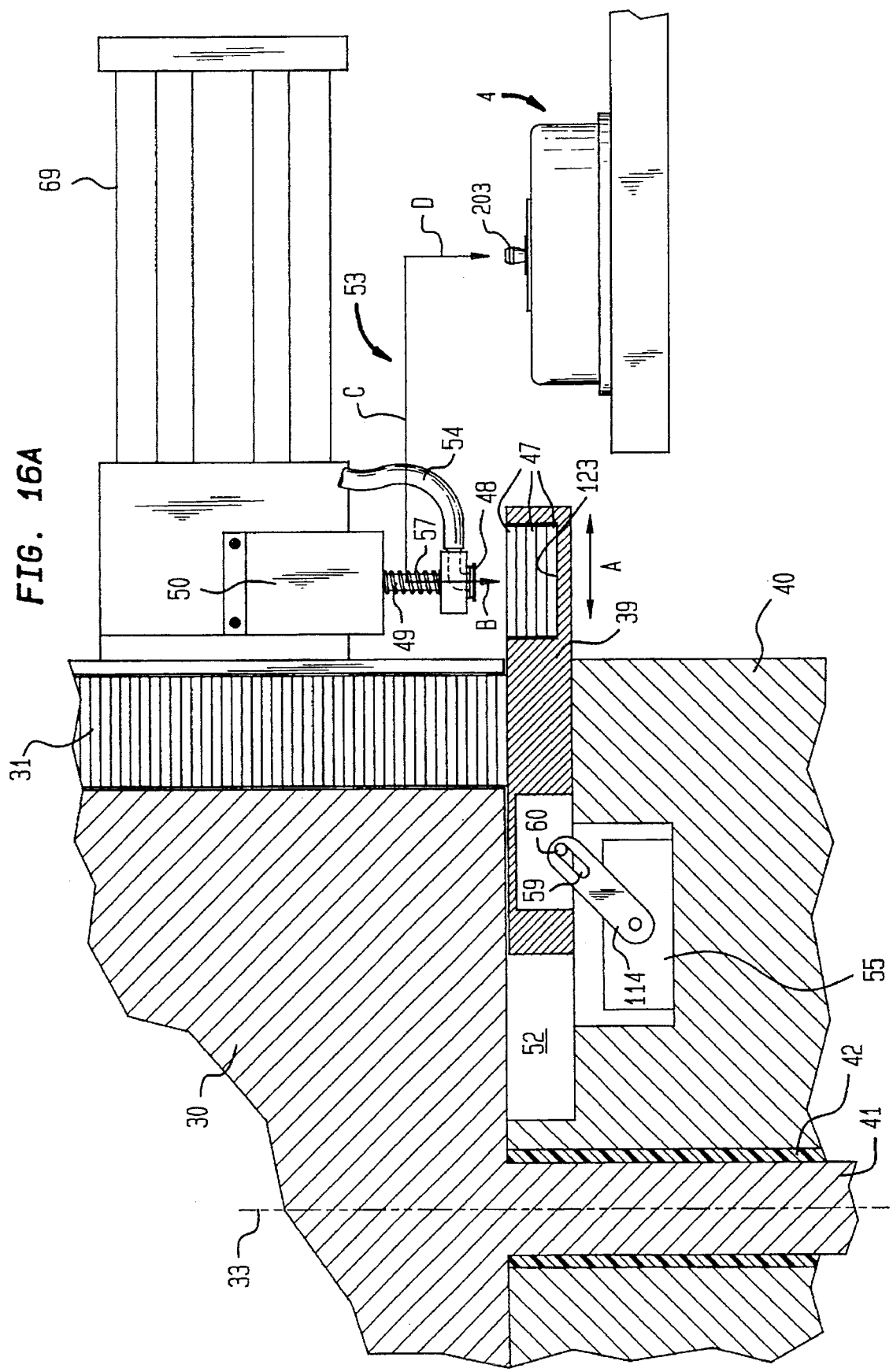

Referring to the sectioned elevation view, FIG. 16A, the tray feeding system is comprised of carrousel base 40, upon which is rotatingly mounted the carrousel 30, controlled in rotation about axis 33 by vertical shaft 41 guided by vertical bushing 42. Carrousel shaft 41 is driven by an indexing transmission (not shown) that, on control system command, incrementally rotates so that the next filled chamber is positioned for discharge. Tray shuttle 39, is mounted slideably in corresponding channel 52 in base 40 and is driven by angular rotation of lever 114 by drive 55 attached thereto, such that slot 59, engaging pin 60, imparts a sliding motion to shuttle 39, in either direction, as indicated by arrow A.

Figure 16C:
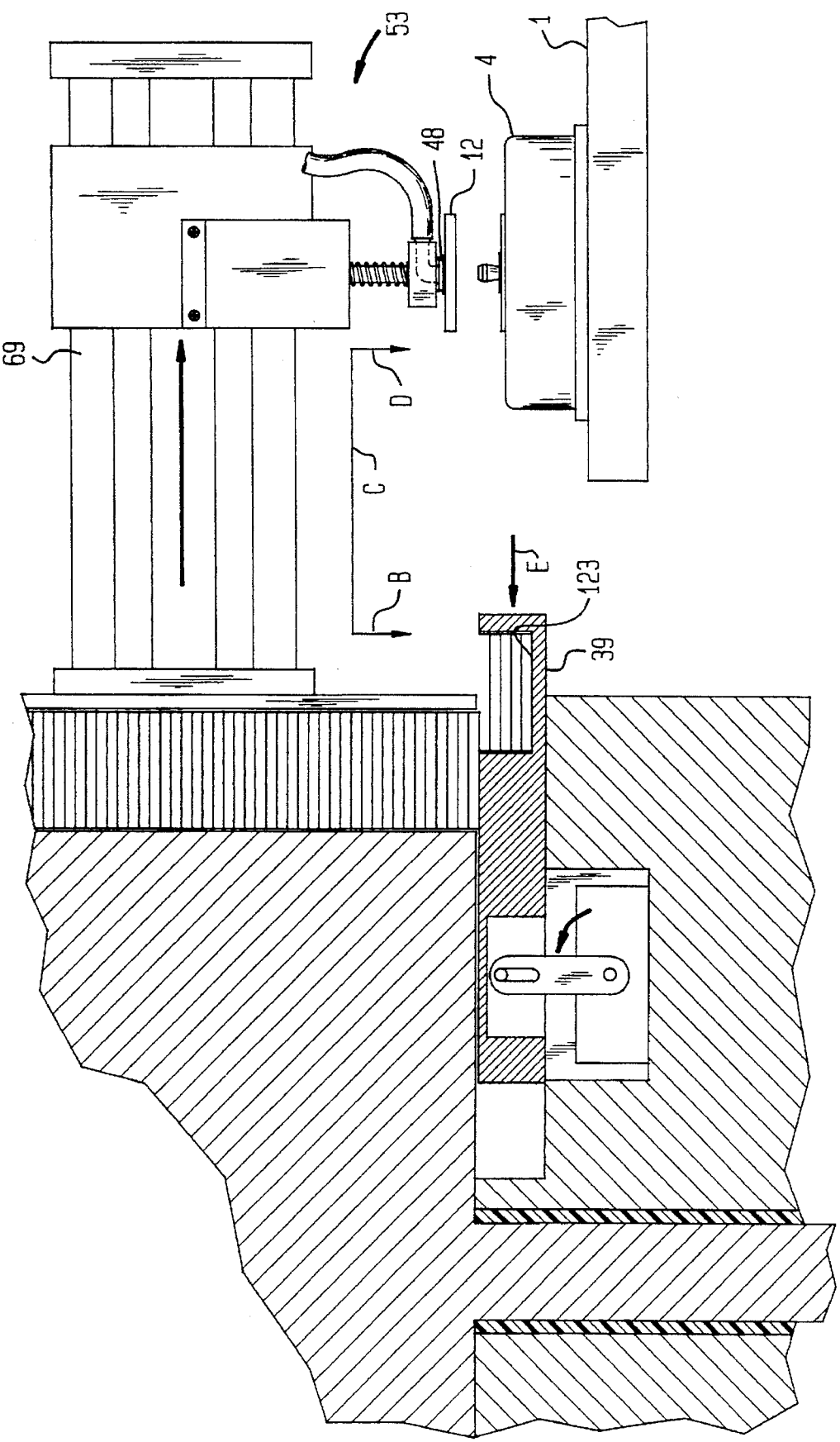
Figure 16D:
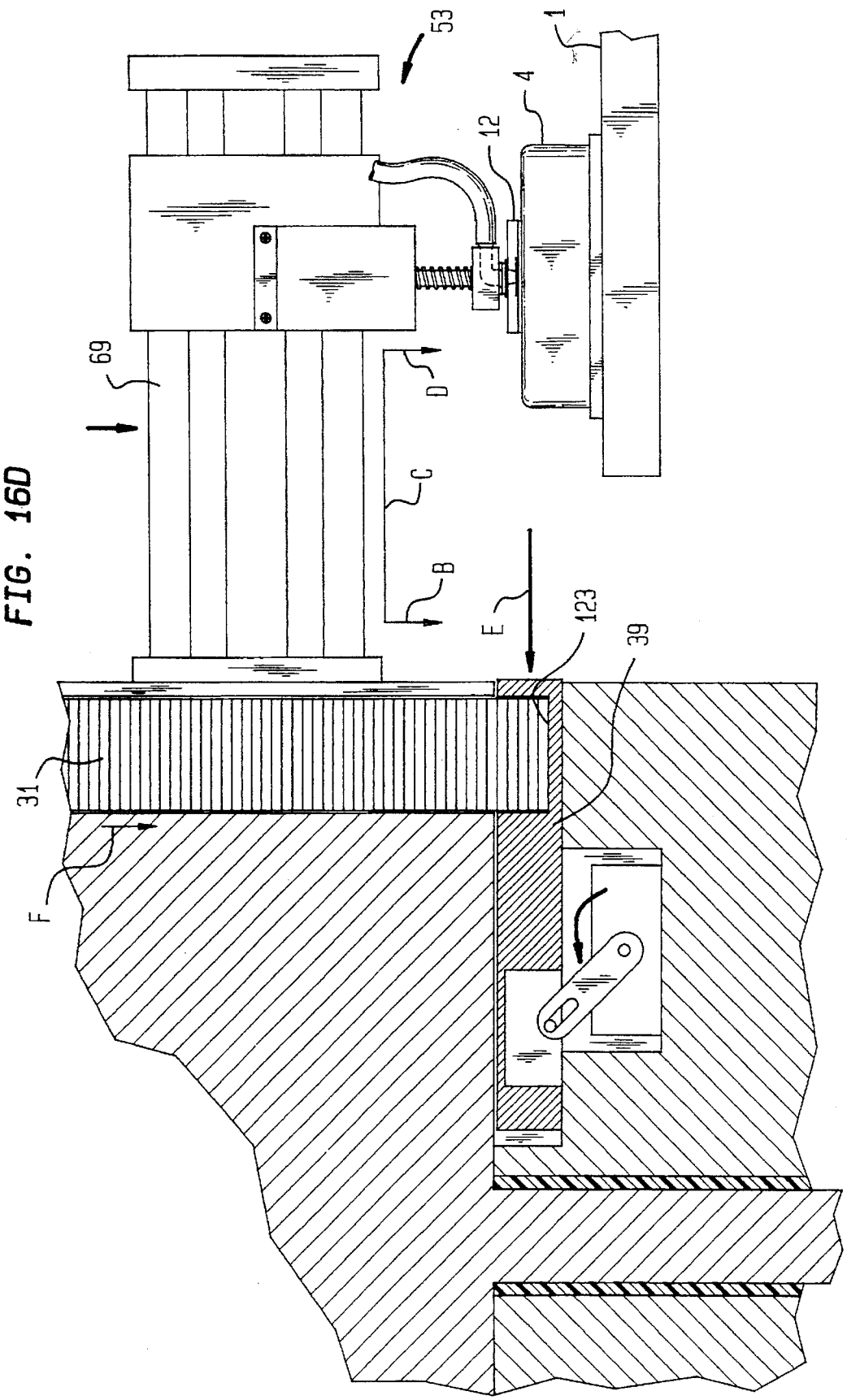
Figure 16E:
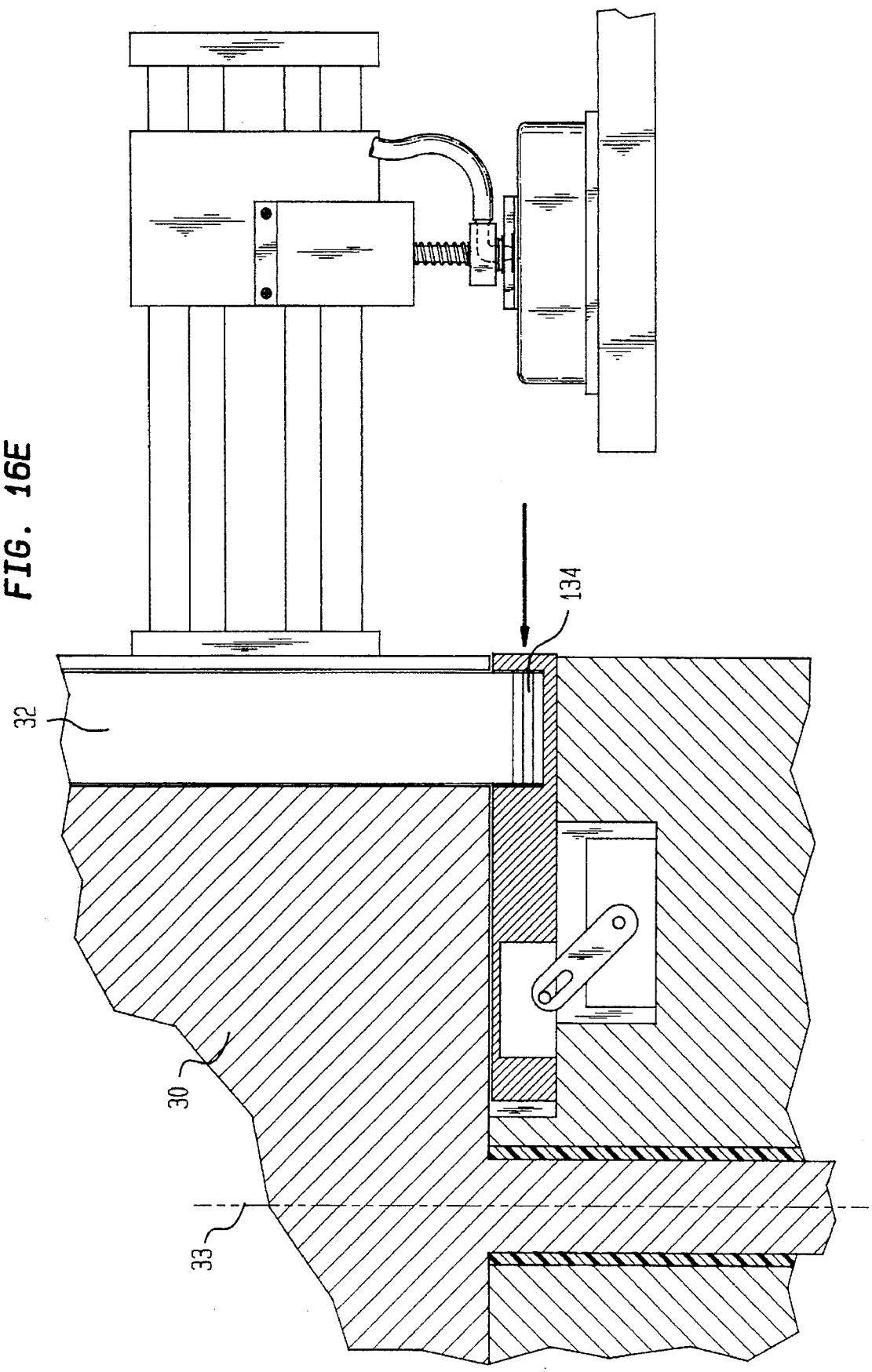

A vacuum cup assembly 53 includes a vacuum cup 48, mounted to vacuum cup tube, slideably attached to mounting block 50, and resiliently adaptable to variable vertical displacement by spring 57. A controllable vacuum source to cup 48 is supplied through hose 54. Slide assembly 69 is a cam driven pick-and-place unit that generates horizontal and vertical rectilinear repeating motion for block 50 in the path indicated by arrows B, C, D. As illustrated in FIG. 16B, the input to slide assembly 69 is a rotary shaft (not shown) driven by and synchronized with the machine main drive system. The sequence for feeding tray 47 is; 1) slide assembly 69 lowers vacuum cup assembly 53 indicated by arrow B causing vacuum cup 48 to contact top tray 47 in shuttle pocket 123. Vacuum to grip tray 47 is energized by the machine control system; 2) Slide assembly 69 moves vacuum cup assembly with tray 47 gripped thereto over tool nest 4 as indicated by arrow C, in FIG. 16C. Concurrently, shuttle 39 is withdrawn in the direction of arrow E. As illustrated in FIG. 16D, slide assembly 69 lowers vacuum cup assembly 53 and places tray 47 on tool nest 4, which is mounted on and positioned by turret 1. Concurrently, slide 39 is further withdrawn until slide cavity 123 translates under vertical tray chamber 32, causing tray stack 31 to drop, indicated by arrow F, replacing the tray 47 removed by the cycle described above; 4)When vertical chamber 32 is depleted of trays, as illustrated in FIG. 16E, shuttle 39 continues to be extended by lever 114 to the position shown in FIG. 16A, and vacuum cup assembly 53 is supplied by reserve trays 134 in shuttle pocket 123, avoiding machine interruption, until carrousel 30 has indexed another full tray stack into position thereabove.

Station (II)

The machine is adaptable to an automatic suture feeding device installed in the place indicated for the manual operator, the major machine functions being generally the same as described for the manual feeding hereinbelow described.

The needle feed wheel and needle transfer mechanism will be describe with respect to FIG. 9 and enlarged FIG. 17, which together illustrate the configuration of the manual operator controlled loading station. Bundle tensioner 67 accepts a bundle of surgical needles and attached sutures, and loader plate 68 provides a surface for the needles 26 to be arranged generally flat thereagainst.

Figure 18:
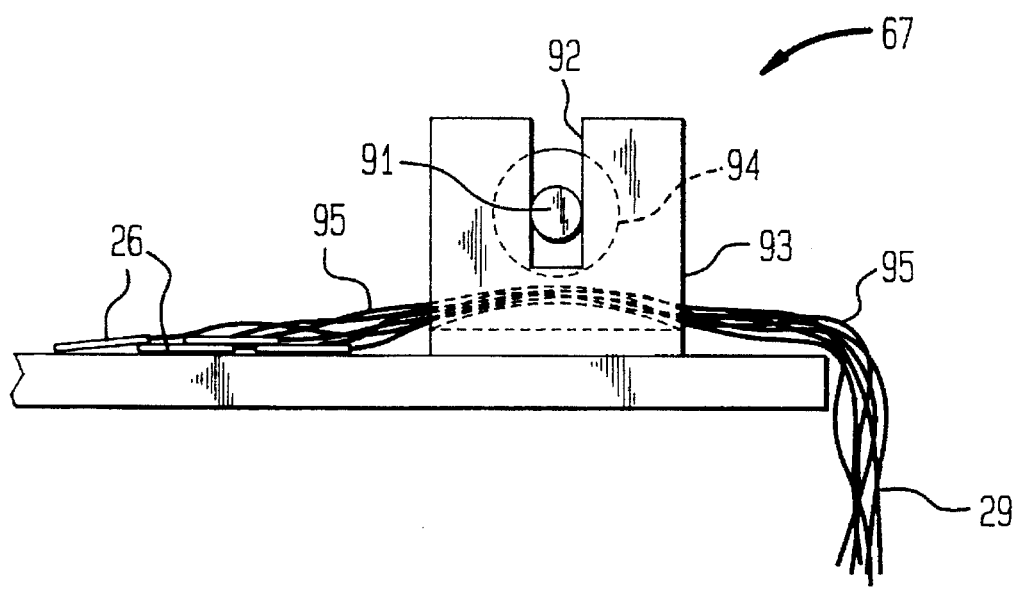
FIGS. 18 is an elevation view of the suture bundle tensioner.

Referring to FIGS. 18 and 19B, tensioner 67 is comprised of a weight 91 engaged in vertical slot 92 in tensioner body 93, so that a resilient surface 94 bears against suture strands 95. The actual weight of weight 91 has been predetermined to a value that secures suture strands 95 sufficiently to prevent movement from their own weight but loosely enough to allow them to be slideably withdrawn by moving needles 26 laterally away from tensioner 67 without high tension or damage to the suture material. Trailing ends 29 of suture bundle 95 depend downwardly from tensioner 67, and hang freely therefrom in the region of the operator's lap.

Referring to FIG. 17, the primary duty of operator 63 with regard to feeding the machine is to single out an individual needle 26 from suture bundle 95 and place it into one of the needle pocket 97 of needle wheel 98 at a production rate that keeps up with the machine speed setting. Needle wheel 98 is a disc shaped horizontal plate with a circumferentially positioned evenly spaced plurality of needle pockets 97 recessed therein. Needle wheel 98 is driven to index about vertical axis 99 in incremental rotary advancements of one pocket clockwise, as indicated by arrow A, at each machine cycle. In the instance of the embodiment illustrated, there are twenty needle pockets in needle wheel 98, and each incremental rotary advancement correspondingly 18°. The angular advancement of needle wheel 98 is therefore relatively small. The rotary motion is driven by a rotary index transmission (not shown). The small index distance required produces gentle angular accelerations and minimal peripheral velocity. The resulting peripheral motion of needle wheel 98 does not impose an unsafe condition for the hands of operator 63 if in contact with it during movement.

The elevation of the top surface of needle loading plate 68 is coplanar with the top surface of needle wheel 98. Loading plate 68 has a concave curved surface 96 the radial center of which is coincident with axis 99. The curved surface 96 has a radius slightly greater than the outer diameter of needle wheel 98, resulting in gap 101 therebetween, in magnitude less than the wire diameter of needle 26, making it possible for the operator 63 to slide the needle 26 across gap 101 into needle pocket 97 without the need to pick it up with fingers. The arcuate length of surface 96 in needle plate 68 provides the operator 63 the opportunity to load any of the plurality of needle pockets 97 opposite it, in this instance those indicated by dashed line 100. This feature allows the operator 63 to work at a pace not necessarily Synchronized cycle-by-cycle to the machine, and allows operator a degree of flexibility in needle placement cycle time as long as the net time averages the machine production rate. The operator 63 can stop the machine with an electronic foot pedal control (not shown) if not able to keep up with the machine cycle rate. The aforementioned features of the needle feed system result in minimal operator fatigue and maximum production rate.

Figure 20:
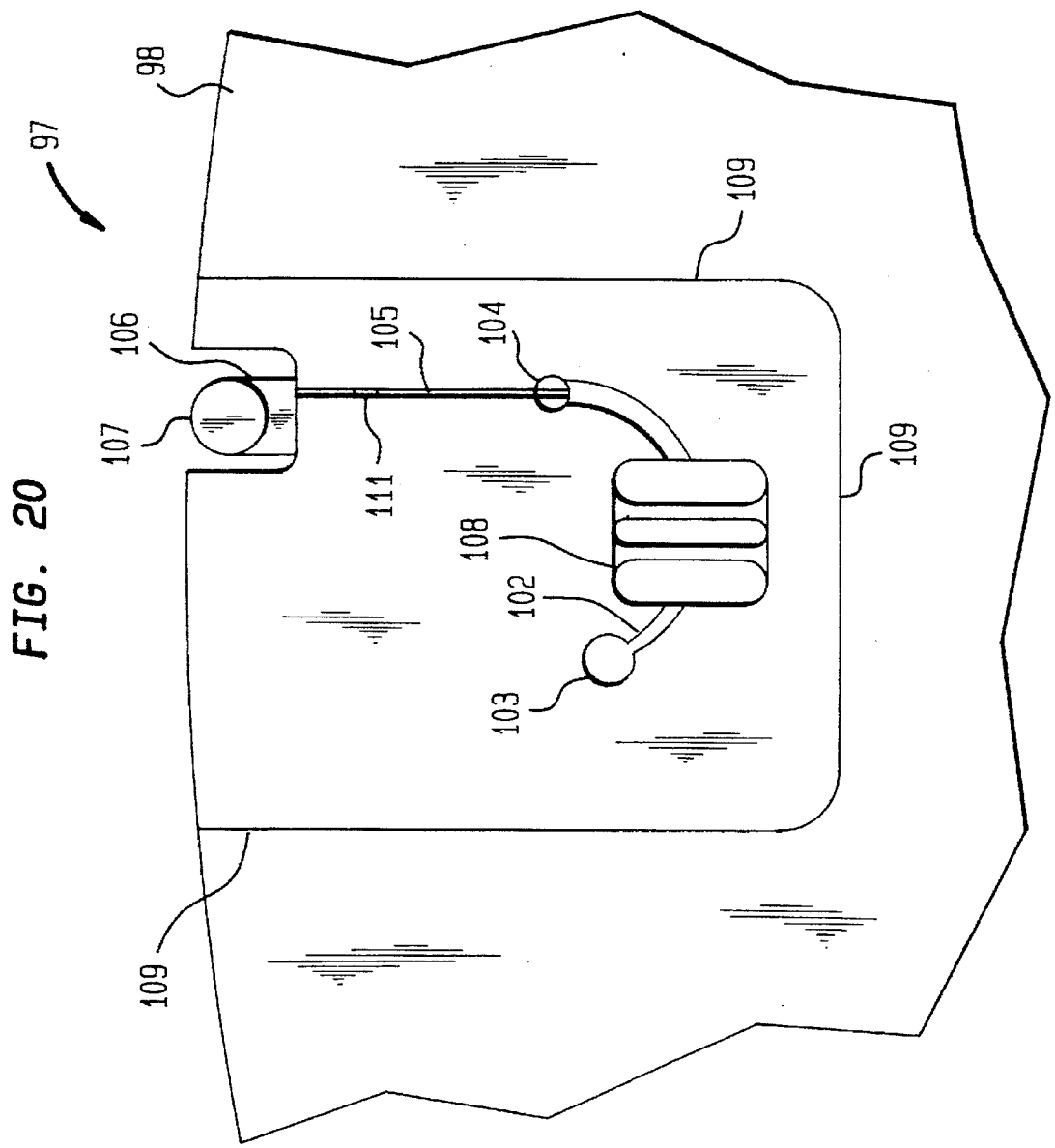
FIG. 20, illustrates an enlarged view of the needle pocket in the needle wheel.

As illustrated in FIG. 20, the needle pocket 97 in needle wheel 98, refer also to, is comprised of needle recess 102, needle point clearance 103, needle end stop 104, suture groove 105, suture displacement slide 106 with suture displacement pin 107 fixed thereto, and needle gripper clearance grooves 108 which are recessed to a lower elevation than needle pocket 102. Needle recess 102 is shaped to approximate the shape of needle 26 but with adequate clearance to allow imprecise and therefore easy manual needle insertion by the operator 63.

A removable insert, having boundaries defined by parting line 109, allows for simplified maintenance in the event of damage thereto, and permits the use of non-magnetic material such as plastic, facilitating use of an electronic metal proximity detector 110, as illustrated in FIG. 17, fixedly attached over needle wheel 98 for detecting an empty needle pocket and corresponding signal to the control computer to withhold a cycle of package assembly turret 1.

Figure 21:
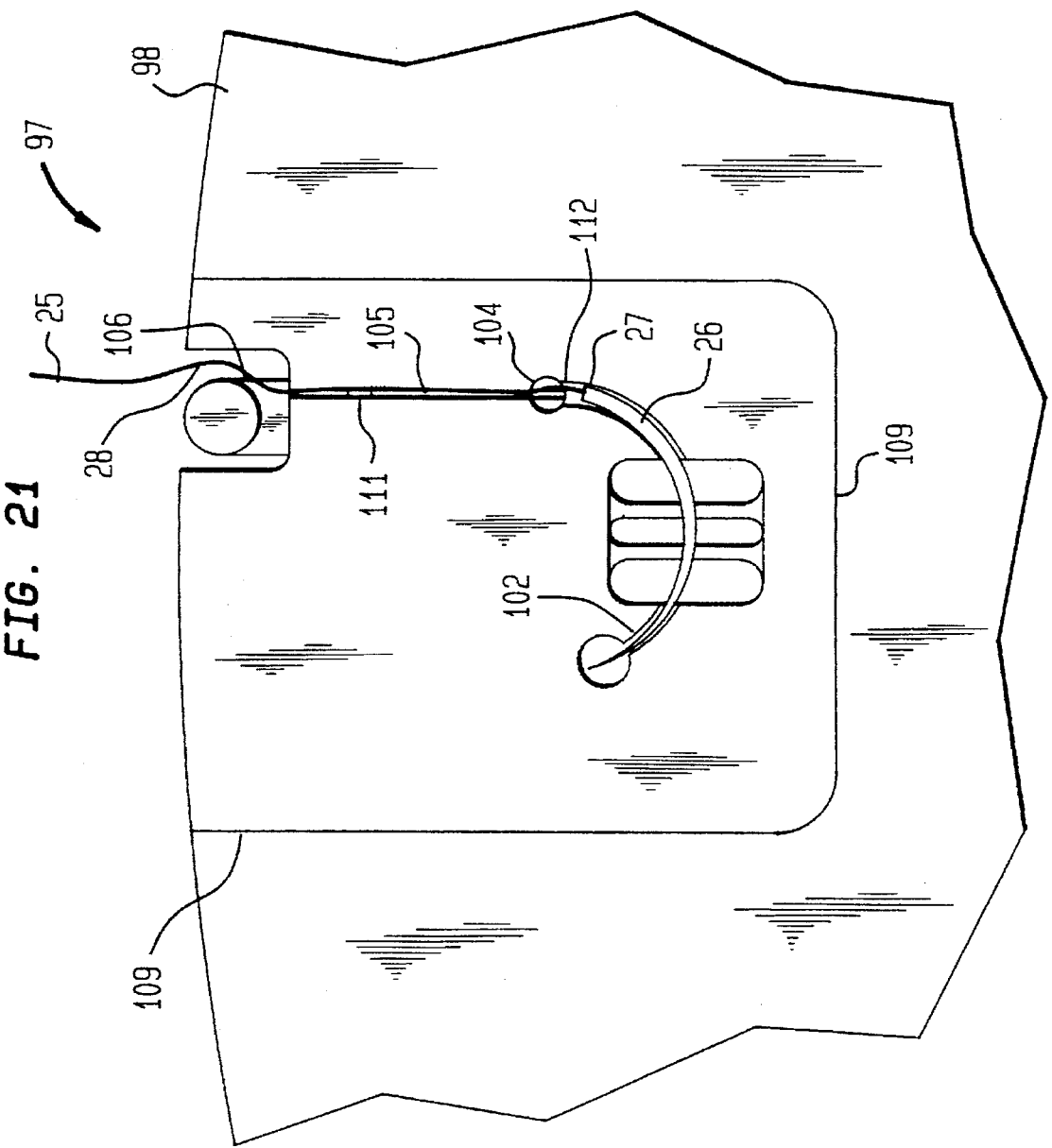
FIG. 21 is an enlarged plan view of the needle park illustrated in FIG. 20 with a needle and suture therein, prior to alignment.
Figure 22:
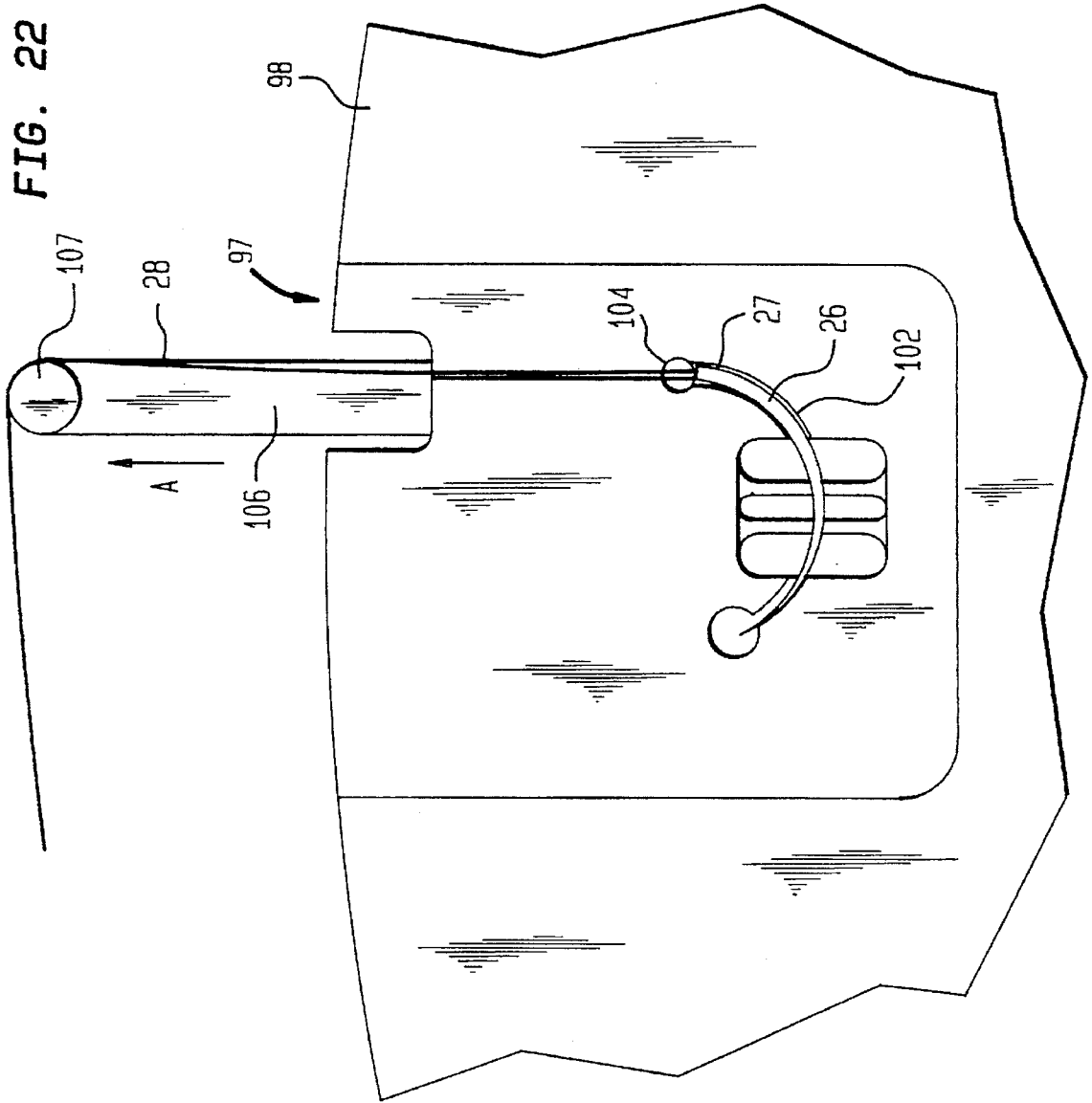
FIG. 22 is an enlarged plan view of the needle park illustrated in FIG. 21 with a needle and suture thereon, as it is aligned.

FIGS. 21 and 22 further illustrate the function of needle pocket 97. Needle pocket 97 easily accepts needle 26 placed by operator 63. Imprecise placement of needle 26 in needle recess 102 results in gap 112 between needle end stop 104 and needle butt end 27. A vacuum opening 111 in suture groove 105, is ported to a vacuum source below needle wheel 98 (not shown), and is configured to engage and secure suture 28 in suture groove 105.

A suture displacement slide 106, illustrated in FIG. 22, is slideably mounted in the rotatable support structure below needle wheel 98, and is mechanically linked to be cammed radially outward in the direction of arrow A as needle wheel 98 advances in incremental clockwise rotation about axis 99 as in the foregoing description. This enables suture displacement pin 107, to pull taut any slackness in suture strand 28 between needle 26 and the bundle tensioner 67 described with respect to FIG. 18. Continued radial displacement of pin 107 exerts a pulling force vector on needle 26, causing it to slide rotatingly counterclockwise in needle recess 102 until needle butt end 27 comes to rest upon needle end stop 104. This causes needle 26 to be precisely positioned in recess 102 for automatic needle pickup and insertion in package tray as described hereinbelow.

Needle pockets 97 are needle size specific. The recess configuration in needle pocket 97 will generally fit a narrow range of needle sizes. Quick changeover of the needle feed system to another size needle is facilitated by a single vertical male threaded stud coincident with the axis 99 illustrated in FIG. 18, which is engaged by female threaded knob 116, which, when removed, permits rapid removal of needle wheel 98 and substitution of another with different sized needle pockets mounted therein. Pilot pin 117 assures angular registration of substitute needle wheels. Continued incremental clockwise rotation of needle wheel 98 will cause needle pocket 97, containing a needle therein, and the suture trailing end pulled thereby, to advance from the 12 o'clock position nearest the operator 63 to the 6 o'clock position furthest from the operator. Suture displacement pin 107 is positioned so that, during this rotational sweep, suture trailing end 29 is held radially outward from the periphery of needle wheel 98 as it is pulled from bundle tensioner 67. At about the 4 o'clock position, as illustrated in FIG. 18, a suture displacing device 119 plunges roller 120 over the span of suture strand 118 between adjacent slides 106 and descends vertically with sufficient stroke to form a downward loop in suture 118, fully withdrawing the trailing end of suture 118 out of bundle tensioner 67, thereby avoiding tangles that can occur in the suture bundle if an excessive number is being withdrawn at the same time.

Figure 23:
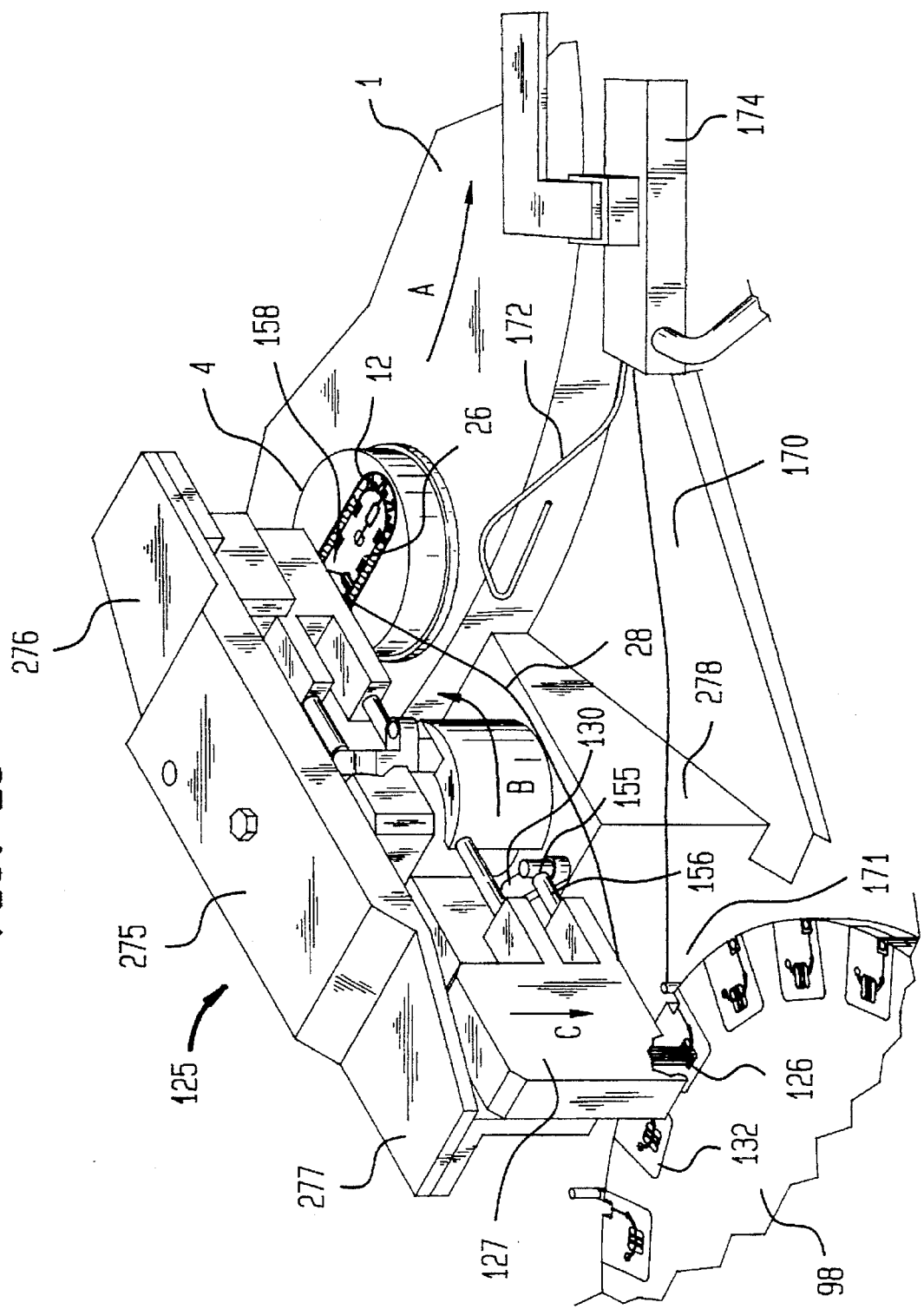
FIG. 23 is an isometric illustration of the transfer arm assembly.
Figure 24A:
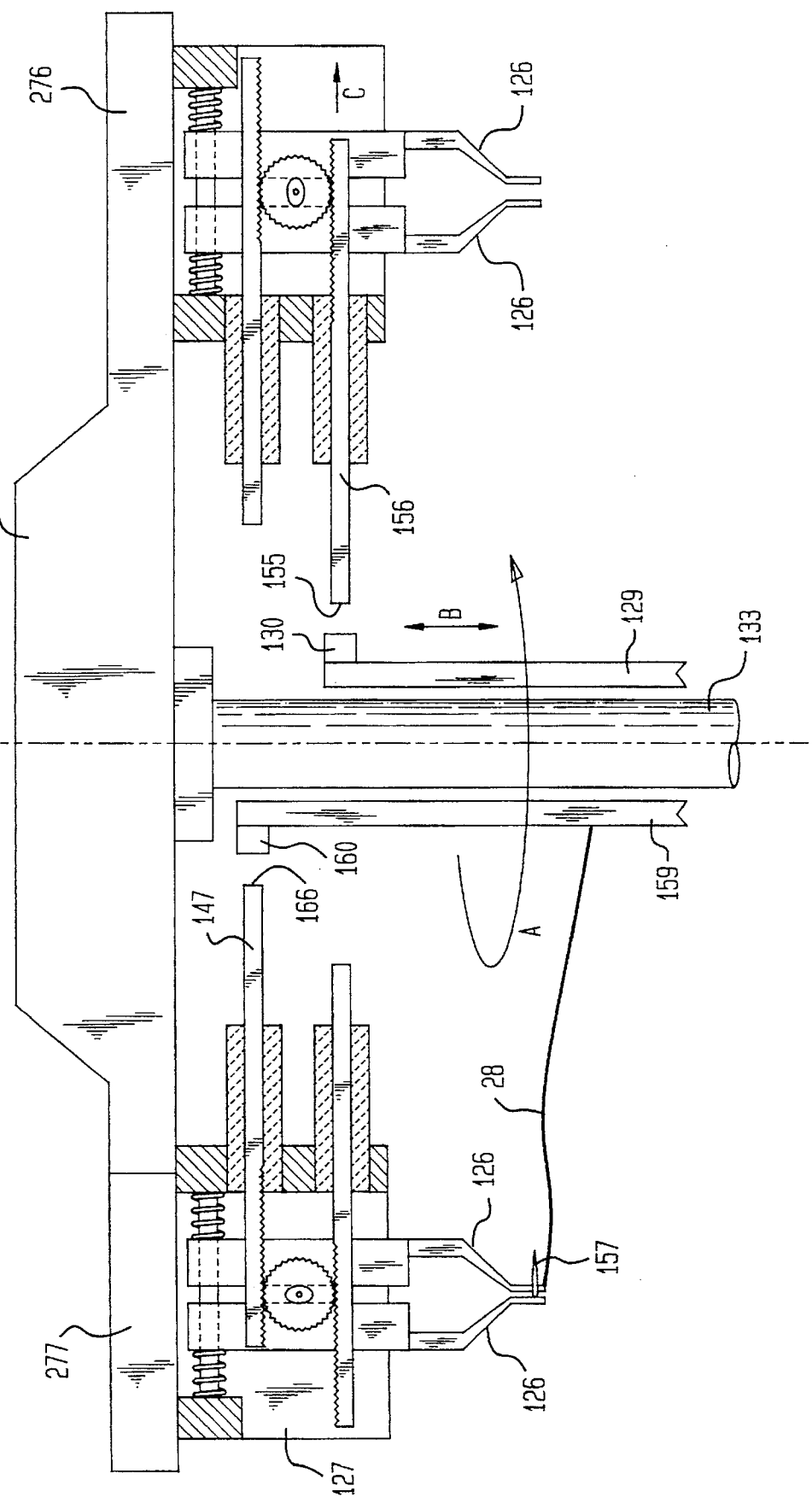
FIGS. 24A, B, and C illustrate elevation views of successive steps in the operation of the transfer arm's internal mechanisms.

As illustrated in the isometric view of FIG. 23, and the elevation view of FIG. 24A, a transfer bar assembly 125 is configured to transfer needles with attached sutures from needle wheel 98 to tray 12 in tool nest 4 in machine station 2.

Transfer bar assembly 125 is comprised of a flat horizontal member 275, with two identical end assemblies 276 and 277, fixedly attached to vertical shaft 133, which is the controlled motion output shaft of a 180° transmission 278 mounted to the machine frame therebelow. Shaft 133 rotates counterclockwise about vertical axis 324, in 180° increments which are phased in time so that the dwell or rotationally stationary portion of the cycle is synchronized with the similar dwell period for main turret 1 and needle wheel 98. Transmission 278 has a vertical motion capability which imparts a vertical stroke of raising and lowering within the rotational dwell period for each 180° rotary index, thereby producing a motion referred in the automation industry as "pick-and-place" for transfer assembly 125. Each end mechanism of transfer bar assembly is comprised of a housing 127 and a needle gripping jaw assembly 126 depending therefrom. The efficiency of the double ended design of transfer bar assembly 125 produces a high machine production rate. A set of horizontal push-rods extends from housing 127 inwardly, radially toward vertical shaft 133, which are operatively connected within housing 127 to open or close jaws 126.

Figure 25A:
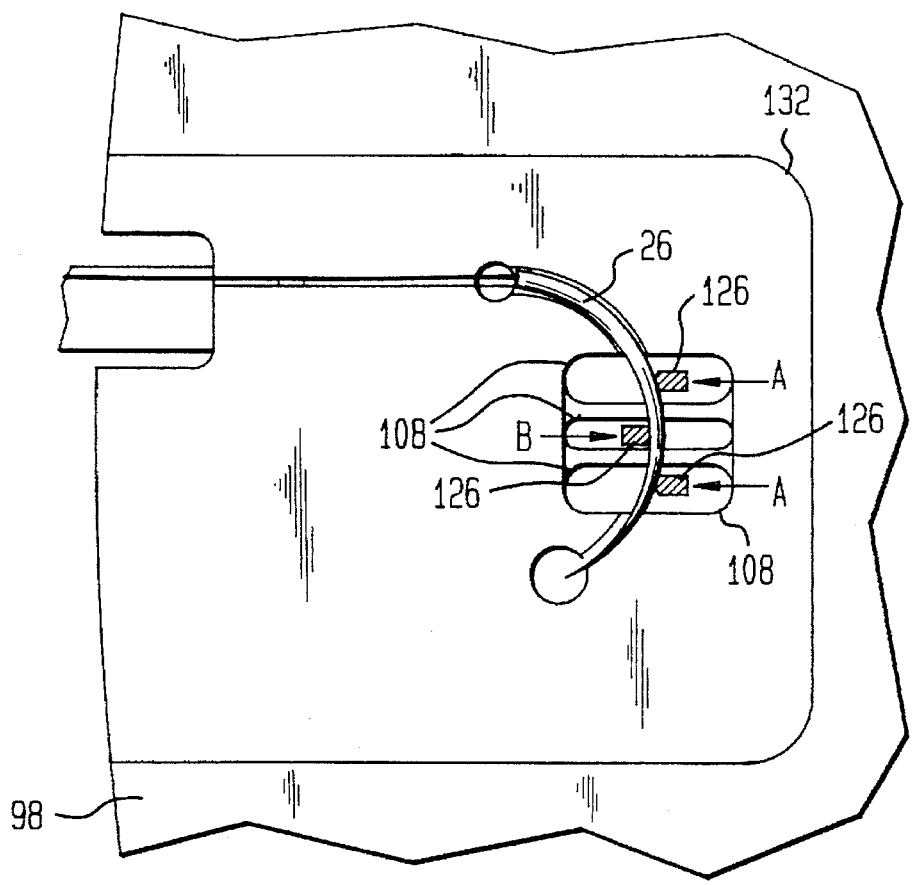
FIGS. 25A and 25B, illustrate the clamping of needle grippers on the needle.
Figure 25B:
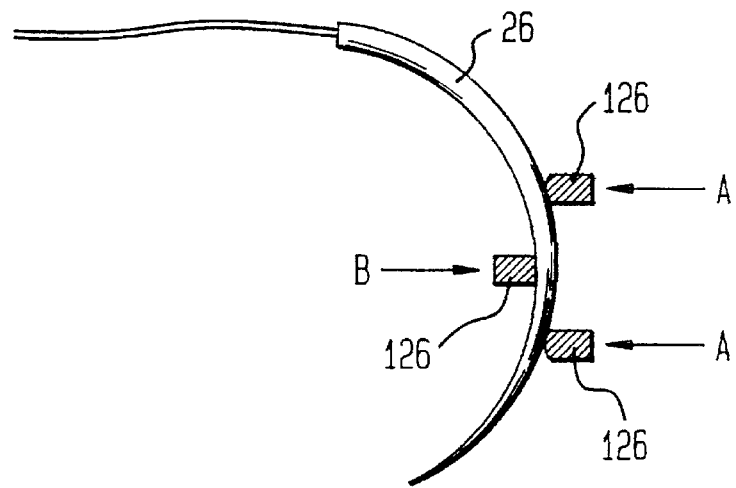
Figure 27:
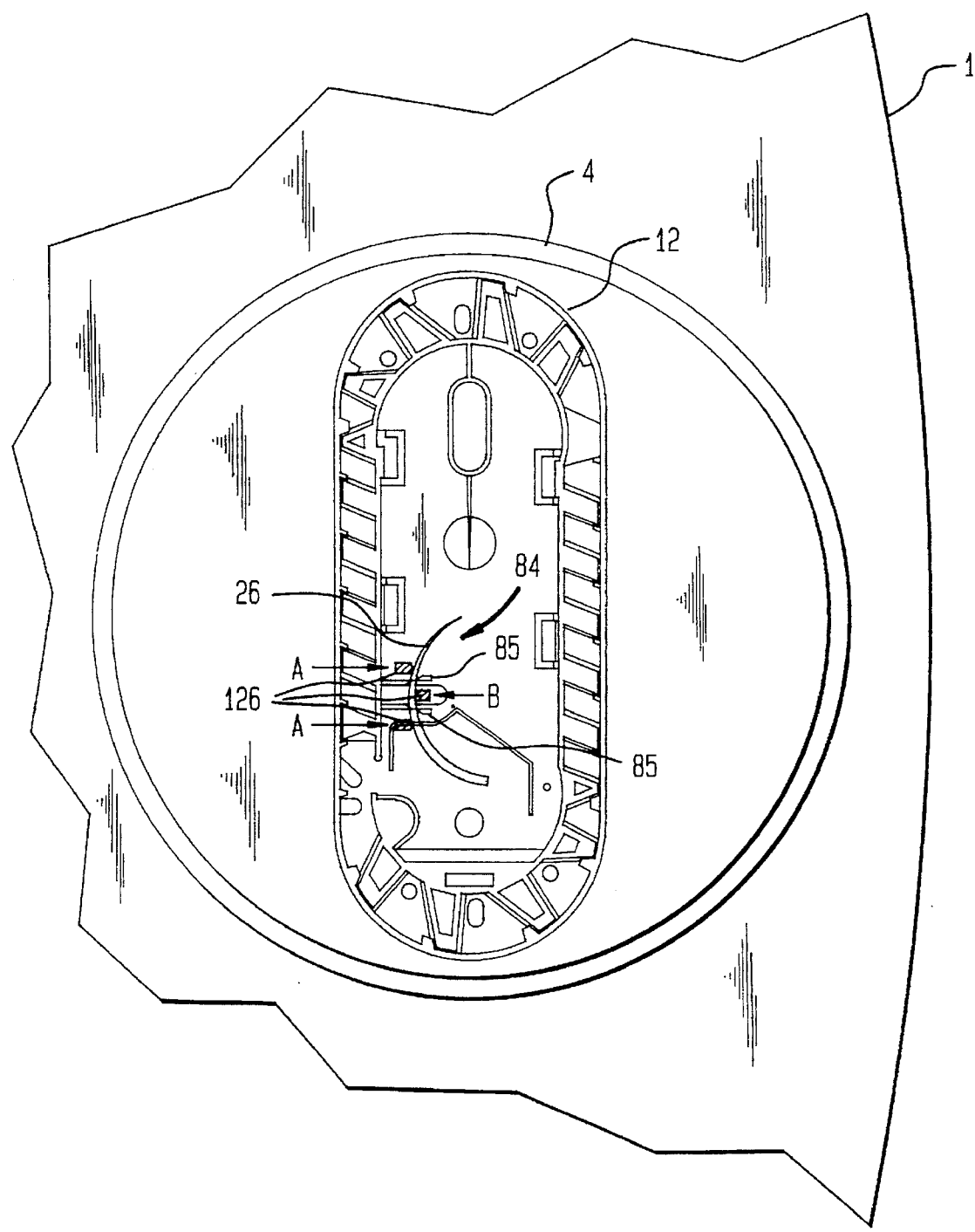
FIG. 27 illustrates the positioning of needle grippers in the package tray.
Figure 28:
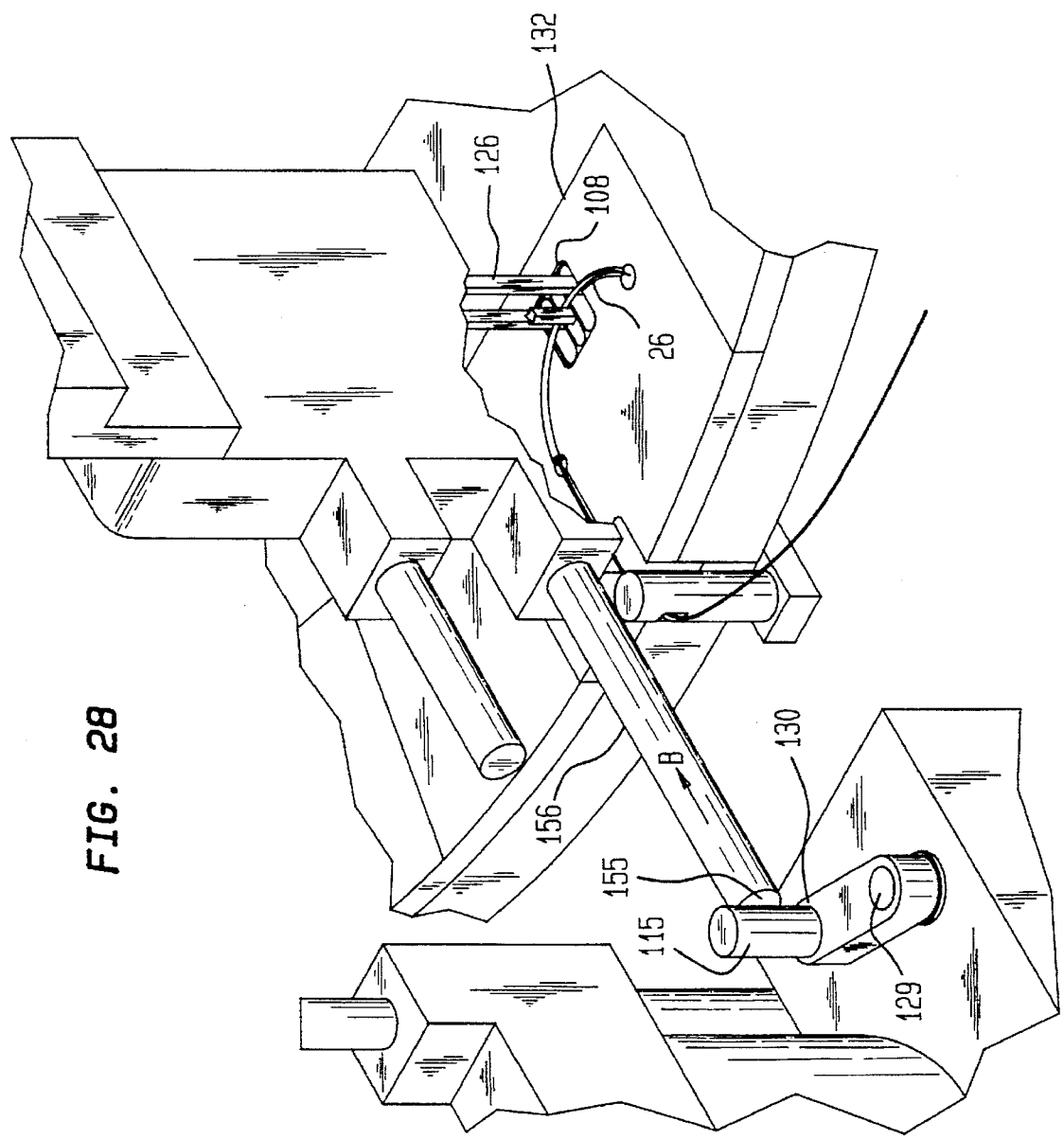
FIG. 28 illustrates; an isometric view of the needle grippers entering a needle pocket in the needle wheel.

Referring to FIGS. 23 and 27, in the operative machine production cycle, transfer bar assembly 125, following the motion in the foregoing description, positioned at a rotationally dwelled position, is configured to cause needle grippers 126, to descend, enter gripper recess grooves 108 in needle pocket 132, grip needle 26, and raise it vertically out of grooves 108. FIG. 25A illustrates a sectioned view of needle grippers 126 that have entered grooves 108 and closed, in the directions of arrows A and B, so as to engage needle 26 with a straddling three point grip as illustrated. FIG. 25B illustrates the three needle grippers 126 after vertical removal of the needle 26 from the needle wheel pocket 132, continuing to impart engaging forces in the directions of A and B, thereby suspending the needle 26 in space as it is transported by the transfer bar for insertion in the package tray needle park.

Figure 26A:
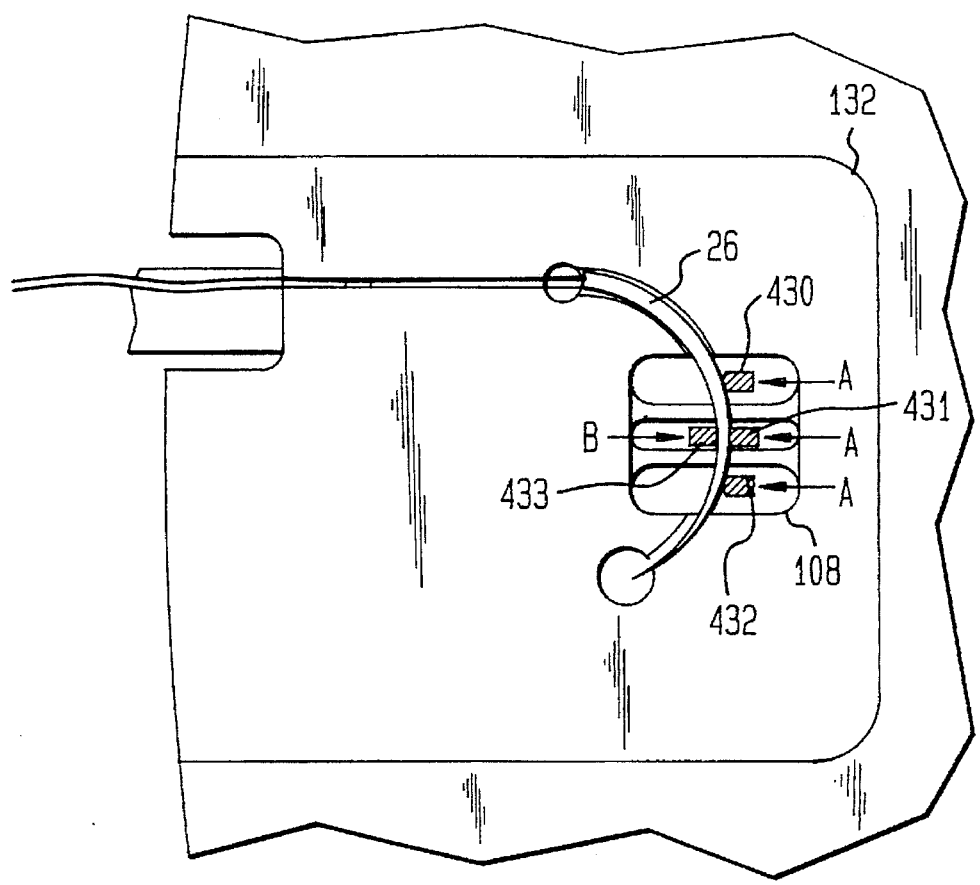
FIGS. 26A, B, C, and D, illustrate the construction and operation of an alternate design for the needle gripper fingers.

An alternative to the three point needle gripper design described hereinabove is illustrated in FIGS. 25A, B, C, and D. Referring to FIG. 26A, the alternate design is comprised of three outer fingers 430, 431, 432, mounted integrally on and configured to move with a single mounting block (gripper block 135 illustrated in FIGS. 24B and C) that is displaced in the direction of arrows A to effect closure on the needle 26. Similarly, a central inner finger 433, integral with a second mounting block (gripper block 145, illustrated FIGS. 24B and C), positioned to oppose the center outer finger 431, is displaced in the direction of arrow B upon closure. The needle 26 is clampingly engaged by the foregoing simultaneous motion of outer and inner gripper fingers in the directions of arrows A and B respectively.

Figure 26B:
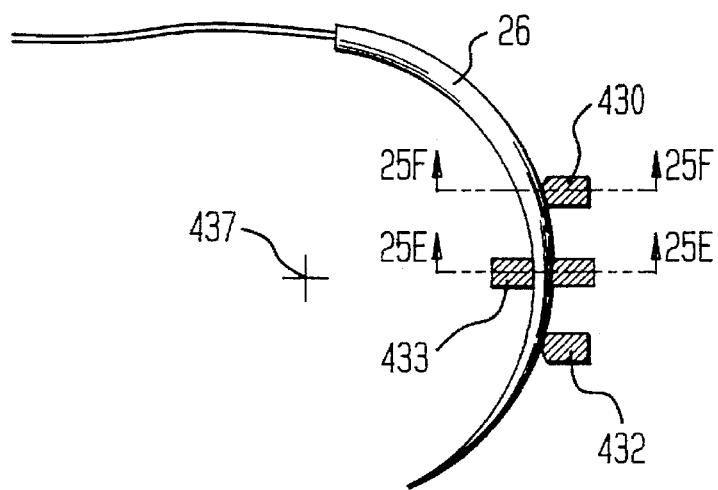
Figure 26C:
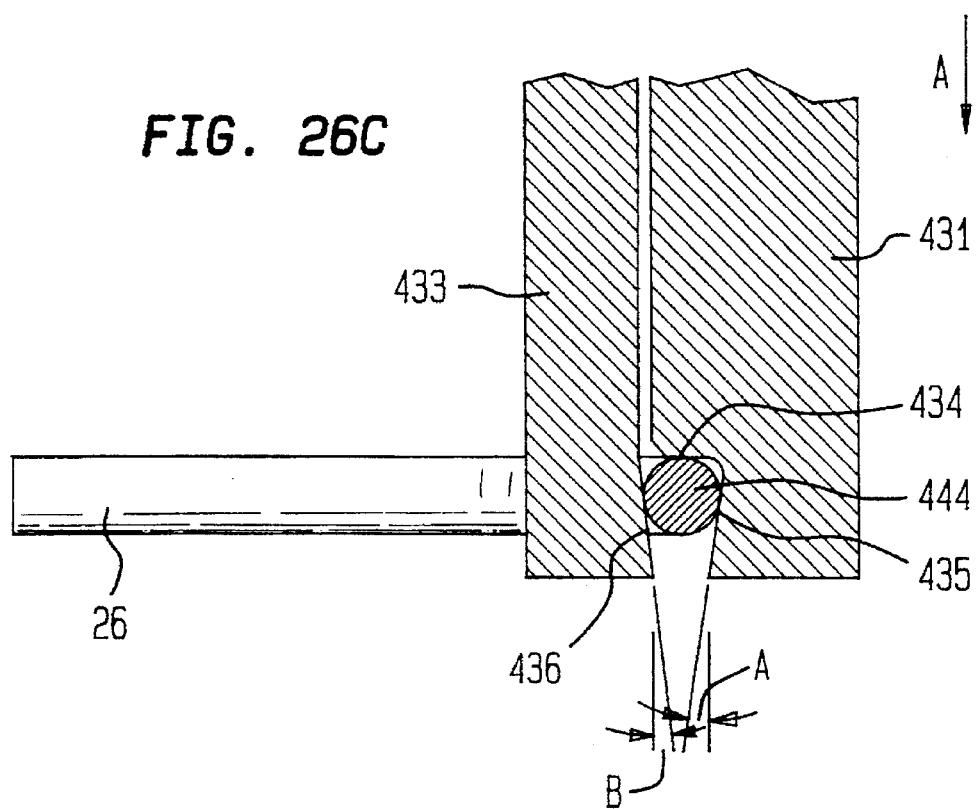

FIG. 26B and section views 26C and 26D taken therefrom illustrate the function of the gripper fingers with regard to specific profiles at the point of needle contact therewith. Referring to FIG. 26C, the central gripper fingers 431 and 433 have opposing surfaces 435 and 436 thereon that apply the gripping force clampingly to the cross sectional diameter 444 of the needle 26 therebetween. Negative draft angles A and B provide a slightly upward resultant force, thereby biasing the needle 26 against the horizontal surface 434 in the profile of the outer central gripper finger 431. The horizontal surface 434 also functions to impart force on the needle 26 as it is driven downwardly to plastically deform the package needle park (not shown) by movement of the gripper assembly in the direction of arrow A. Security of the grip is further enhanced if needle 26 has flattened diameter surfaces at this point of gripper contact.

Figure 26D:
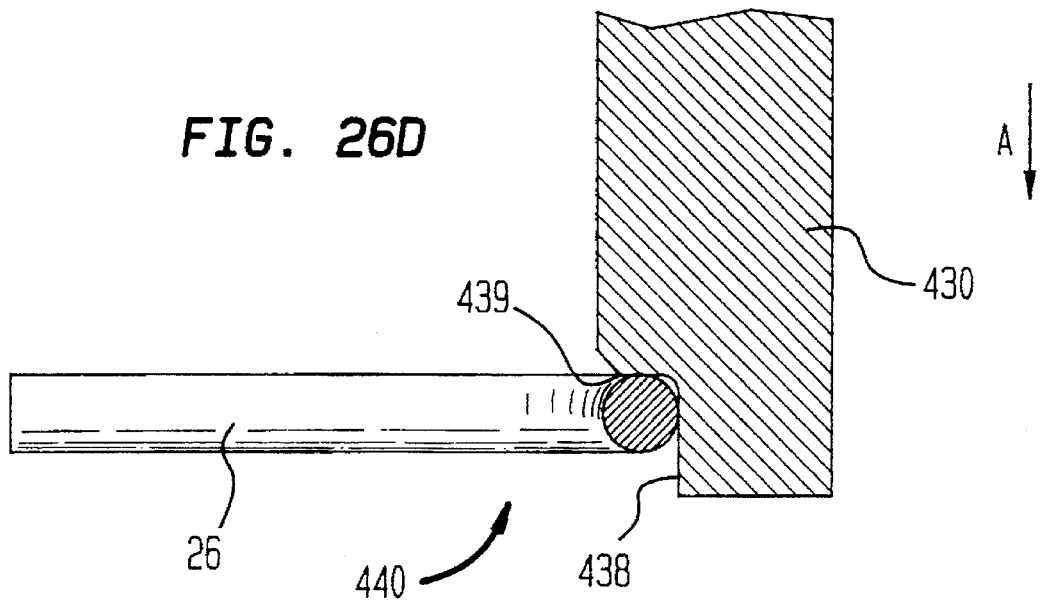

FIG. 26D illustrates the functional elements of the gripper profile 440 for side finger 430, finger 432 being identical thereto. Horizontal surface 439 provides a backup support surface to resist the downward force on the needle 26 as it is driven into the package needle park by movement of the gripper assembly in the direction of arrow A. Vertical surface 438 stabilizes the needle 26 with regard to angular rotation about the vertical axis of needle curvature 437, thereby assuring precise location of the needle 26 when clampingly engaged in the needle gripper fingers.

The motion path of transfer bar assembly 125 is configured to lift needle grippers, and needle 26 therewith, vertically, and complete a 180° rotational index indicated by arrow B, in FIG. 23, transporting needle 26 and placing it into tray 12 on tool nest 4.

The operational sequence of transfer bar assembly 125 is described in more extensive detail hereinbelow and illustrated in FIGS. 24A, 24B, and 24C which are directed toward the operational aspects of the mechanisms therein.

FIG. 24A illustrates the transfer bar assembly 125 and associated mechanisms in elevation view. The actuation of needle gripper 126 is illustrated in FIG. 24B and FIG. 24C.

Figure 24B:
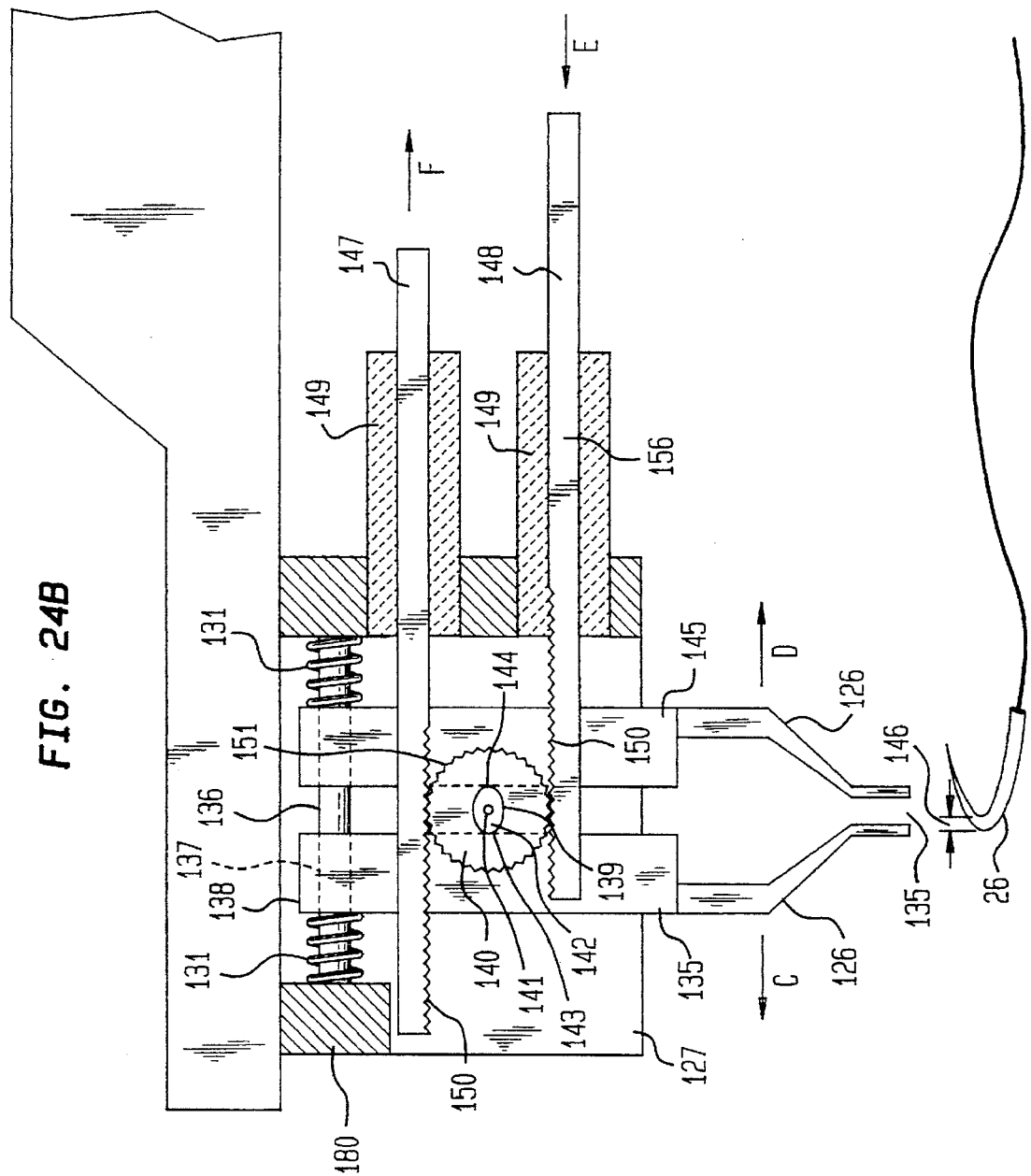
FIGS. 24D and 24E illustrates an alternative design for the transfer arm's internal mechanisms.
FIG. 24F illustrates still another alternative design for the transfer arm's internal mechanism.
Figure 24D:
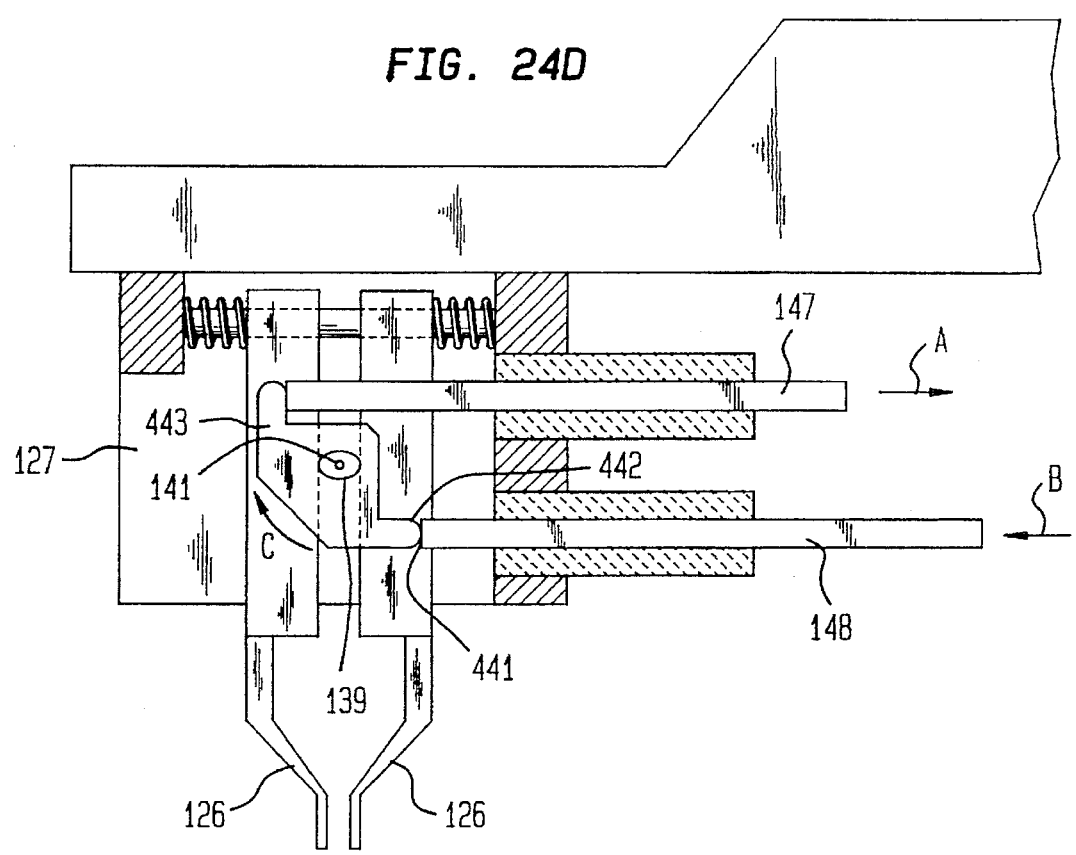
Figure 24E:
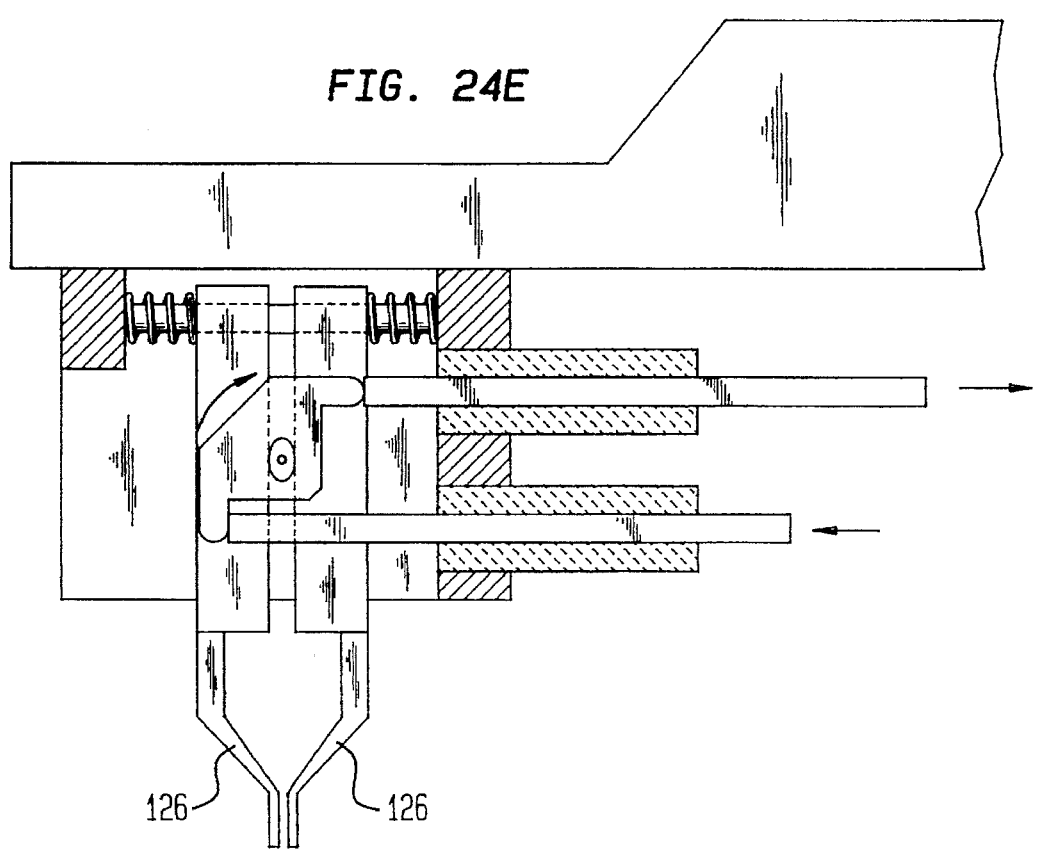

The needle grippers are open in FIG. 24B, as indicated by gap 135 therebetween. Gripper block 135 is slideably mounted on fixed horizontal shaft 136, guided in precise lateral motion by a close fitting horizontal slidable bore 137 in the gripper block upper end 138. Gripper block 135 is spring loaded toward the closed position by compression spring 131 which imparts force between fixed block 180 and gripper block upper end 138. The resultant force biases block 135 and gripper 126 attached thereto in a closed direction, opposite to arrow C. The arrangement for gripper block 145 is a mirror image of block 135, the above description applying there also, but in the reverse direction. The grippers in FIG. 24B are displaced to the open position, in opposition to the force imparted by springs 131, by cam 139, integrally attached to cam gear 140, which is rotationally mounted on shaft 141 which is fixedly attached to needle gripper housing 127. FIG. 24B illustrates the instance in which lobe 142 of gripper cam 139 is bearing against inner wall 143 of gripper 135, displacing it in the direction of arrow C (open). An equal displacement in the opposite direction by a similar but mirror image of the mechanism described above, for gripper 145 is driven by cam lobe 144 displacing gripper block 145 in the direction of arrow D. Grippers 126 are opened sufficiently to receive, without interference, the wire diameter width 146 of surgical needle 26 therebetween. The operating force on needle grippers 126 is positive cam force to open, and spring force to close, thereby allowing the grippers to close with a force that will yield to accommodate different needle sizes without adjustment.

Cam gear 140 is driven in rotation by two push-rods, 147 and 148, which for open and close grippers 126 respectively. Push-rods 147 and 148 are slideably held in bushings 149, so positioned that rack portions 150 thereon engage with gear teeth 151 on gear 140. From the open condition represented by FIG. 24B, grippers 126 may be closed by lateral displacement of push rod 148 to the left in the direction of arrow E, causing the rack teeth 150 on push rod 148, to impart sufficient clockwise rotation to gear 140 that gripper cam 139 rotates from a maximum to a minimum rise angular position with respect to gripper blocks 135 and 145, as shown in FIG. 24C. Accordingly, gripper springs 131 cause gripper blocks 135 and 145 to slide on rod 136 symmetrically toward each other, causing corresponding closure of gripper tips 126 on surgical needle 26. Gripper closure is reversed (opened) by lateral leftward displacement of push rod 147 represented by arrow G, resulting again in the above actuation, but in the reverse direction to the position represented by FIG. 24B.

Two alternative designs to accomplish this same function are described in FIGS. 24 D and E and 24F. FIG. 24D illustrates a bell-crank 443 and jaw operating cam 139 attached thereto, pivotally mounted on a horizontal shaft 141 fixedly attached to the needle gripper housing 127. The operative sequence to close grippers 126 on a needle (not shown) is initiated by horizontal displacement of the closing pushrod 148 in the direction of arrow B, thereby causing rod face 441 to bear against the rounded bell-crank arm 442. The bell-crank 443 and cam 139 attached thereto will rotate on shaft 141 in the direction of arrow C, to the position illustrated in FIG. 24E, illustrating the resulting closed position of grippers 126. The grippers are subsequently opened by horizontal displacement of opening pushrod 147 to the left, opposite to arrow A, FIG. 24D, thereby causing the mechanism to operate in the reverse direction.

Figure 24F:
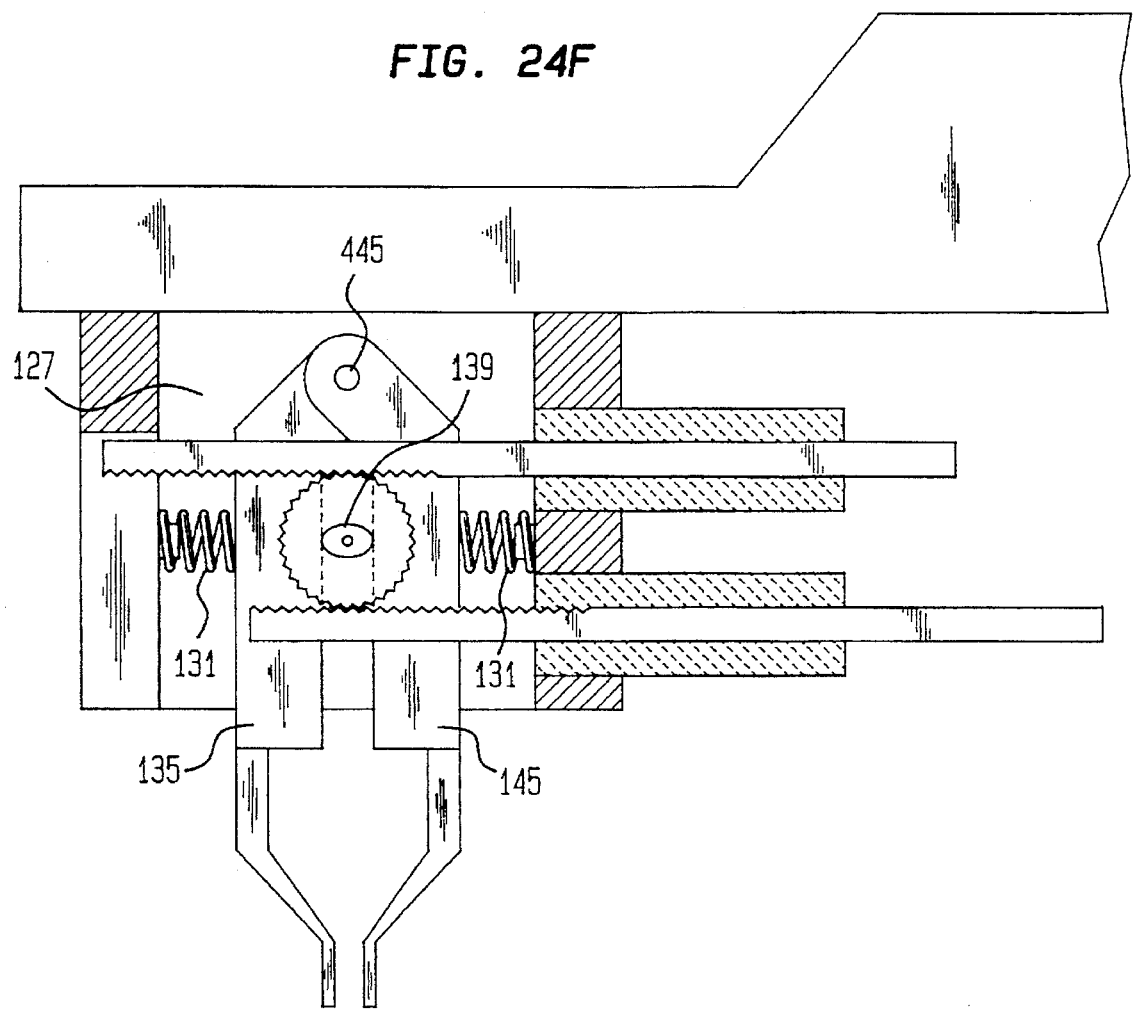

Still another alternative design which relates to the means of mounting the gripper blocks 135 and 145 is illustrated in FIG. 24F, in which blocks 135 and 145 are slideably mounted on shaft 136 and the aforementioned gripper blocks are pivotally mounted on a horizontal shaft 445 that is fixedly mounted in the mechanism housing 127. Closing springs 131 are located to impart a constant closing force on the gripper blocks 135 and 145, which are held open by the operating cam 139 as described hereinabove.

Referring to FIG. 25A, preparation for pickup of needle 26 in needle pocket 132 on needle wheel 98 is achieved after downward motion of transfer bar assembly 125 inserts open gripper tips 126 into needle pocket grooves 108, thereby straddling the mid length section of needle 26 bridged thereacross. At that point of the cycle, a vertical closing rod 129 illustrated in FIG. 24A, may be driven in angular rotation from a cam actuator in the machine base below (not shown), rotating sufficiently to cause the tip of radius arm 130 to contact the end face 155 of closing push rod 156 and displace it laterally in the direction of arrow C, thereby closing grippers 126 on needle 26 therebetween by actuation of the gripper closing mechanism as described above.

Transfer bar 125 may then be raised in the direction of (arrow B), rotated counterclockwise 180° (arrow A) to carry needle 26 clamped in grippers 126, with suture 28 trailing therefrom, through space as illustrated in FIG. 23, and lowered over package tray 12 on nest 4. Transfer bar 125 and grippers 126, moving therewith, may then be moved downward and insert needle 26 into the needle park 84, illustrated in FIG. 27, imparting a force sufficient to plastically deform blades 85, 86 of needle park 84, into gap 87, in tray 12 as previously described with respect to FIGS. 4 and 5.

As illustrated in FIG. 24A, the lateral displacement of push-rod 147, for opening the gripper may be achieved by rotation of vertical opening rod 159 causing radius arm 160 to displace opening push rod 147 by imparting force on face 166. Transfer bar 125 is then ready for a vertical upward stroke as illustrated by arrow B.

Station (III)

Figure 31:
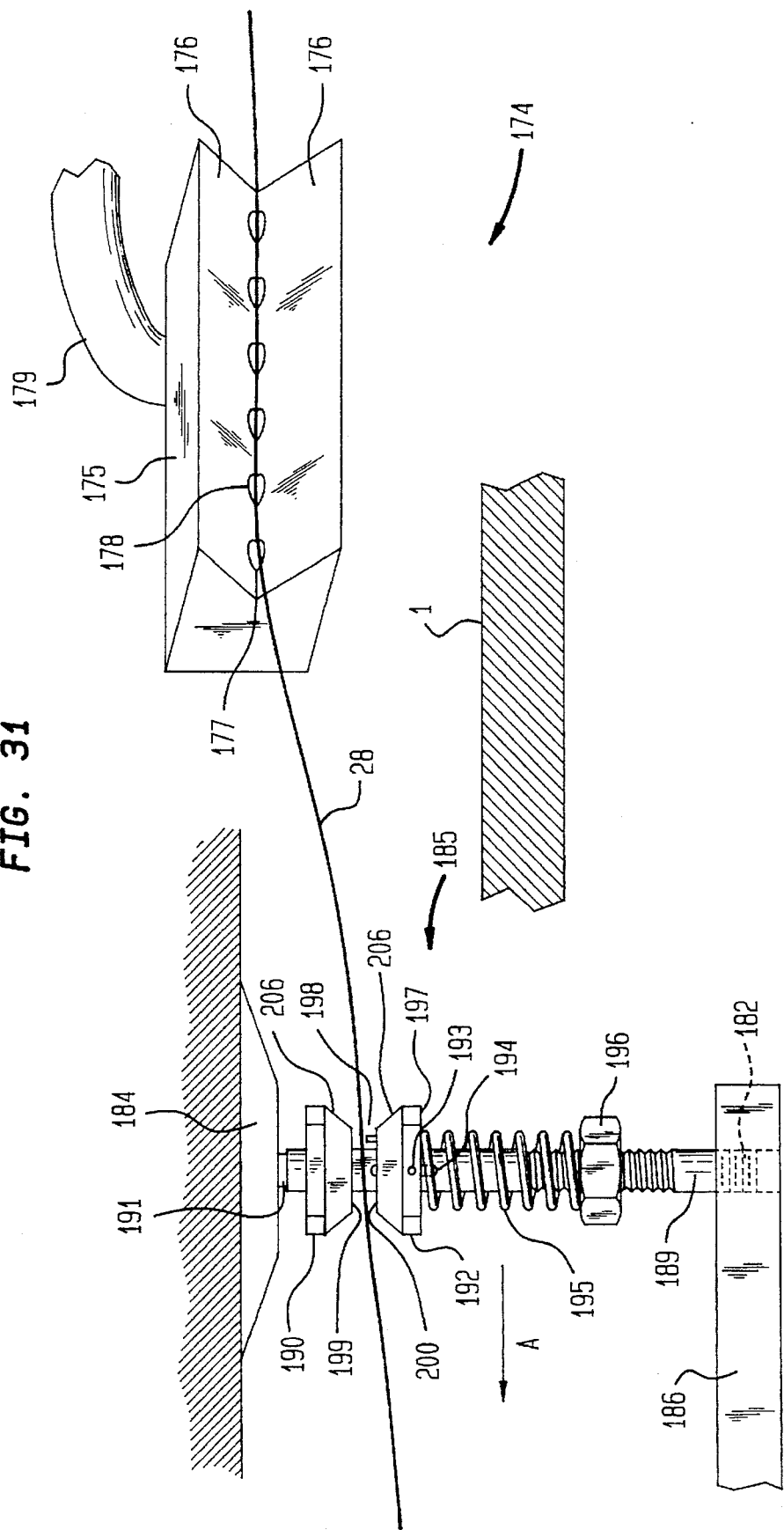
FIG. 31 illustrates an elevation view of the post tensioner, the stationary cam, and vacuum tensioner.

The operation of Station III is first described with reference to the suture handling structures which receive the free end of the suture at station II and provide for controlled passage thereof to station III. Referring to FIG. 23 illustrating machine station II, suture guide 172, is fixedly attached to the frame of the machine, and configured to guide the suture 28 into vacuum tensioning device 174 of machine station III. FIG. 31 illustrates a view from the center of turret 1 looking radially outward, toward machine station III. Tension device 174 consists of a hollow body 175, intersecting planar surfaces 176 to present a "V" shaped longitudinal entry target for the suture, the line of intersection thereof 177 being collinear with the entrance ports of a plurality of vacuum holes 178 arranged in a linear array. Vacuum holes 178 are ported to an internal chamber within body 175 connected to a vacuum source by hose 179. Vacuum holes 178 are sized sufficiently small to resist inducting a suture thread 28 positioned in slot 177 into the hole itself, but sufficiently large to create a volume of airflow and resultant force sufficient to draw suture 28 into slot 177 when it is brought within reasonable proximity thereto, and to impart a consistent, gentle resistance to movement of the suture and resultant tension therein as it is drawn axially through the device.

Figure 10:
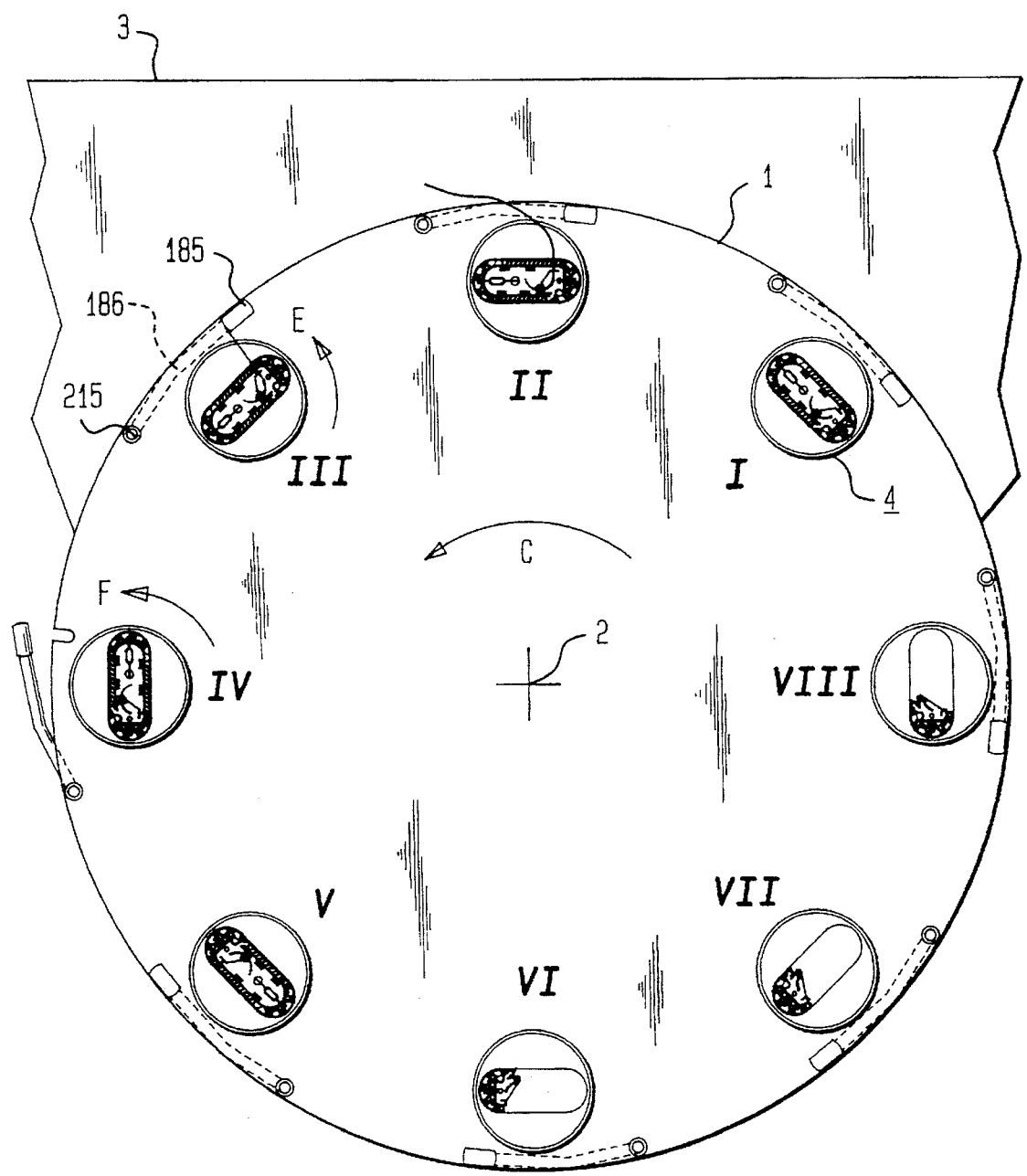
FIG. 10 illustrates a plan view of the main machine indexing turret with tool nests thereon.
Figure 29:
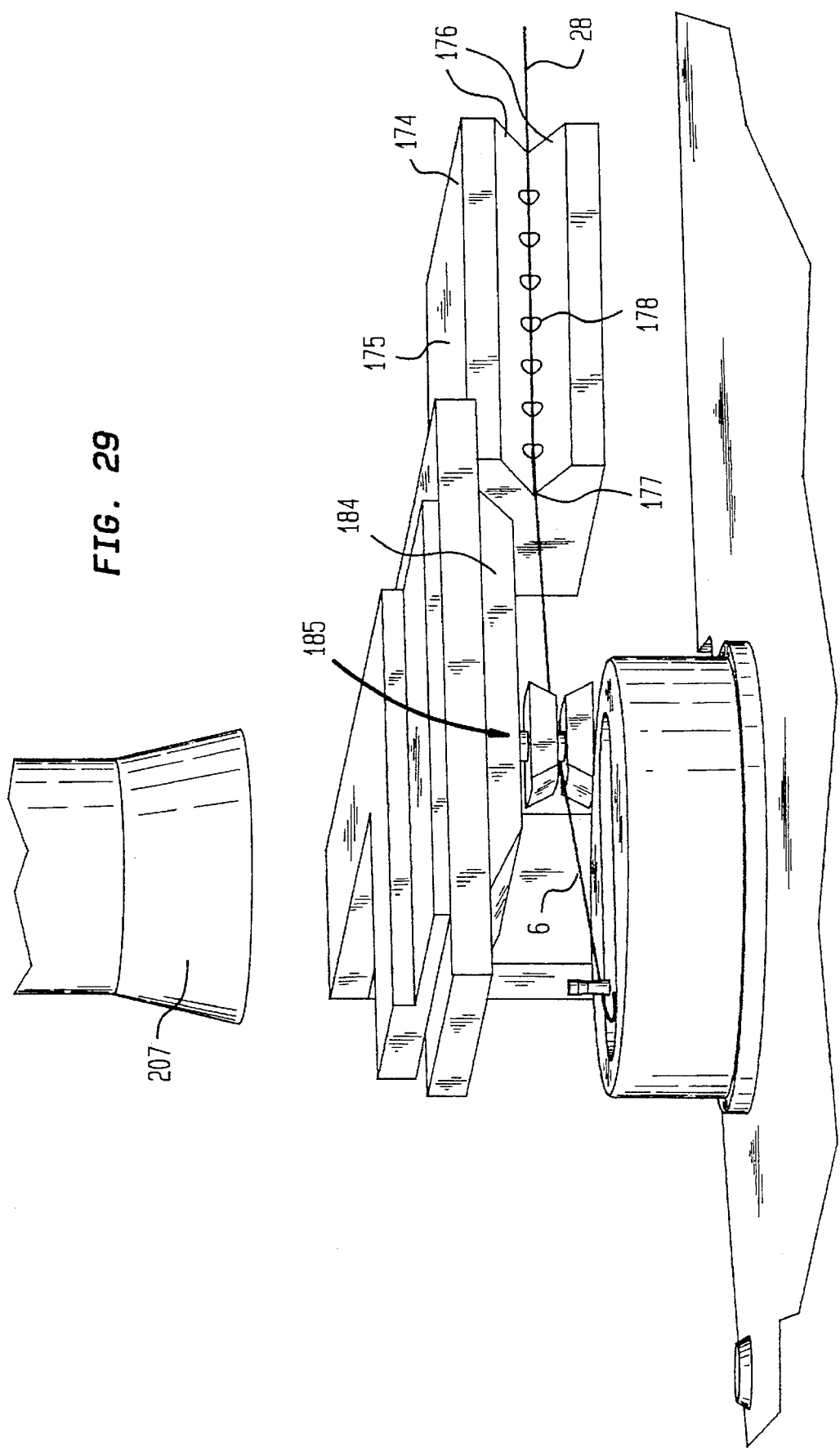
FIG. 29 illustrates an isometric view of machine station III.

Station III further includes a stationary cam 184 that opens and closes post tensioner 185, as illustrated in FIGS. 29 and 31. Post tensioner 185 provides suture tension and entry angle control for the winding operations performed on the package while in each tool nest 4. One post tensioner is located for each tool nest on turret 1 in the relative proximity indicated in FIG. 30. Tensioner arm 186, mounted pivotally by vertical pin 187 to turret 1 provides support for post tensioner 185, which is fixedly attached to the trailing end of arm 186 by a vertical threaded hole 182. The physical arrangement of post tensioners 185 relative to turret 1 is also illustrated in FIG. 10.

As illustrated in FIG. 31, post tensioner 185, is comprised of a center tubular mounting post 189, and an inverted top cone 190 fixedly attached thereto, a solid rod release plunger 191 slidingly mounted in tubular post 189, a bottom cone 192 assembled slideably on post 189 and fixedly attached to plunger 191 by cross pin 193 pressed therethrough. Cross pin 193 extends from bottom cone 192 through vertical clearance slot 194 and is pressed through the diameter of release plunger 191 so that these elements act mechanically as one integral unit. Spring 195, imparting a vertical compression force between the adjusting nut 196 and the bottom face 197 of bottom cone 192 produces an upward bias tending to close the gap 198 between cones 190 and 192, consequently raising release plunger 191.

Figure 32:
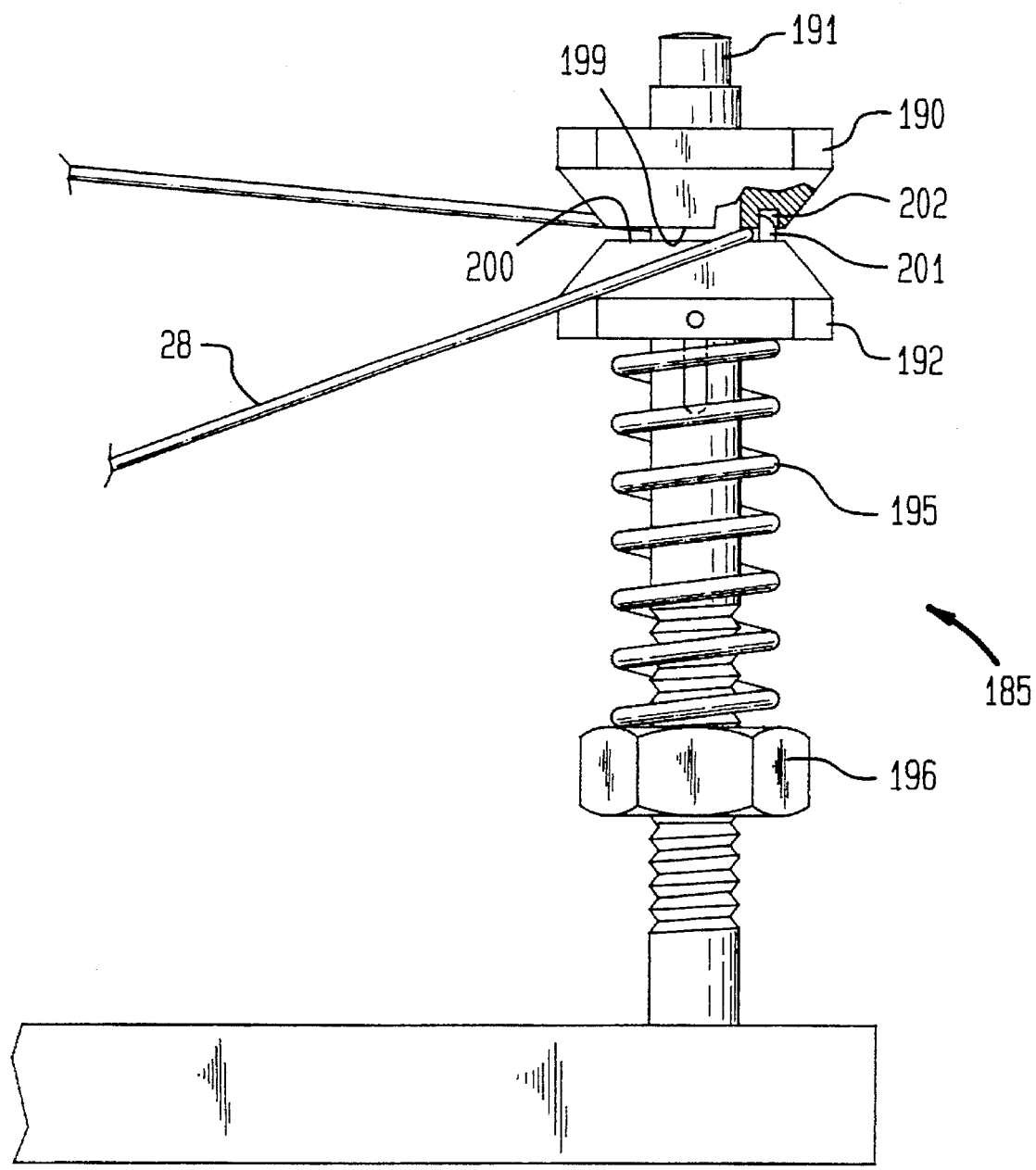
FIG. 32 illustrates an enlarged elevation view of the post tensioner.

FIG. 31 also illustrates the function of stationary cam 184 to exert a downward force on release plunger 191 as turret 1 indexes nest 4 toward station III, thereby allowing suture 28, under tension produced by vacuum tensioner 174 to enter between inner faces 199 and 200 of upper and lower cones respectively. Stationary cam 184 is positioned at the periphery of turret 1, such that plunger 191 is depressed and released before turret 1 indexes to the dwell position at machine station III. After turret 1 advances tensioner 185 beyond stationary cam 184, the force imparted by spring 195 closes gap 198 and causes faces 199 and 200 to bear on suture 28 with a predetermined amount of friction pre-adjusted by nut 196, as illustrated in FIG. 32.

During the winding segments of the machine cycle, described hereinbelow for machine stations III and IV, suture 28 is drawn slideably through post tensioner 185, by the resisting tensile force determined by the adjusting nut 196 on compression spring 195. A single tooth 201 in the bottom cone 192, extending into recess 202 of top cone 190 prevents suture 28 from migrating out from between the opposing faces 199 and 200 as its trailing length slides therethrough.

Figure 34:
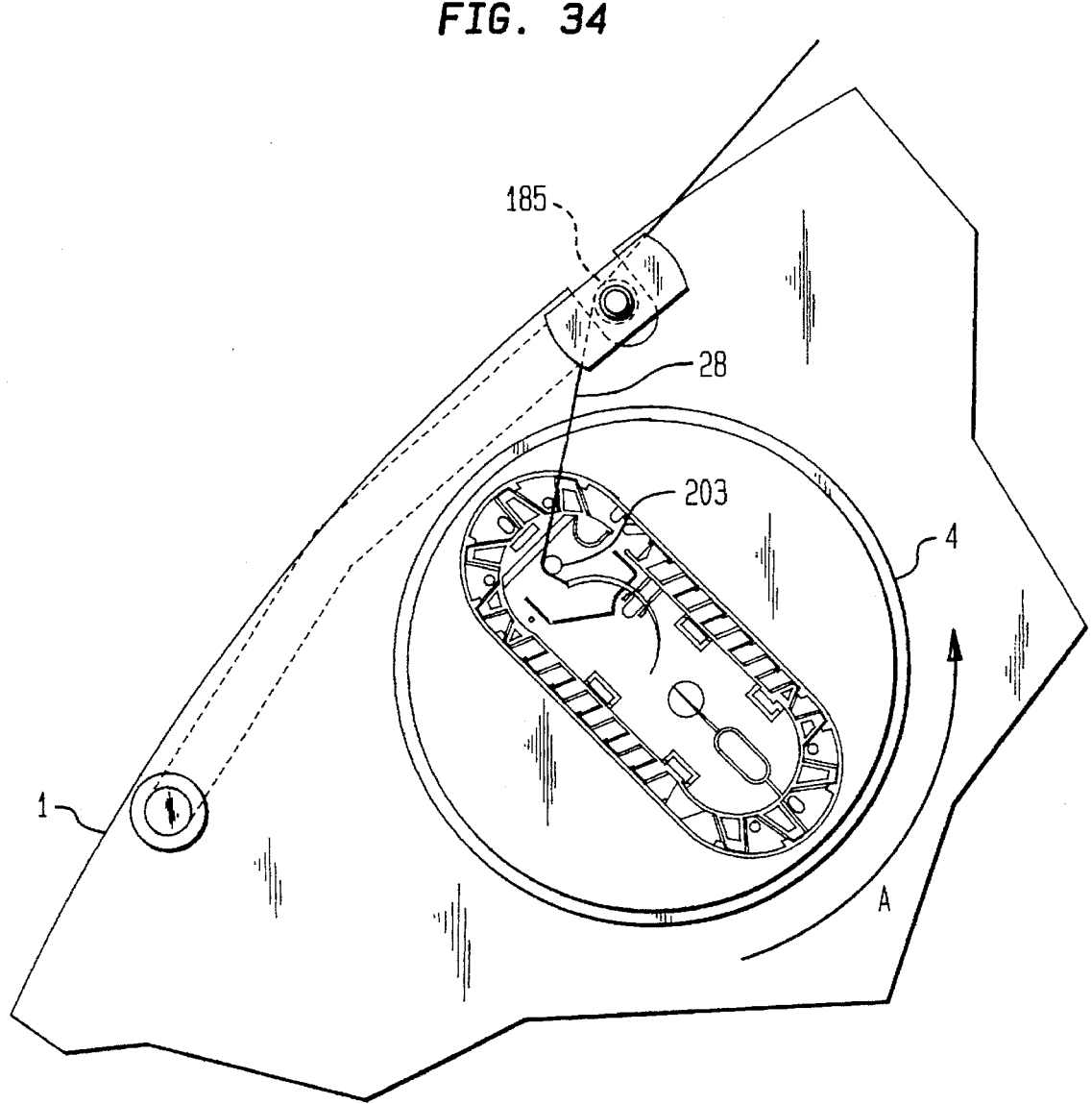
Figure 35:
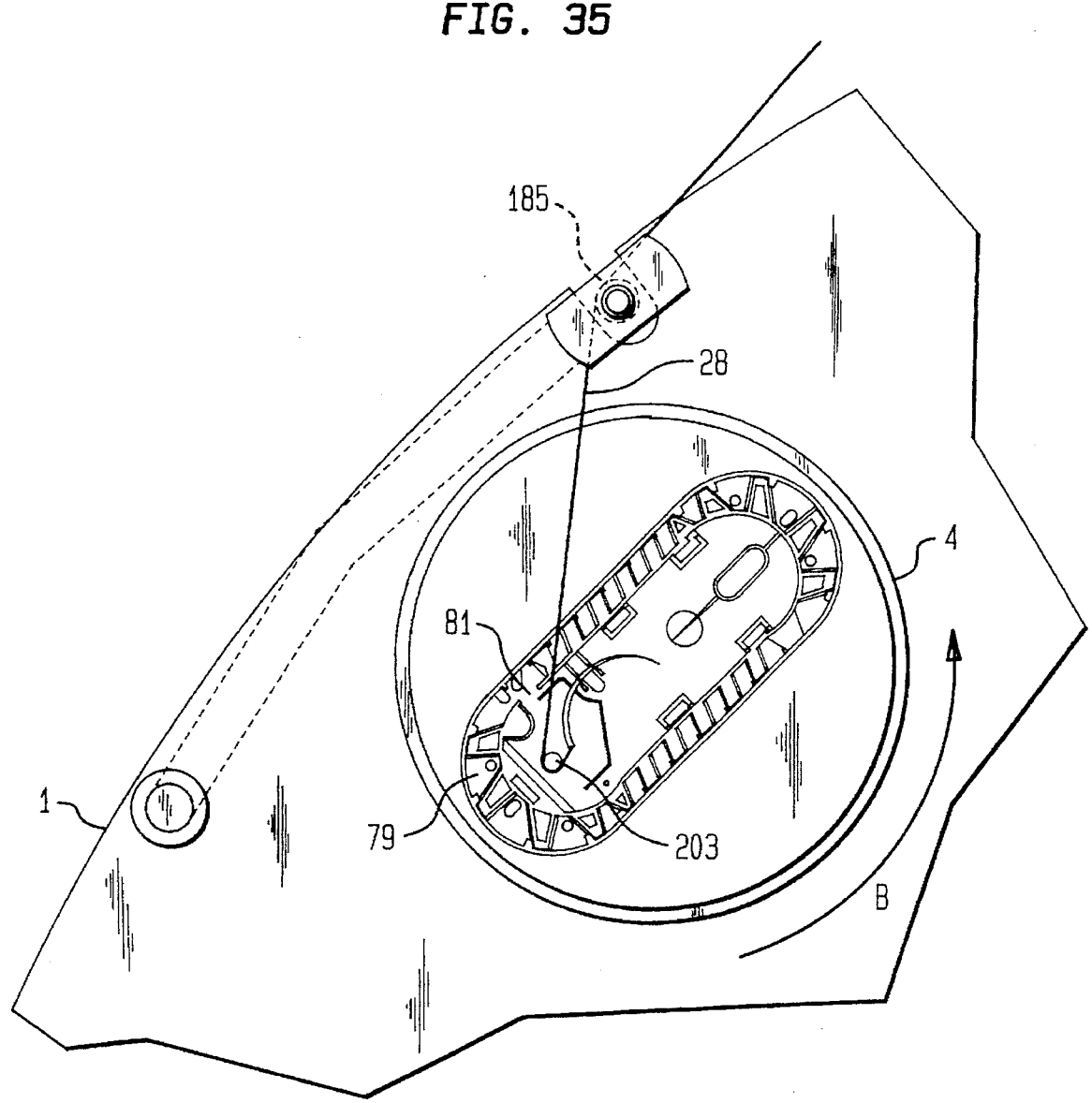

At the dwell position (halt in rotary index motion) of turret 1 at station III, tool nest 4 is positioned over the rotational drive system described and illustrated in the foregoing FIGS. 11A through 13C. Tool nest 4 is rotated 180° counterclockwise in its internal bearings as illustrated progressively in FIGS. 33 through 35 and indicated by arrows A and B, resulting in suture 28 wrapped partially around pilot pin 203 and the path of suture 28 roughly aligned with gap 81 in suture channel 79. Gap 81 is described in detail with respect to FIGS. 2 and 3 and the specification associated therewith. The operation performed at station III, described hereinabove, pre-positions the suture around pilot pin 203 and positioned in gap 81 in the package tray 12 for the winding operation that follows at station IV.

Station (IV)

Figure 36:
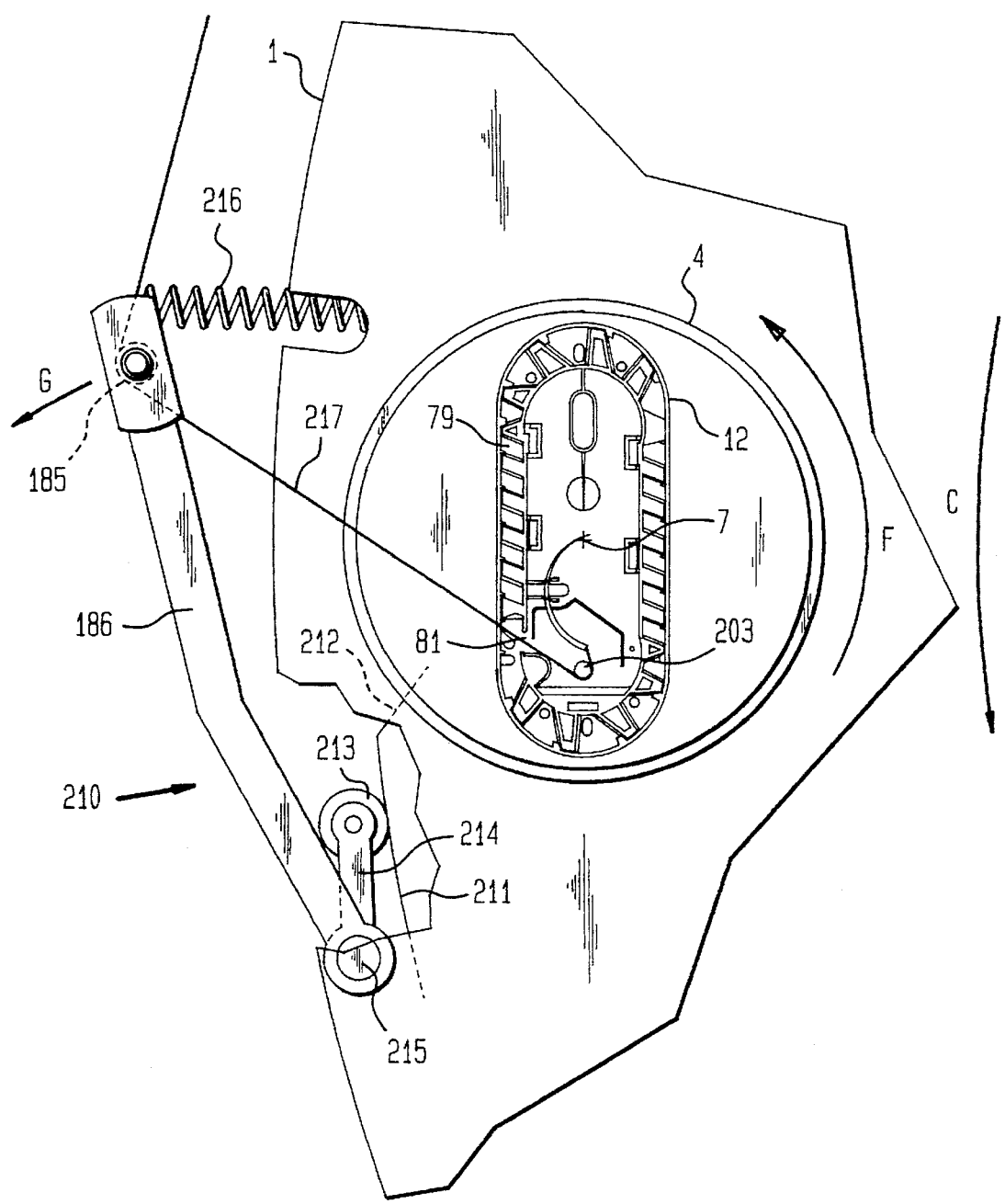
FIG. 36 illustrates the positioning of the suture by the post tensioner at winding station IV prior to winding.

The zipper package winding tooling mechanism is described with respect to FIG. 36, which is a plan view looking down on turret 1, but with the overhanging station hardware removed for visual clarity, nest 4 is positioned by the index of turret 1 in the direction of arrow C into station IV of the package assembly machine, and, upon command of the computer control system, is driven in rotation about vertical nest axis 7 by the nest rotation means previously described for station III and more extensively described with respect to in FIGS. 11 through 14C hereinabove.

A cutaway view, looking through a portion of turret 1, is provided in FIG. 36 which illustrates the attachment and cam displacement means for tensioner arm 186. Stationary cam 211 and associated entrance ramp surface 212 are attached to and positioned on the machine frame such that the dwell position of turret 1 that positions nest 4 for the winding operation in station IV results in cam follower 213 having climbed ramp 212, coming to rest on the rise portion of cam 211, thereby causing an angular displacement of cam follower arm 214 about pivot axis 215, and equal angular displacement of tensioner arm 186 attached thereto. Arm 186 is maintained in contact with cam 211, relative to turret 1, by tension spring 216 attached therebetween. Angular displacement of tensioner arm 186 resulting from the rise of stationary cam 211 displaces post tensioner 185 in the direction of arrow G such that the span of suture strand 217, from tensioner 185 to pilot pin 203 on tool nest 4, forms an angle with respect to molded tray 12 that positions suture span 217 within inner wall gap 81 in suture channel 79. This positioning of suture span 217 into the entry point of package channel 79 is a precondition for closure of the winding station and its associated tooling on tray 12 in preparation for winding rotation.

Referring to FIGS. 4 and 5, the sequence for winding the suture 28 in tray 12 is to simultaneously raise all of the plurality of fingers 78 located peripherally over suture channel 79 hingedly about point 66, to an open position illustrated by dashed outline 86. It is then to insert guiding tools to define a generally flat spiral wind pattern 219 to the plurality of resulting winding loops 220, while applying a vacuum through a plurality of holes 162. Needle 26 is secured during winding to avoid displacement due to suture tension. The front suture loop 82 is guided under shelf 221, and the tool nest 4 is rotated about its vertical axis 7 to complete the wind while maintaining a controlled tension on the suture span pulled into the package as the wind progresses. Completing the winding sequence requires assuring that the suture end tail 29, as illustrated in FIG. 2, is reliably inserted in channel 79, and then positively closing fingers from raised position 86 of FIG. 5, to position 78. The winding tooling is then open and withdrawn from the package so that turret 1 can index tool nest 4 to the next operation in the machine sequence.

FIGS. 37–40B illustrate the operative tooling configured to accomplish the above winding sequence. The winding tooling is in the open position as illustrated in FIG. 37 prior to closing on finger 78 of the plurality of fingers of molded tray 12 attached to channel section 222, (as previously illustrated in FIG. 5). Tray 12 is supported vertically by the underside of finger 78 adjacent hinge as it 66 rests on tips 223 of blades 225. It is also supported laterally by the inner wall 227 of suture channel 79 by registration on the side surface of blade 225. Lower tooling platform 224 is vertically slidable on blades 225 that fit blade slots 209 therein. Blades 225 are supported by and integral with blade base 227, fixedly attached to nest base 226. Springs 228 support the weight of lower platform 224 when the tooling is in the open condition, but deflect to allow it to move downward when the tooling is closed. This makes the tooling compliant to variations in elevation or lack of parallelism of the upper tooling platform 230. As illustrated in FIG. 39A a plurality of ejector pins 229, are slideably captured in holes in base 226 and extend through clearance holes in blade base 227 and platform 224. When displaced vertically from below base 226 by cam actuation (illustrated in FIGS. 60A and B), ejector pins 229 lift tray 12 clear of all tooling.

Figure 38:
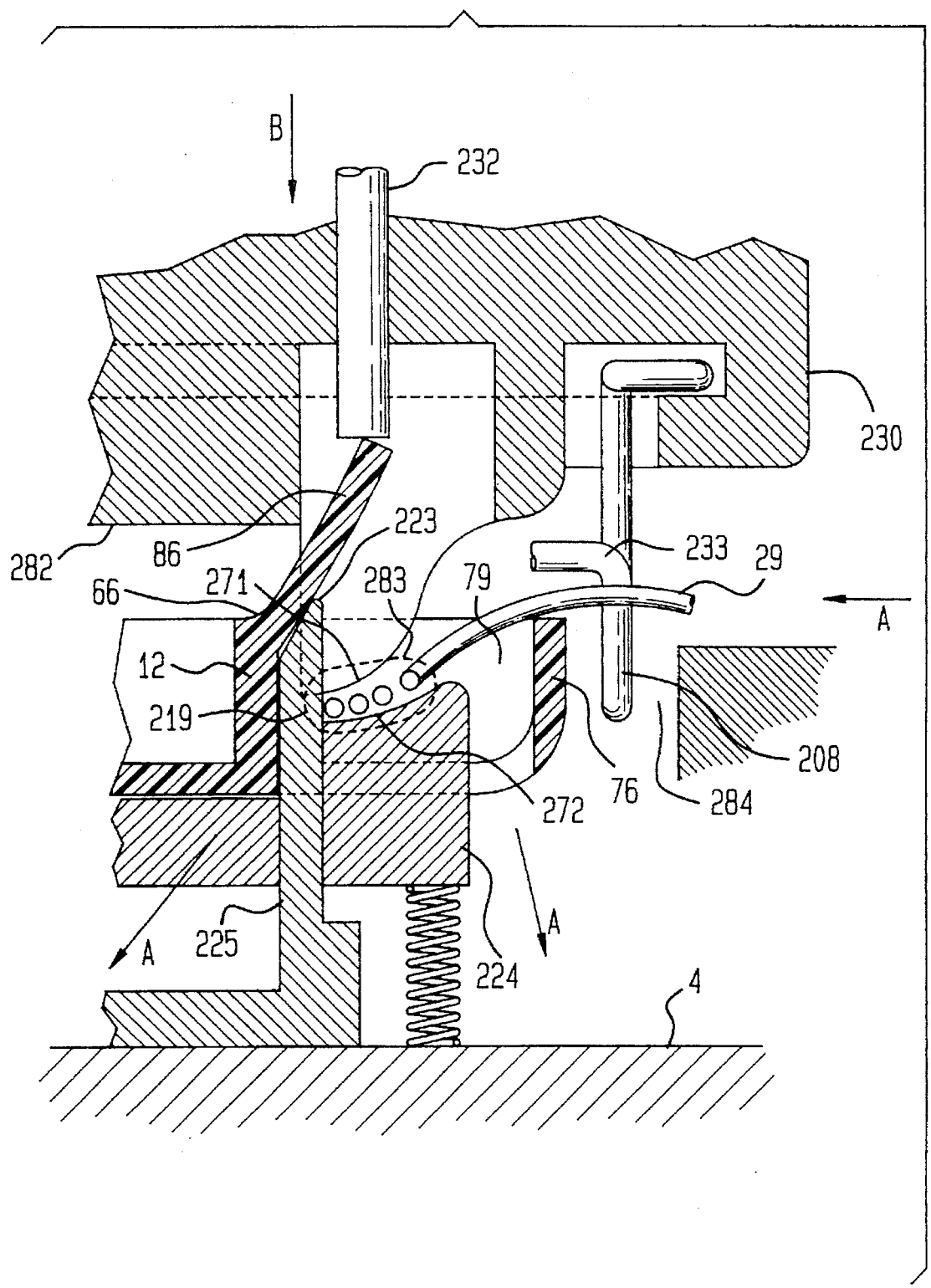
FIG. 38 illustrates a schematic view of the winding tooling detail of FIG. 37 interacting with the tray suture channel and fingers in the closed tool position with the wind cycle underway.
Figure 39A:
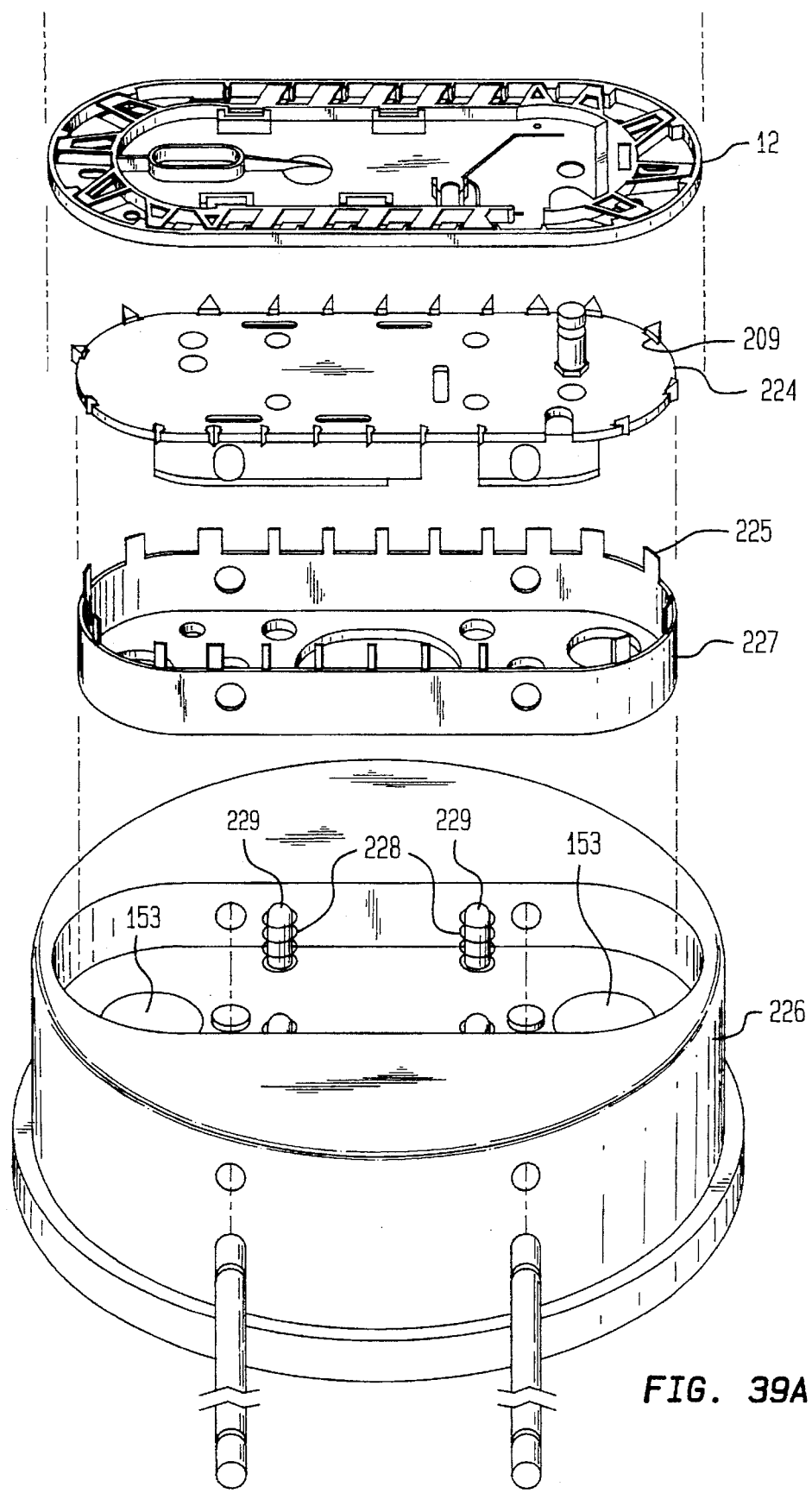
FIG. 39A illustrates an exploded assembly of the lower winding tooling, in the tool nest.
Figure 39B:
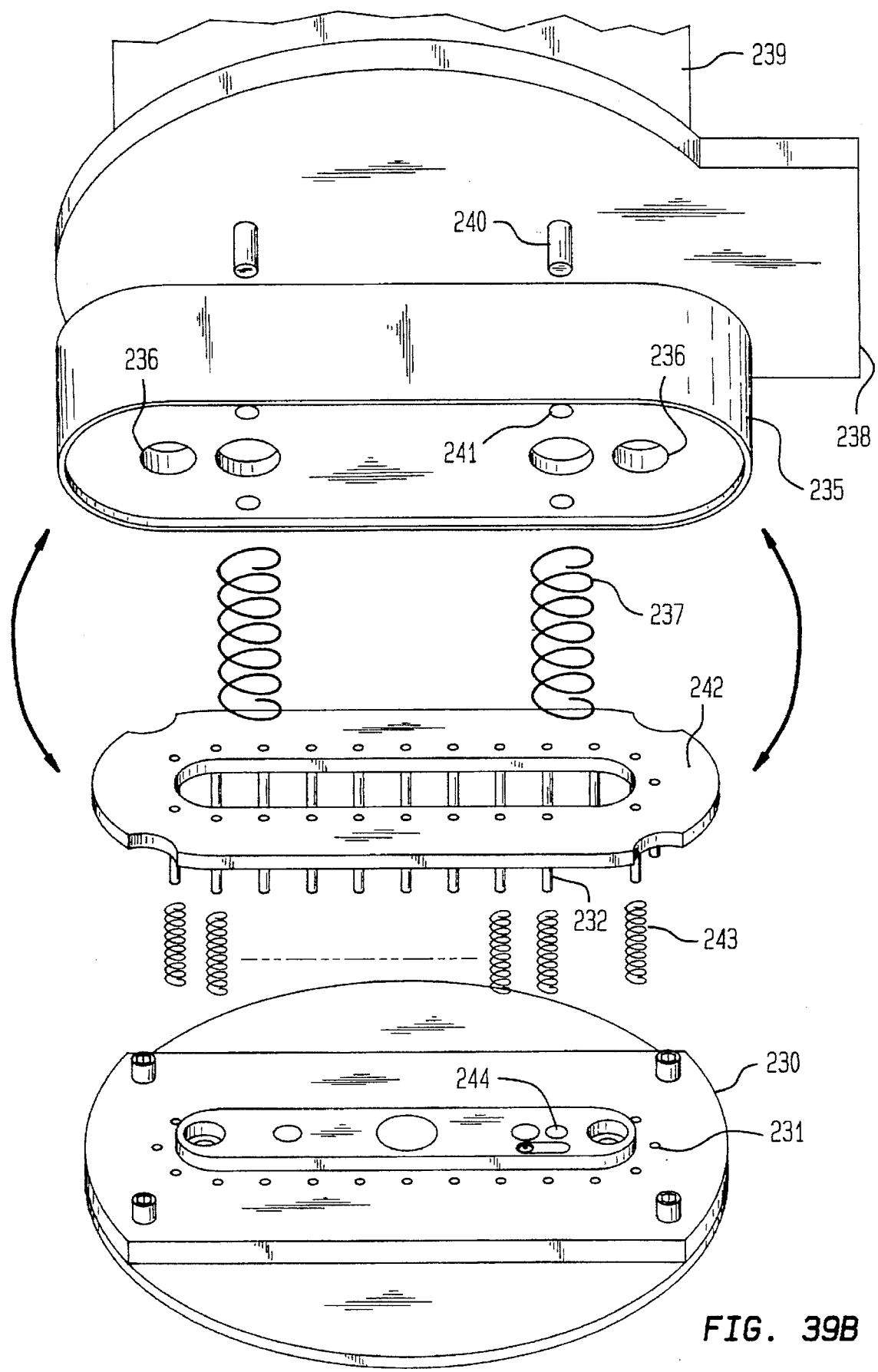
FIG. 39B illustrates an exploded assembly of the top winding tooling in the winding station frame.

The upper tooling, as illustrated in FIGS. 37, 38, and 39B, is comprised of upper platform 230 through which clearance holes 231 allow closing pins 232 to extend. A wire spring-like stylus 233 for tucking the tail portion of the suture is located by groove 234. A matching groove 284 peripheral to blade base 227 similarly guides the downward projection 208 of tail tuck stylus 233. The upper tooling is slideably mounted on upper tool base 235, as illustrated in FIG. 39B, by shoulder bolts through holes 236. Compression springs 237 spring load the assembly. Closing pins 232 can be activated downward by externally displacing plate 238, which is vertically slidable in housing 239, through a downward stroke, thereby causing pins 240, fixedly attached thereto, to move through clearance holes 241 and bear against closing pin plate 242. This displaces pin plate 242 downward, against return springs 243, to drive closing pins 232 also in their downward stroke. FIG. 38 illustrates the above tooling in a closed position.

Tail tucking guide 233 is held stationary relative to the rotating tool assembly and plows the final length of suture tail 29 into the suture channel 79. Assurance that no suture end is protruding from the package is provided by vacuum, evacuated through ports in the lower tooling, creating an air draft in the direction of arrows A. When the winding is completed, closing pins 232 are displaced downward as the upper tooling assembly lifts and forces finger 78 from its upper position 86 to the closed horizontal position illustrated by finger 78 in FIG. 5.

Figure 40A:
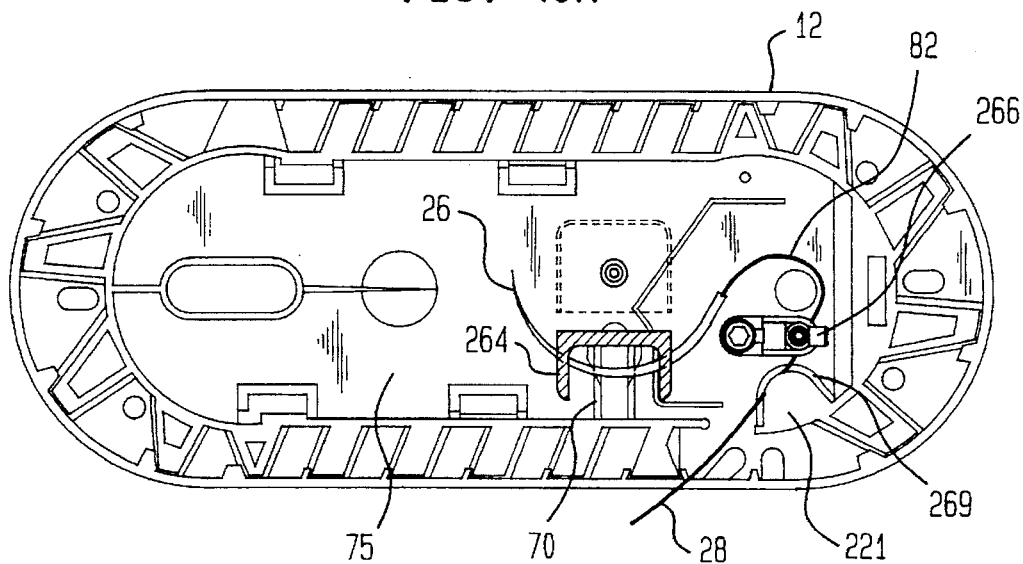
Figure 40B:
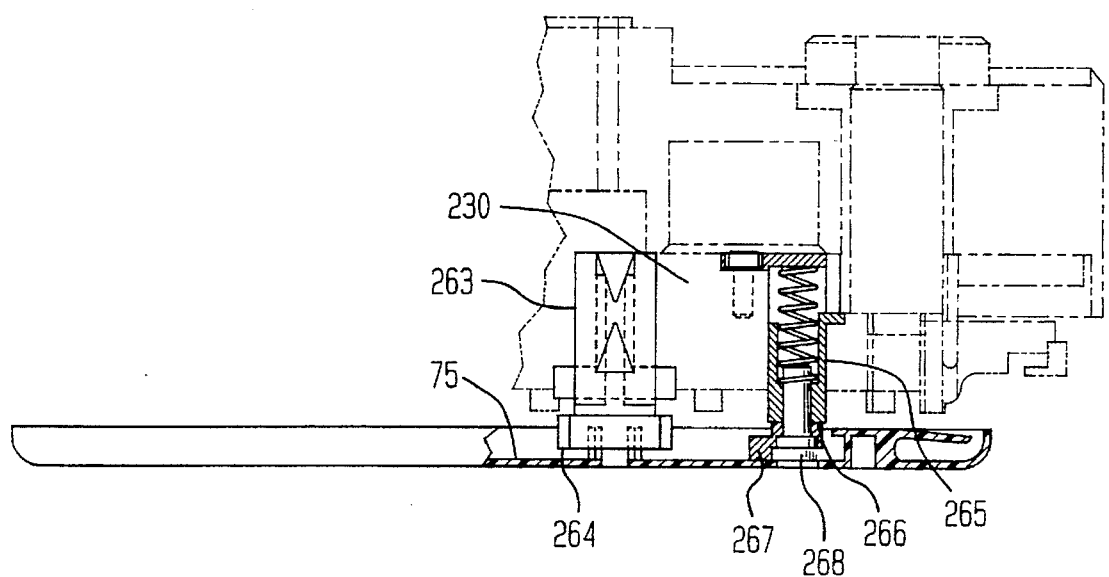
Figure 42:
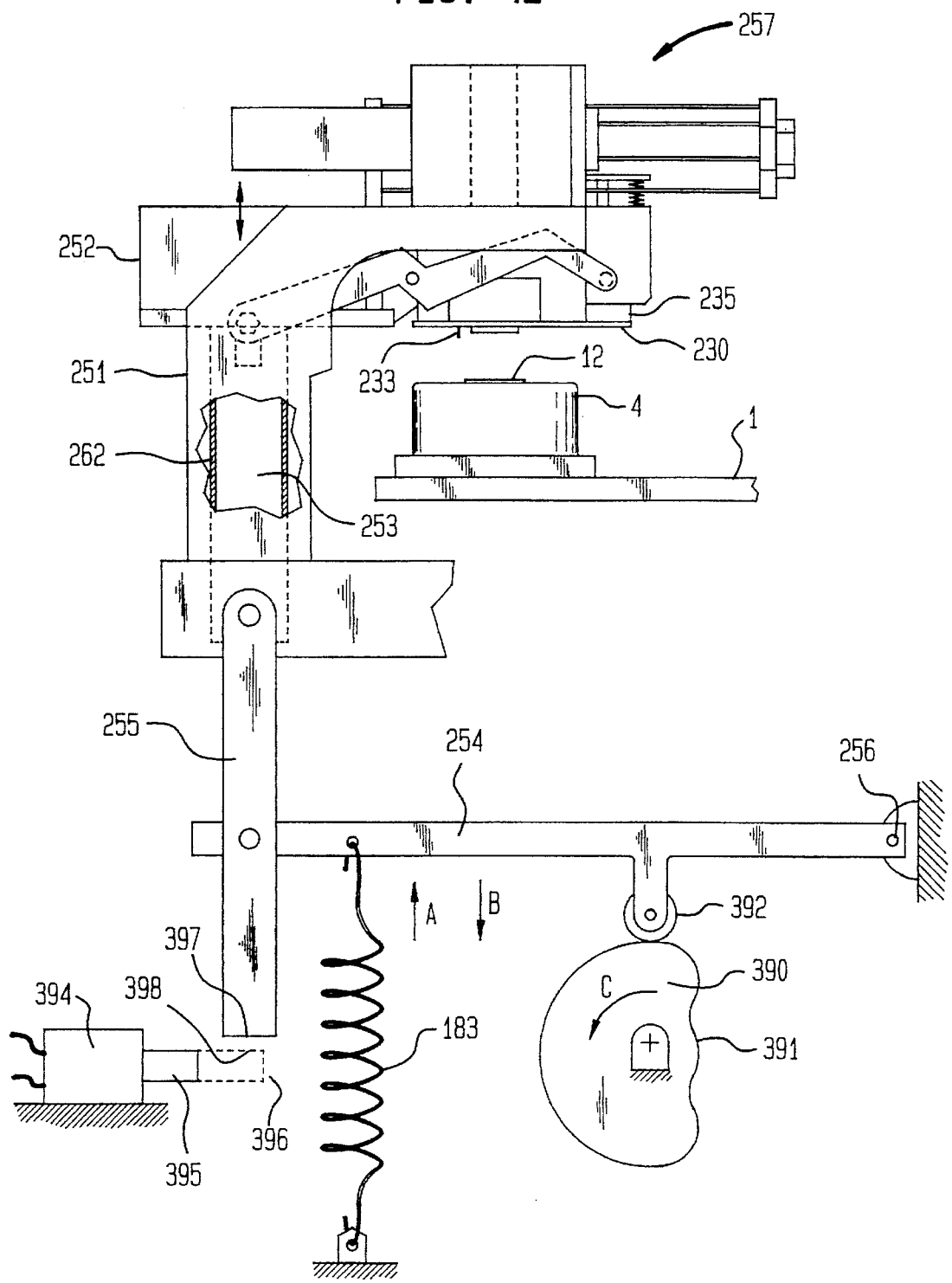
FIG. 42 illustrates an elevation schematic diagram of the winding station frame and operating mechanism.

Vertical reciprocation of the upper tooling is further illustrated with respect to FIG. 42, and is achieved by displacing a central vertical spindle 253 which is slideably mounted in frame 251, and fixed to a horizontal yoke 252 with the upper tooling mounted thereon. Displacement continues downward until upper and lower tooling compressively contact the planar surfaces of tray 12, as illustrated in FIG. 38. At this configuration, finger 78 has been deflected upward to the finger position 86 by cantilever forces applied by tip 223 of blade 225 on the finger causing it to bend hingedly about point 66. The downward displacement of the upper tooling assembly also brings contoured surface 271 of upper platform 230 offset but generally opposite the similar surface 272 of lower tooling platform 224, the two opposing surfaces dimensioned to result in a gap of generally one suture diameter therebetween when fully closed on each other. Windings generated by this tool configuration when the tool assembly is rotated about its vertical axis will result in a relatively flat pattern of the spiral wound loops as shown in FIGS. 38 and 5. Upper wind platform 230 also houses two spring loaded plungers which as illustrated in FIGS. 40A and 40B, protrude downward therefrom so as to bear, with spring force, against molded tray base 75 when the upper winding tooling is closed upon tool nest 4. A "C" shaped foot 264 on needle hold plunger 263 surrounds needle park 70, thereby clamping needle 26 to assure it is not moved when exposed to winding tension in the suture and also to assure it is inserted fully toward base 75 in needle park gap 87. A suture hold down plunger 265 having a spring loaded foot 266 with offset heel 267 which forms gap 268 therebeneath is also used to restrain the suture loop 82. Referring to FIGS. 40A and 40B, foot 266 holds suture loop 82 downward against the floor 75 of tray 12, and further assures it is in sufficiently close proximity to vacuum opening 269 that the force of vacuum draws it under the suture retaining shelf 221. Gap 268 is dimensioned to impart a slight clamping force on suture loop 82 to reduce tensions from winding on the swaged needle attachment as the suture is tensioned and wound into suture channel 79.

Figure 40C:
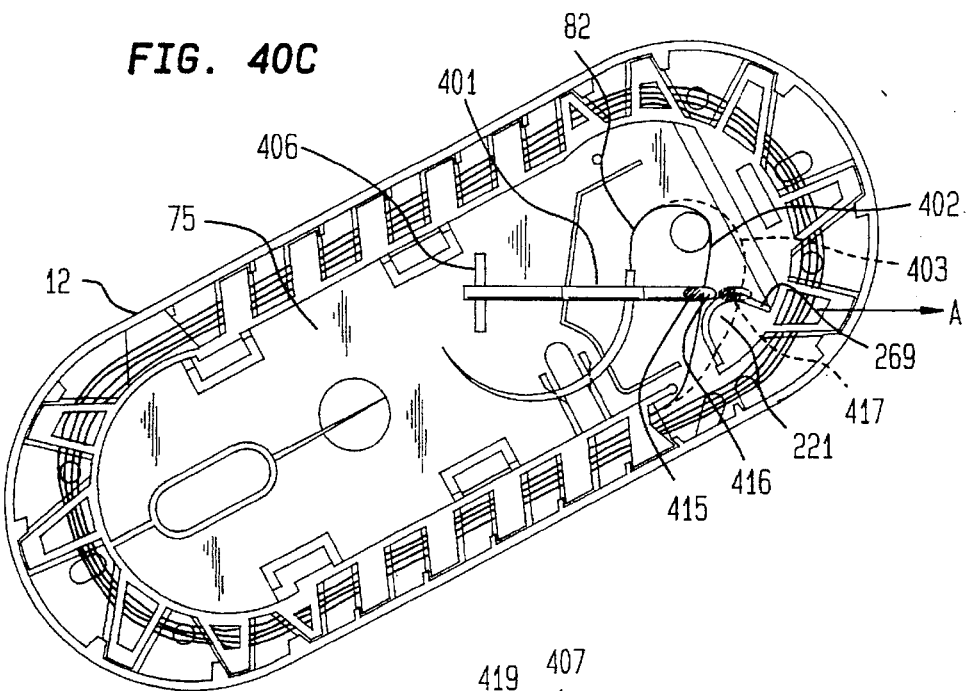
FIGS. 40C, D, and E illustrate an alternative suture hold down mechanism for securing the suture loop.
Figure 40D:
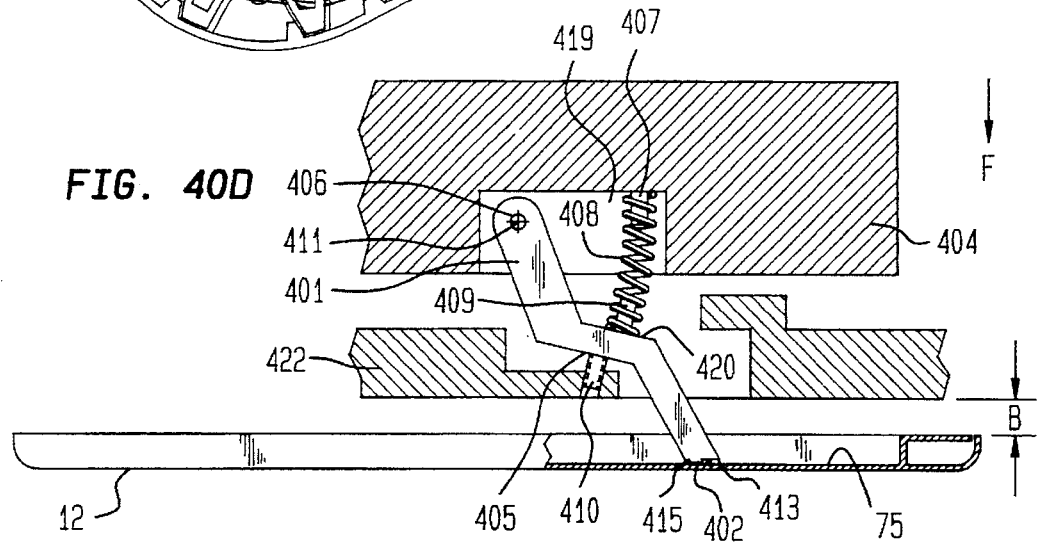
Figure 40E:
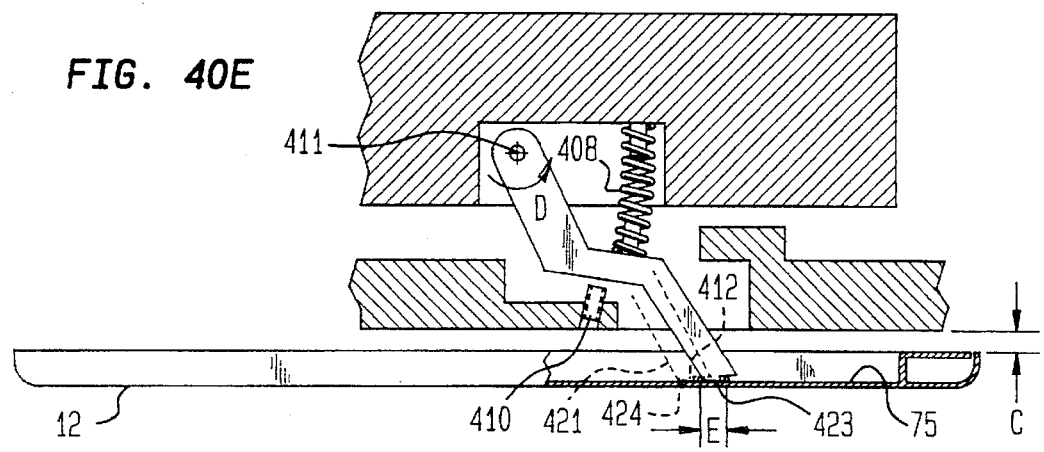

An alternative mechanism that positions suture loop 82 under shelf 221 is illustrated in FIGS. 40C, 40D, and 40E. This can be used in place of the suture hold down plunger 265 and spring loaded foot 266 embodying the offset heel 267 illustrated in FIGS. 40A and 40B if the physical properties such as stiffness and springiness, or lack thereof, of suture loop 82 require a more positive motion.

FIG. 40C is a plan view of package tray 418 mounted in the tool nest at machine winding station IV. Specifically, the objective described herein is to provide a mechanical motion which positively repositions the suture loop 402 under the suture retaining shelf 221 as indicated by the dashed line suture path 403. This displacement of the suture loop 403 under shelf 221 is also enhanced by vacuum force pulling downwardly through port 269 under the shelf. The operative mechanism is a tucking leg 401 which, during the vertical closing motion of the winding station tooling described hereinabove, causes a heel contact area 415 and overhanging ledge 416 to translate in the direction of arrow A, thereby trapping and moving the suture loop portion 402 to a new position indicated by heel contact area 417 such that the suture loop portion 402 is positioned as illustrated at dotted path 403 under the shelf 221.

The mechanism is illustrated in sectioned elevation view 40D. An upper winding tooling block 404 embodies a milled cavity 419 and, therein, a tucking leg 401 pivotally mounted on a cross pin 406. The tucking leg 401 and cross pin 406 mounted thereto are shown in plan view, FIG. 40C, to illustrate the position relative to the package tray 418.

Referring again to FIG. 40D, the tucking leg 401 is biased in a clockwise direction of rotation about a horizontal axis 411 by a compression spring 408, locationally secured at each end by two internal pins 407 and 409, which provides an essentially downwardly directed force against an upper surface 420 located about mid-way along the length thereof.

The position of the tucking leg prior to engagement and rotation is determined by an adjusting screw 410 threadedly mounted in another portion 422 of the tool block 404, and configured to bear against the underside of the tucking leg 401 at a suitable contact point 405 to resist the rotational force about the horizontal axis 411 exerted by the compression spring 408. Upper tooling blocks 422 and 404 and the tucking leg assembly of the foregoing description are spatially located relative to the package tray 418 such that, as the winding upper tooling descends vertically downward, in the direction of arrow F, a heel 415 at the distal end of the tucking leg 401 comes into initial contact with the tray floor 75 at a point to the left of the out-of-place suture loop portion 402. As the winding tooling 404 and 422 descend from the point of initial contact of the tucking leg heel 415 illustrated in FIG. 40D to the lowermost position illustrated in FIG. 40E, (the relative distance illustrated by comparing distances B and C, in FIG. 40D and 40E respectively), the tray floor 75 exerts a reactive force on the descending tucking leg 421, shown in dashed line, at the point of contact 424, rotationally displacing tucking leg 401 about the pivot axis 411 in the direction of arrow D, coincidentally lifting it from contact with the adjusting screw 410 and compressing the biasing spring 408. Resultingly, the contact of tucking leg heel 415 translates to the right a distance E to the final position illustrated and also identified by heel print 417 in FIG. 40C.

The upper winding tooling illustrated in FIG. 40E remains positioned vertically as shown for the duration of the winding station rotations of the tool nest (not shown) thereby establishing the package suture position and tension such that the suture loop portion 402 will tend to stay in position 403 under shelf 221 after the winding tooling opens and the tucking leg 401 is no longer in contact with the package tray. Upon vertical withdrawal of the winding tooling from the package tray 412, the compression spring 408 is configured to rotate the tucking leg 401 clockwise to the original position illustrated in FIG. 40D in preparation for the next machine cycle.

Figure 41:
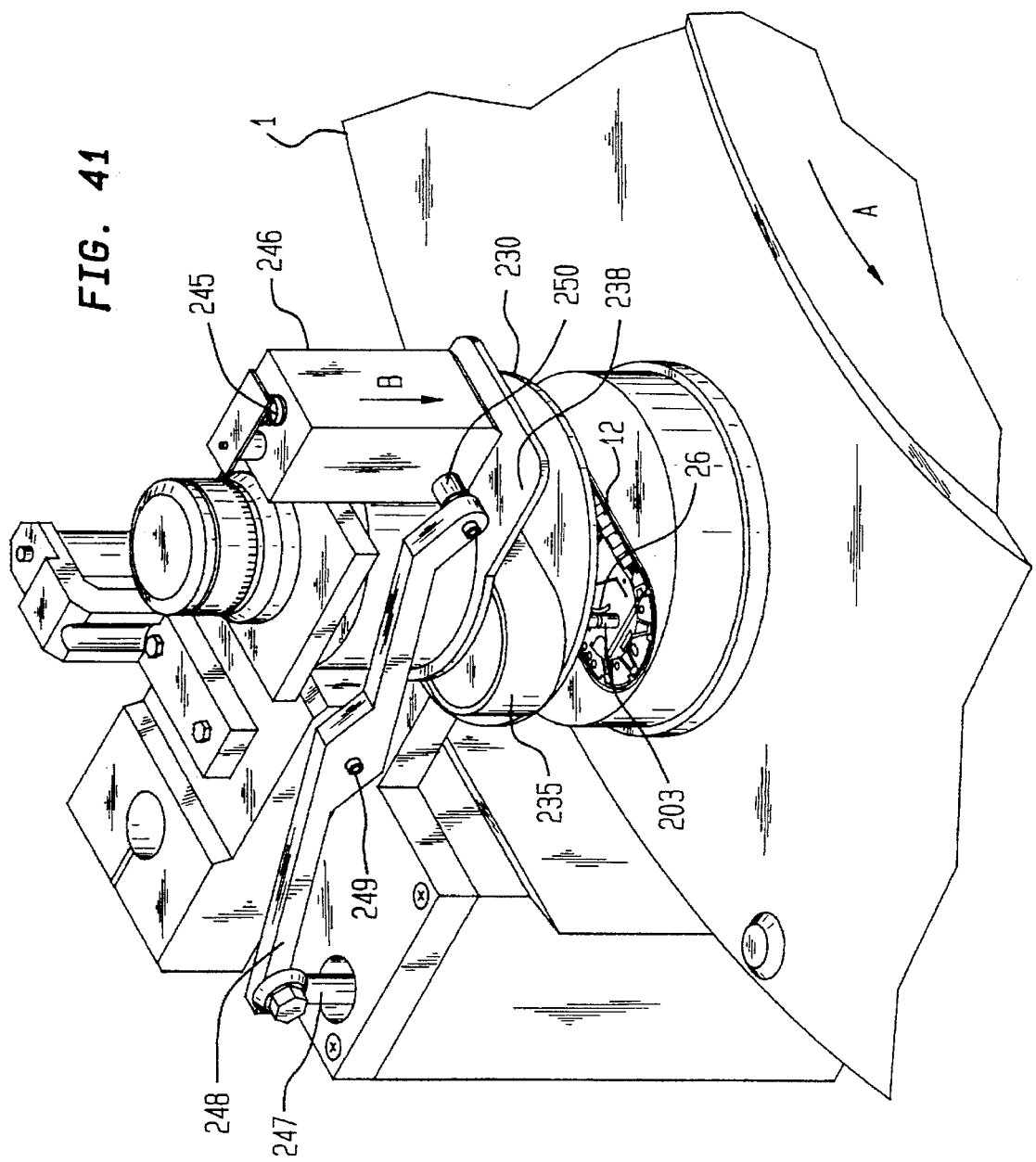
FIG. 41 illustrates an isometric view of the winding tool frame and the tool nest.

FIG. 41 illustrates the winding station structure at station IV of the machine, with tool nest 4 indexed into position by turret 1 holding tray 12 in preparation for tooling closure and suture winding. Rotation for winding is driven by the system described and illustrated with respect to the foregoing FIGS. 11 through 13C. Upper platform 230 and upper tool base 235 are fixedly mounted on a free turning rotatable central spindle thereabove (not shown), and when in the closed position are driven in rotation by base 4, specifically the engagement of pilot pin 203 into a matching hole 244 as illustrated in FIG. 39B in upper platform 230. Continuing with reference to FIG. 41, plate 238 is fixed to vertical rod 245, which is slidable in a linear ball bushing (not shown) within mounting structure 246. The mechanism that lowers closing pins 232 at the end of the winding cycle is comprised of push rod 247 pushing vertically up on the distal end of lever 248, which pivots about post 249 to cause a downward displacement of the proximal end and cam roller 250 attached thereto. Cam roller 250 engages the upper surface of plate 238 to displace closing pins 232 illustrated in FIGS. 38, 39B downward.

The winding station structure as illustrated in FIG. 42 is comprised of an inverted "L" shaped frame 251 with the outwardly extending portion of the structure essentially cantilevered so as to position the upper tooling described above over tool nest 4. Upper tool base 235 and associated tooling is fixedly mounted to one end of horizontal yoke 252. Vertical rod 253 is fixedly attached to the second end of yoke 252 at the top, and connected through pinned link 255 to cam lever 254 at the bottom. Vertical rod 253 is confined by friction free bushings 262 in the vertical portion of frame 251, so that the upper tooling, horizontal yoke, and rod 253 are vertically slidable as a unit and positioned vertically by cam lever 254. Cam lever 254, pivotally mounted to the machine frame by pin 256, is angularly displaced by cam follower 392 riding on plate cam 390. A rise in cam 390 causes an angular displacement of arm 254 in the direction of arrow A, thereby opening the winding tooling thereabove. Correspondingly, a fall or dropping off in cam 390 allows spring 183 to displace arm 254 in the direction of arrow B and accordingly close the winding tooling. Molded tray 12 may occasionally be missing from tool nest 4, and it is preferable to not close the winding tooling on an empty tool nest. For deactivation of the closing mechanism, a missing tray detected by the vision system at machine station 2 sends a signal to the control system computer, which causes a switchable compressed air source to pressurize air cylinder 394 thereby extending cylinder rod 395 to the horizontal position indicated by dashed outline 396. When cam follower 392 falls off the rise of cam 390 in the circumferential region indicated at 391, the side face 398 of air cylinder rod 395 blocks the downward path of link 255 by contacting endface 397 and stalling downward motion of arm 254 by spring 183, thereby preventing closure motion of the vertical slide linkage and of the winding tooling thereabove. Air cylinder 394 is re-set for each machine cycle.

Figure 43:
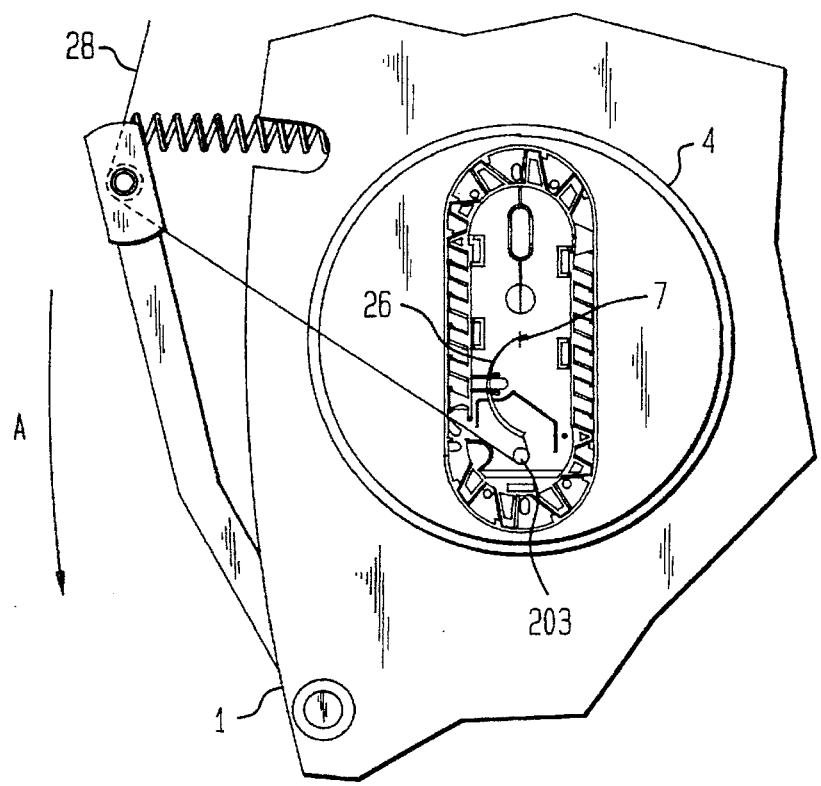
FIGS. 43 and 44 illustrates sequential plan views of the rotational orientation sequence of the tool nest as it relates to the 180° re-set of the top winding tooling.
Figure 44:
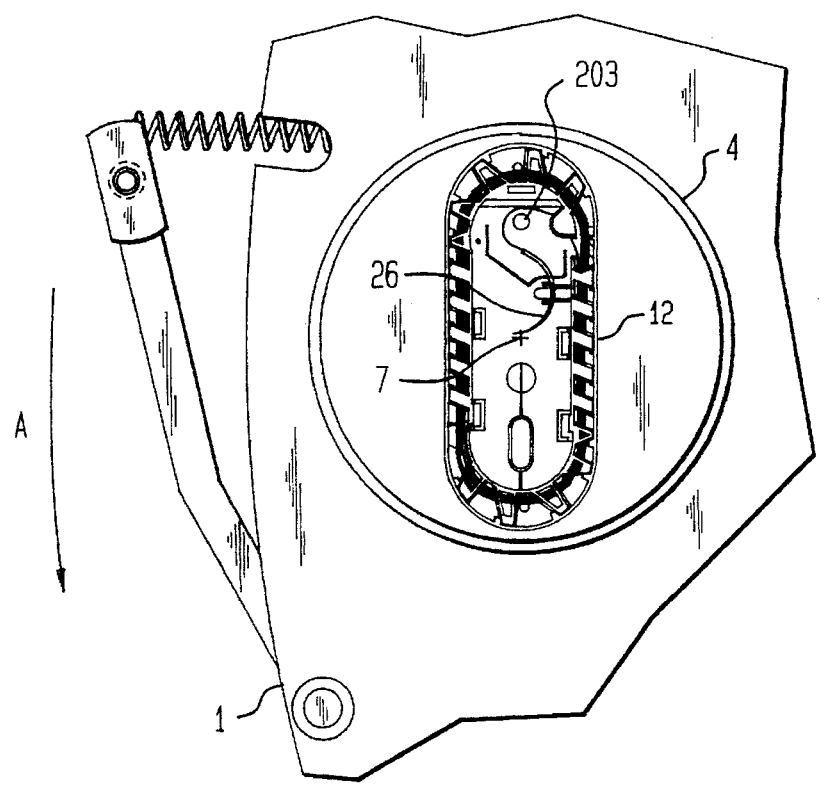
Figure 45:
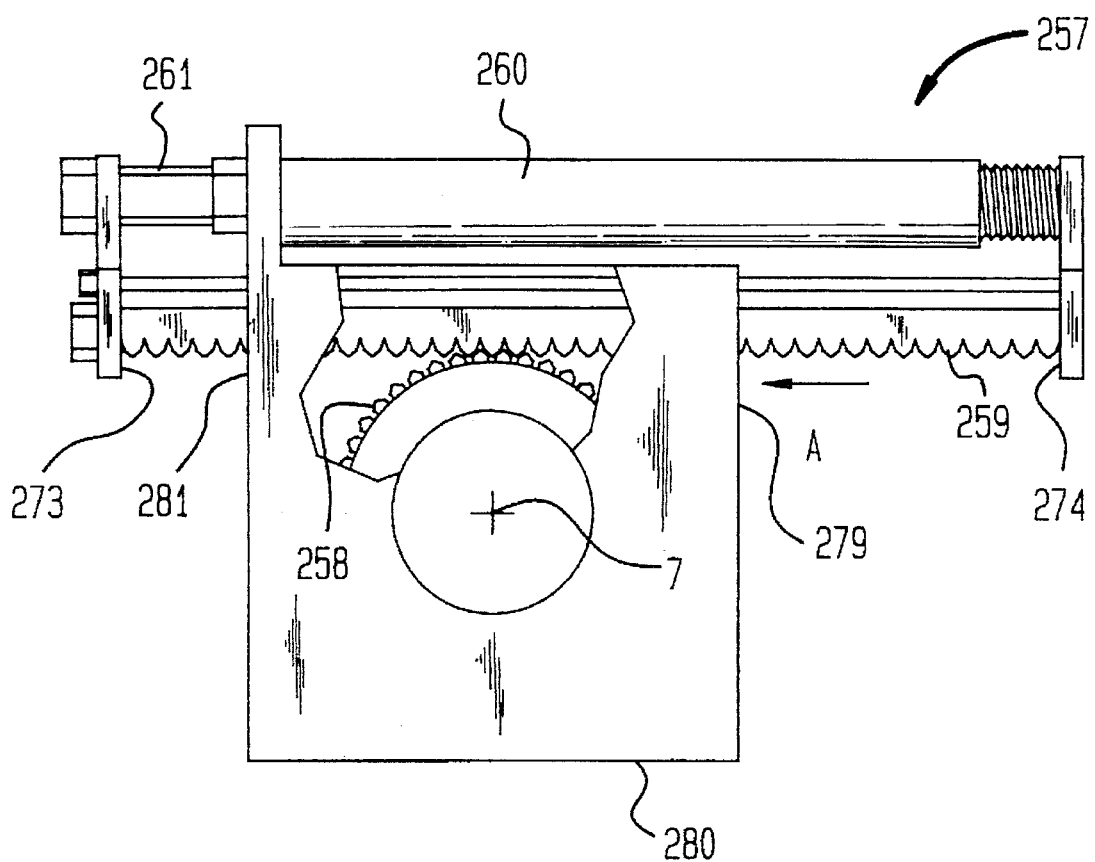
FIG. 45 illustrates the 180° top tool rotation mechanism.

FIG. 41 illustrates the rotational orientation of tool nest 4 when it is brought into machine winding station IV prior to the wind cycle. Pilot pin 203 and the end of tray 12 containing the needle 26 are leading, at the more forward end of the tray with respect to turret index direction indicated by arrow A. This is further illustrated in FIG. 43. Conversely, FIG. 44 indicates the rotational orientation of tool nest 4 180° from the position illustrated in FIG. 43 with pilot pin 203 and needle 26 at the trailing end with respect to index arrow A. This half winding is a machine requirement after winding when the tool nest 4 is leaving machine station IV. This requirement makes the winding rotational cycle of nest 4 comprise an odd number of half turns about nest axis 7, or, restated, the winding rotational cycle at station 4 will consist of the number of degrees of rotation to wind the full length of suture 28 plus additional rotation to position tool nest 4 180° from the starting orientation. While this could be easily accomplished by programming the computer controlled servo motor driving nest 4 (not shown), it adds an additional function for the winding station mechanism. Referring to FIG. 41, upper tooling platform 230, upper base 235 and associated tooling must be re-set by rotating 180° when in the raised (disengaged) position during each wind portion of the cycle. This is accomplished by 180° index mechanism 257, illustrated in FIG. 42, and schematically diagrammed in FIG. 45, comprised of pinion 258, coaxial to nest axis 7, joined torsionally through a mechanical dog clutch (not shown), which maintains rotational registration to upper tooling vertical spindle (not shown) also coaxial to axis 7, to which is mounted upper tooling elements 230 and 235 described previously. Gear rack 259, meshed with pinion 258, is connected by cylinder rod 261 to air cylinder 260, and the stroke of these components sized to generate 180° rotation of pinion 258 when it traverses from end 273 to end 274. The cycle of the 180° index device 257 occurs after disengagement of the above described dog clutch (not shown) during the rotational winding cycle of nest 4 and associated winding tooling. It also concurrently cock the index mechanism by activation of air cylinder 260 and resulting extension of rod 261 and rack 259 in the direction of arrow A which causes point 274 to stop against point 279 on indexer frame 280, engages the dog clutch, and then provides retraction by air cylinder 260, rod 261 and rack 259 opposite to the direction of arrow A causing point 273 to stop against point 281 on frame 280 with a resulting 180° rotation of pinion 258 and the upper winding tooling torsionally connected thereto.

Station (V)

Station 5 is utilized entirely for automatic inspection. The station structure supports a digitizing camera and special lighting similar to that described for camera 207 of station III illustrated in FIG. 29, which images the tray 12 and needle 26 illustrated in FIG. 44. The camera is connected to a computer analysis modules located in the machine control cabinet.

This system is programmed to analyze needle and suture placement, particularly responding to any suture loops that are outside the outer margins of tray 12. Defects detected send a signal to the control computer, causing the package to be identified at each subsequent machine cycle and location, and ultimately rejected at machine station VIII.

Station (VI)

Station VI of the package assembly machine feeds, preforms, and assembles the cover label 71, illustrated in FIG. 6, to the tray 12, which has the needle with attached suture 25 wound and placed therein. This assembly results in the completed assembly illustrated in FIG. 7.

Figure 46:
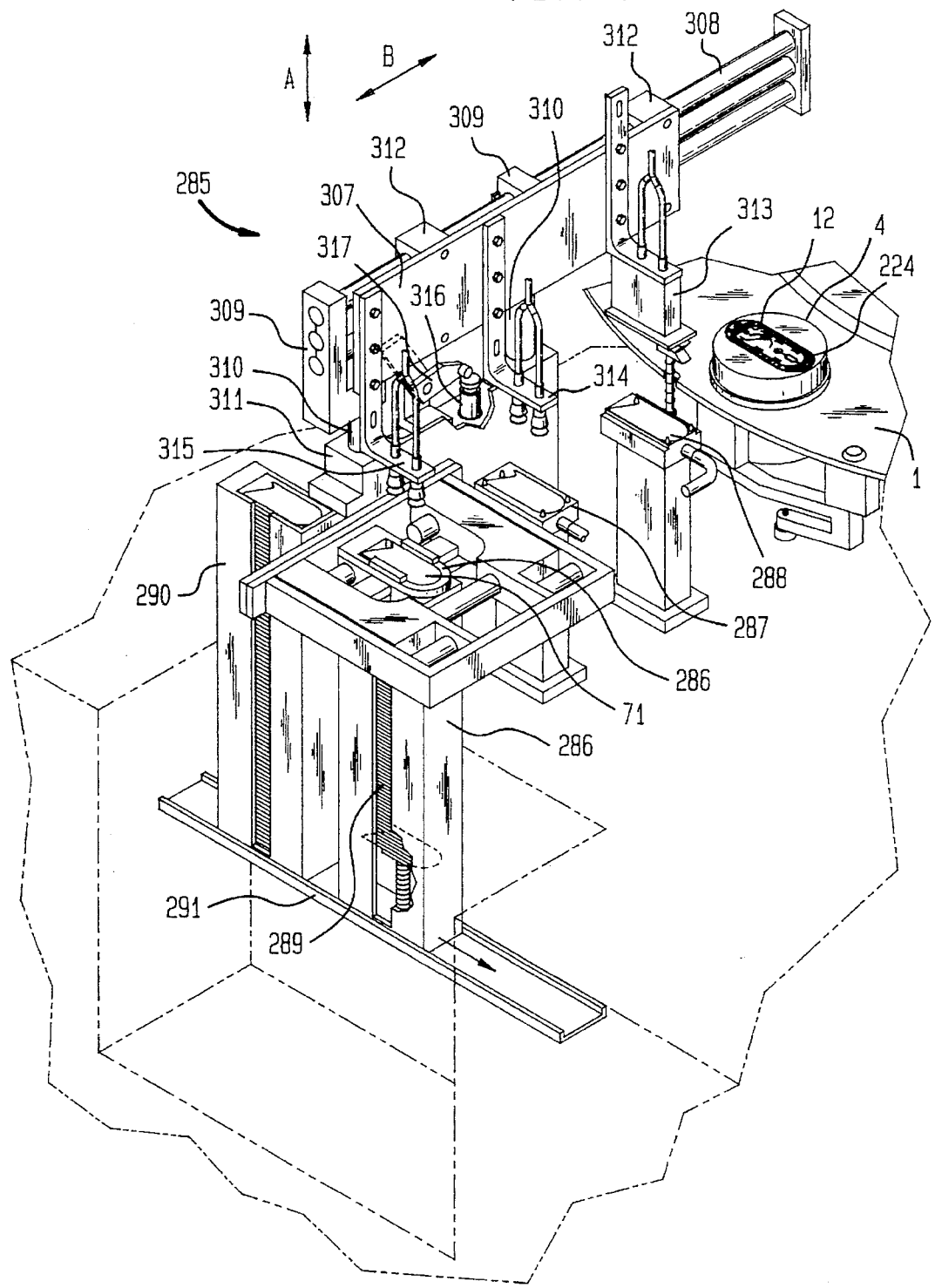
FIG. 46 illustrates an isometric view of the label load mechanism at station VI.

An overview of station VI is provided in FIG. 46. The primary operative mechanism of station VI is a rectilinear vacuum pickup slide assembly 285 which functions as a transport device for advancing label covers 71 from a storage magazine 286 to an intermediate station 287, to a pre-form station 288, and finally to the package tray 12 on lower tooling platform 224 on tool nest 4, which has been brought into position for this operation by the machine main turret 1.

Figure 47:
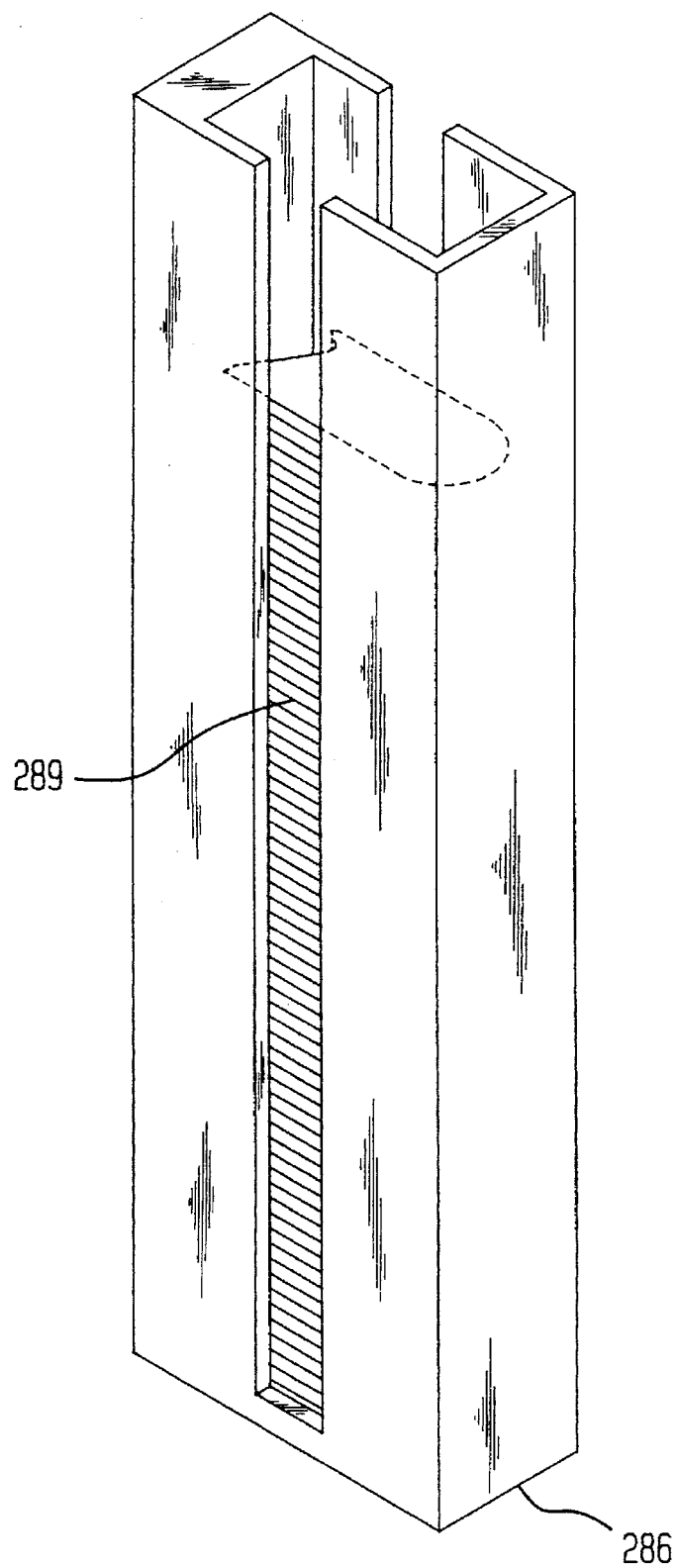
FIG. 47 illustrates a label magazine.

The supply of cover labels necessary to feed the machine is fed from a vertical magazine 286 containing a stack 289 of pre-printed and die cut labels 71. Stack 289 in magazine 286 is sufficient in quantity to feed the machine for a period of time before requiring operator attention to replenish the supply. Individual magazines as illustrated in FIG. 47, are removable from the machine for filling off-line, thereby not requiring the machine to stop. The label feed system includes a dual magazine shuttle 291, that presents one magazine in position to feed the machine while the other is free of moving mechanisms and accessible for operator removal of the empty and replacement with a full unit without interruption of machine operation. A second feature also avoids machine interruption by continuing the supply of label covers while the shuttle is changing from one magazine to the other. FIGS. 48–52 illustrate this sequence.

FIG. 48 illustrates the machine condition when a filled magazine 286, containing a full stack of labels 289 is first put into the machine. Turning the label delivery system on, at the machine control panel (not shown), causes the label stack elevator 292 to elevate in the direction of arrow A, as illustrated in FIG. 49, thereby lifting stack 289 vertically into feed cup 298 until photoelectric detector 293 senses that the top label 294 of stack 289 has reached the top position 295. Vacuum cups 296 are arranged so as to descend on top label 294, lifting and translating it to the next stage of the label feeding sequence. Nibs 297 are positioned so as to slightly interfere with vertical removal of label 294, thereby assisting separation so that only one label is removed by vacuum cups 296.

Figure 52:
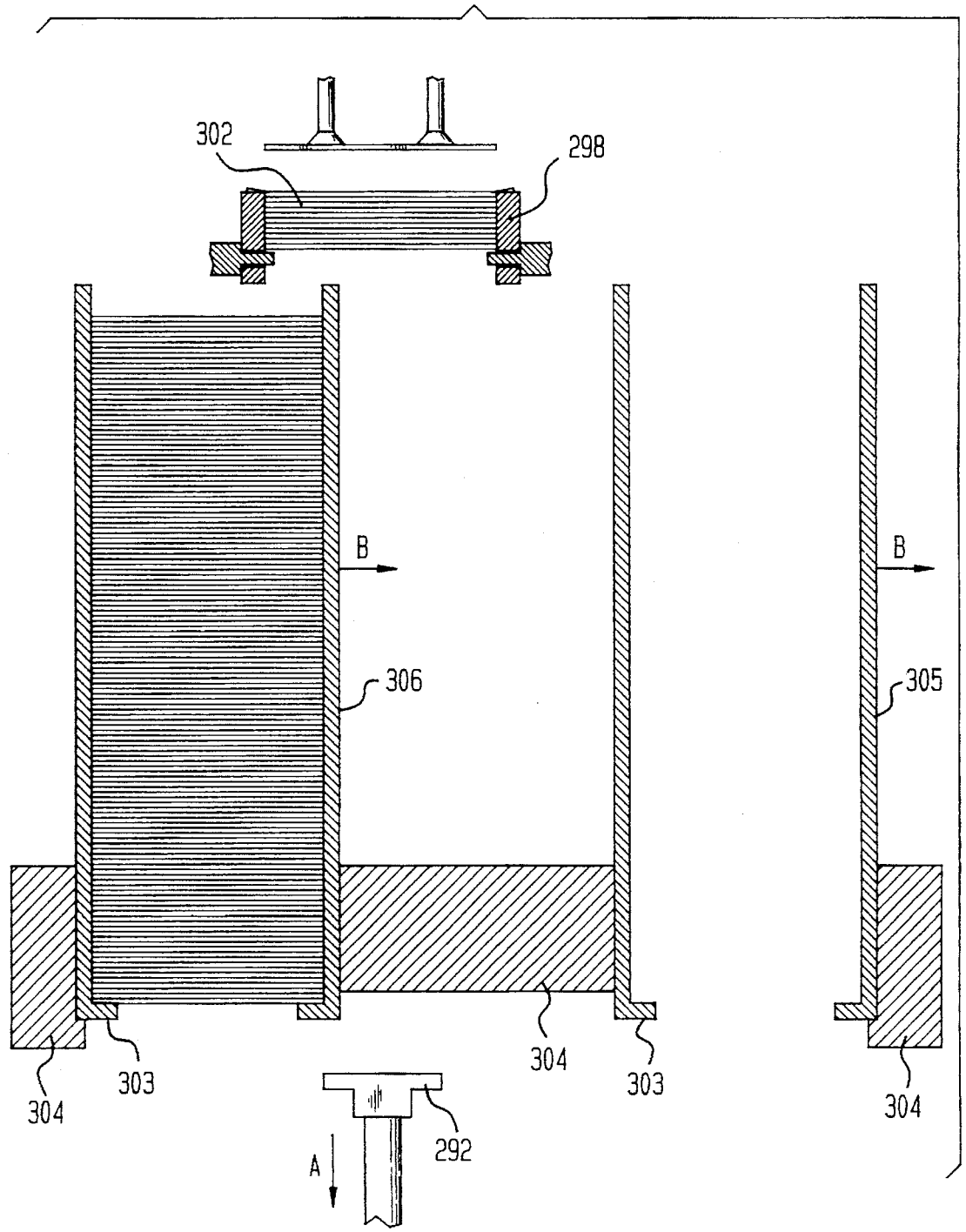

Elevator 292 is attached to rod 299, which is the linear sliding component of a servo motor driven commercial lead screw device, sized to have sufficient stroke to fully extend to the position illustrated in FIG. 50. As the machine is cycled, and labels to feed it are removed from stack 289, photodetector 293 is so configured that continued removal of top label 294 will drop the level below 295, a condition sensed by detector 293, causing a signal to the control computer to energize elevator 292 incrementally upward, until sensor 293 is again triggered. When elevator 292 raises the remaining portion of stack 289 completely out of magazine 286 and into feed cup 298, as illustrated in FIG. 51, the excessive vertical stroke of rod 299 is detectable by a limit switch (not shown), thereby causing short stack supports 300, driven by an air cylinder slide (not shown), to enter openings 301 in feed cup 298 and provide bottom support to short label stack 302. Short label stack 302 is designed to provide a limited supply of labels to keep the machine running while a change cycle for magazine 286 takes place. The change cycle is illustrated in FIG. 52, in which elevator 292 is first lowered to clear the bottoms 303 of magazines 305, 306. Magazine holding frame 304 is then translated horizontally in the direction of arrow B, thereby moving empty magazine 305 out from under feed cup 298, and re-filled magazine 306 into the feeding position under feed cup 298, enabling the first stage illustrated in FIG. 48 to repeat.

Figure 53:
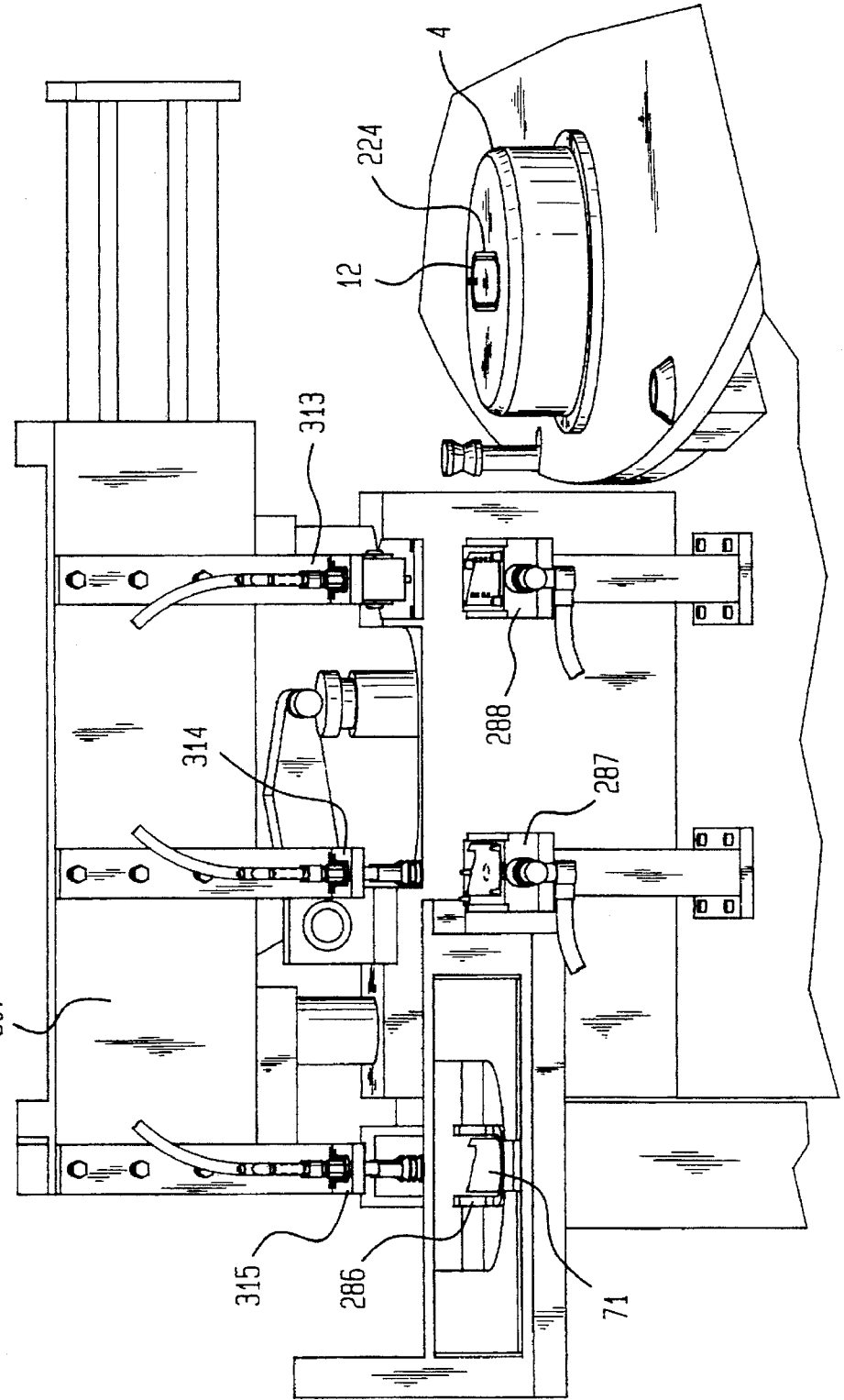
FIG. 53 illustrates the label loading station prior to initiation.

Referring to FIG. 46, rectilinear slide assembly 285 is comprised of a vertical slide carriage 309, fixedly attached to vertical rods 310 slideably mounted in fixed bushings 311, horizontal slide carriage 307, fixedly attached to horizontal bushings 312 which are slidable on rods 308. Horizontal carriage 307 is moveable vertically as indicated by arrow A, by cam displacement of vertical rods 310, and horizontally as indicated by arrow B, by cam displacement of push rod 316 which operates bell crank 317, thereby imparting horizontal motion thereto by a pin and slot connection to reciprocate in the direction of arrow B. The cam driven slide arrangement herein described is capable of moving horizontal slide 307 in any horizontal or vertical stroke, or combination thereof, within the limits of stroke and cam configuration designed therefor. In this instance, the motion pattern for slide 307 is as indicated by arrows A, B, C, D, E, F on FIG. 53A.

Figure 54:
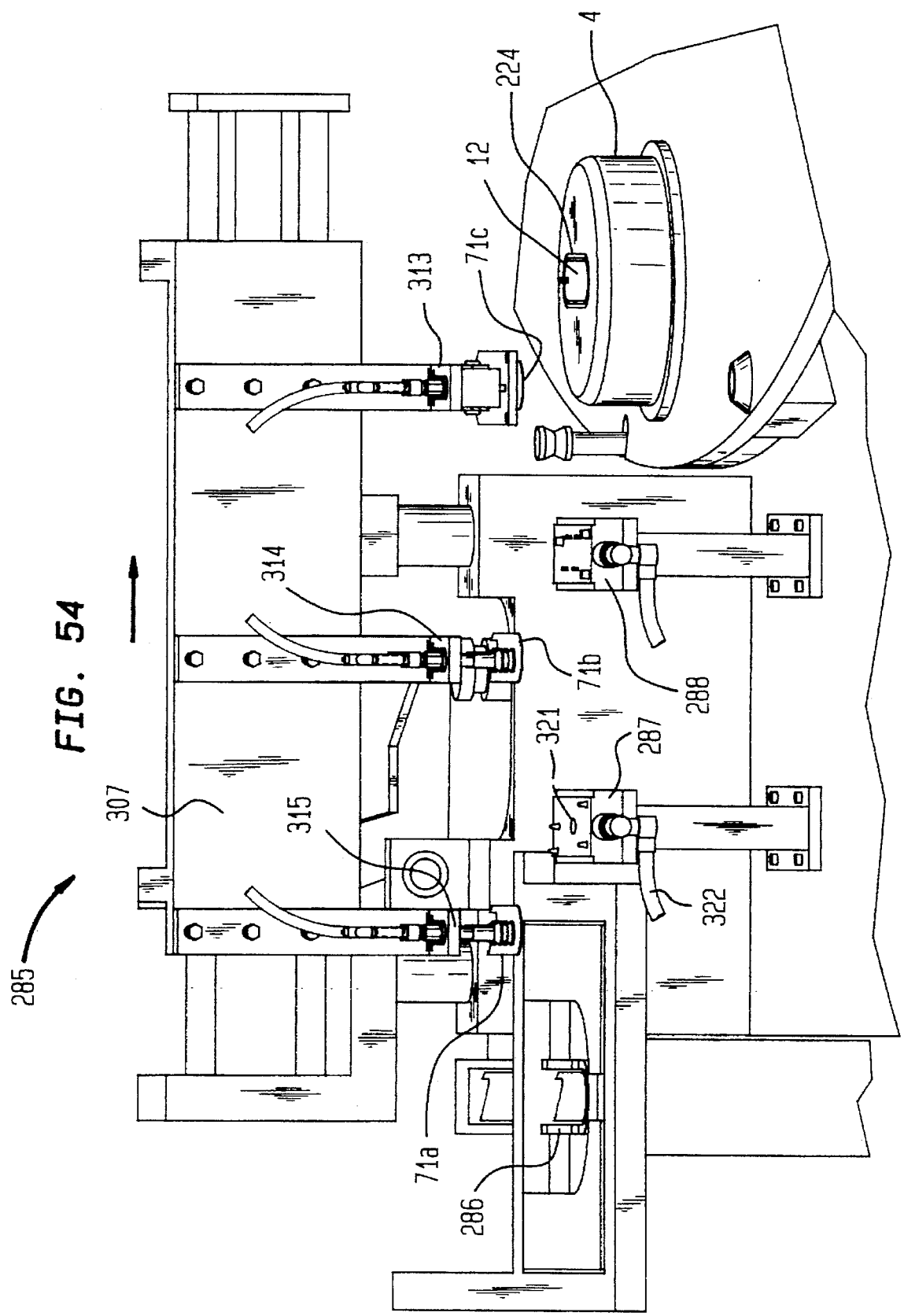
FIGS. 54, 55, and 56 illustrate in a sequential manner the stages of the label loading station in its operating sequence.

Referring to FIG. 54, vacuum cup assemblies 313, 314, and 315, are fixed to horizontal carriage 307 and arranged, in concert with the timing of vacuum source thereto, so as to progressively, in incremental steps for each machine cycle, advance labels as follows: Cup 315 moves label 71a from magazine 286 to intermediate station 287; cup 314 moves label 71b from intermediate station 287 to pre-form station 288; vacuum cup assembly 313 moves label 71c from pre-form station 288 to tray 12 on lower tooling platform 224 in tool nest 4. Label transfer or hand-off at each station is accomplished by alternating the vacuum supply to the moveable cups and the station receiving platform.

Figure 55:
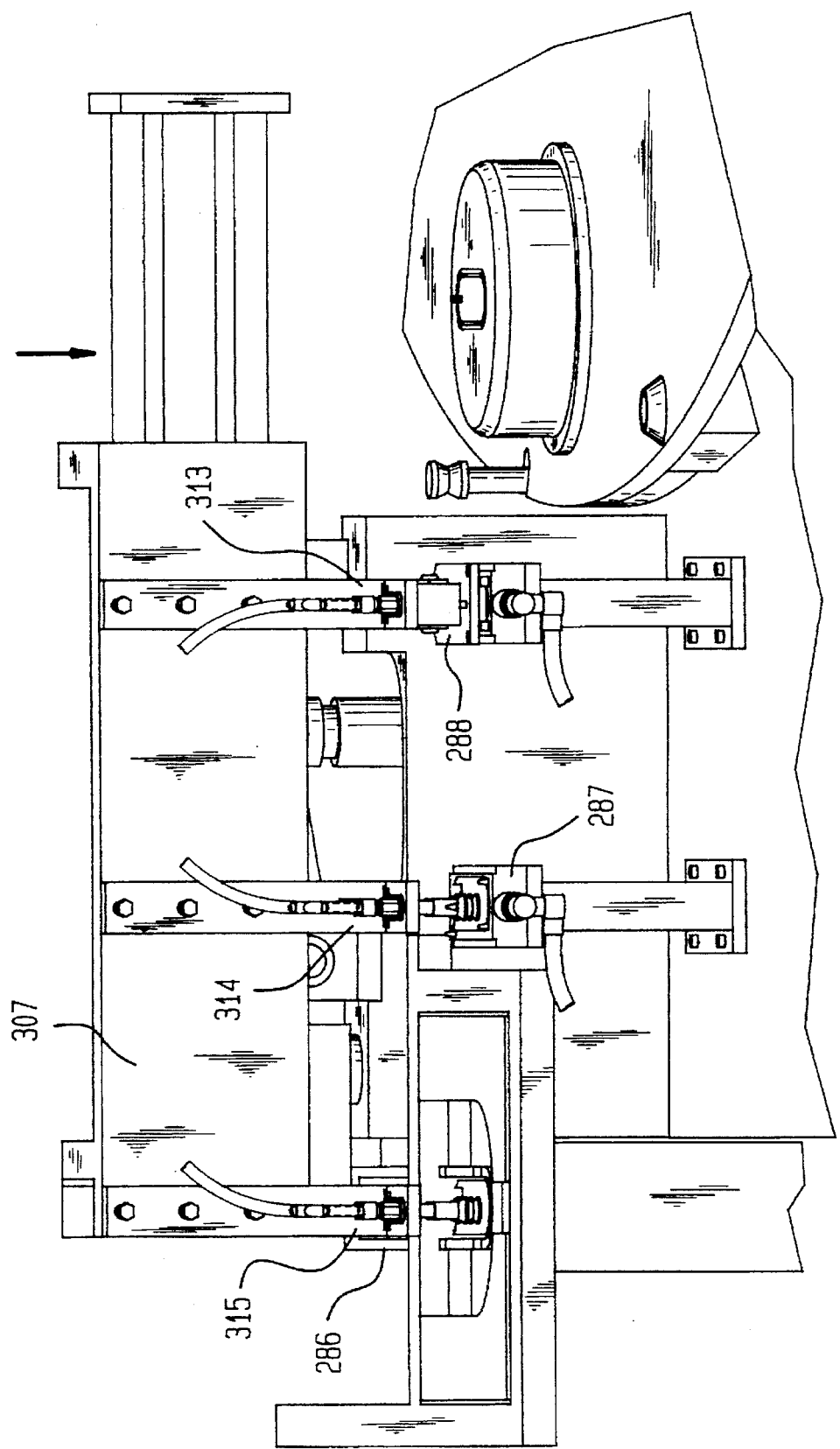

FIG. 55 illustrates slide assembly 307 and vacuum cup assemblies 315, 314, and 313 mounted thereon in position to pick up labels from stations 286, 287, and 288 respectively.

Figure 56:
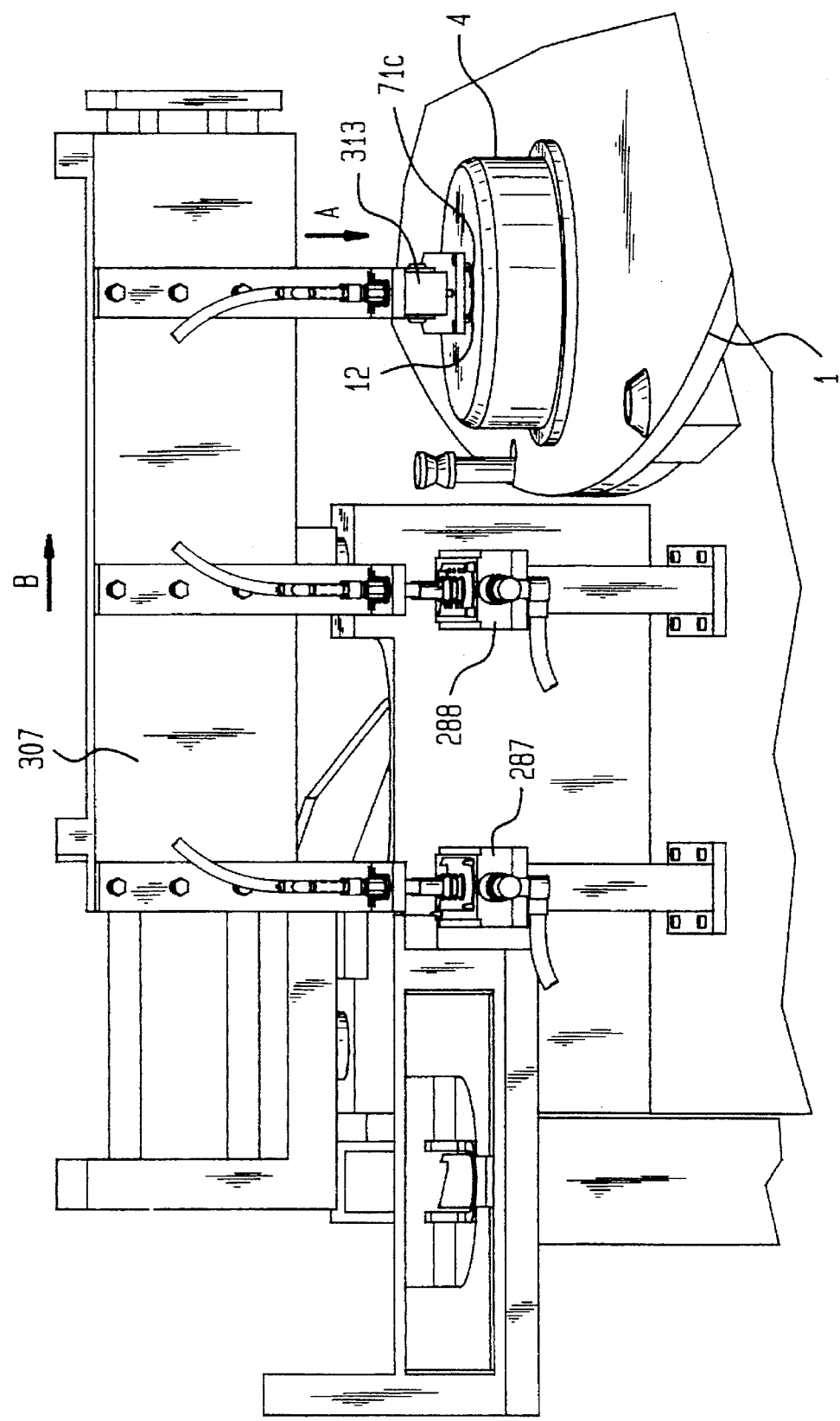

FIG. 56 illustrates slide assembly 307 transferring these labels to stations 287, 288, and tray 12 respectively.

Referring to FIG. 54, in addition to providing a hand-off point for label 71b, station 287 prevents double labels, two stuck together, from being assembled to package 163, by providing a medium degree of vacuum to station port 321 through vacuum hose 322 at the same time vacuum cup assembly 314 is lifting label 71b from station 287, also with a vacuum grip. This simultaneous above and below vacuum gripping provides a separating force for the instance in which two labels are adhering together. This also requires the control computer to withhold feeding the next label for one cycle accordingly, which is determined by vacuum level sensor for station 287.

Continuing with reference to FIG. 54, in addition to providing a hand-off point for label 71c, station 288 serves to pre-form label 320 by bending tabs 72 as illustrated in FIG. 6, downwardly through the plane of label material 122 to separating diecuts 121, to thereby reduce the stress and potential for tearing at hinge point 124 when the tabs are staked during final assembly at the next station.

FIG. 57A illustrates the upper pre-form tool, comprising spring loaded stripper plate 323, attached by shoulder bolts 327 extending slidingly through upper tool block 326, positioned so as to shield staking punches 325, partially entered in clearance holes 330 from contact with label 71 prior to contact with pre-form anvil 329. Vacuum hose 341 is hermetically sealed to vacuum tube 342, integral to stripper plate 323 and causes label 71 to remain held thereto until the vacuum source is switched off by the control computer after final staking to tray 12.

FIG. 57B illustrates the completed pre-form position. The pre-form operation requires that tool block 326 be moved downwardly toward the pre-form anvil 329 with sufficient downward force in the direction of arrow A to overcome the force of springs 331, with a limited downward stroke displacement so as to only partially close gap 332. This causes upper tool block 326 to extend staking punches 325, attached thereto, downwardly to partially punch through tabs 72 in label 71, which then extends partially into wells 333.

Assembly of label 320 to package tray 163 is illustrated in FIGS. 56 and 57C. Pre-form tool assembly 313, mounted to upper tool block 326 is positioned over tool nest 4 by slide assembly 285, and lowered to the position illustrated in the direction of arrow A. Label 71c is precisely centered over package 12, and the staking sequence described for FIGS. 57A and 57B is repeated with the function of anvil 329 for the pre-form operation being replaced by package molding 12 as illustrated in FIG. 57D. The overall mounting structural elevation of rectilinear slide assembly 285 depicted in FIG. 56, relative to tool nest 4, on turret 1, is such that the downward stroke of assembly 313, indicated by arrow A, results in deeper penetration of staking punches 325, into pocket 165, than the pre-form stroke illustrated in FIG. 57B. FIG. 57D is an enlarged view of staking punch 325 at the bottommost part of its stroke in the direction of arrow A. A detailed description of package label attachment and the staking of tabs to secure same is illustrated and described with respect to in FIGS. 6-8. The assembled package 73 completed by label placement machine station 6 is illustrated in FIG. 7.

Figure 58A:
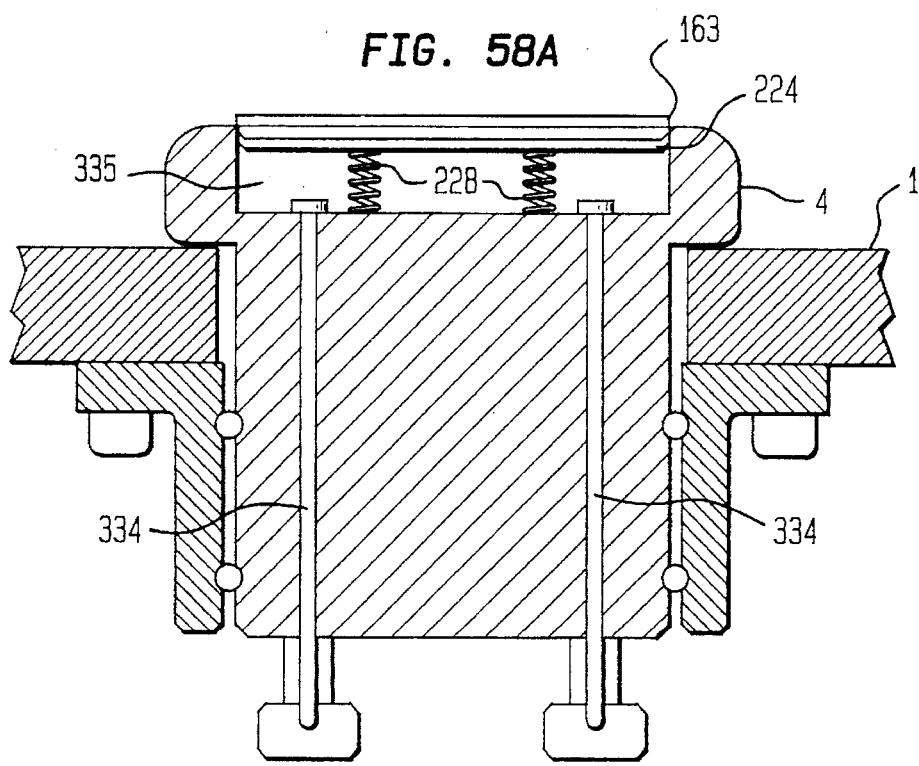
FIGS. 58A and B illustrate the lockup pin system of the tool nest used for label staking.
Figure 58B:
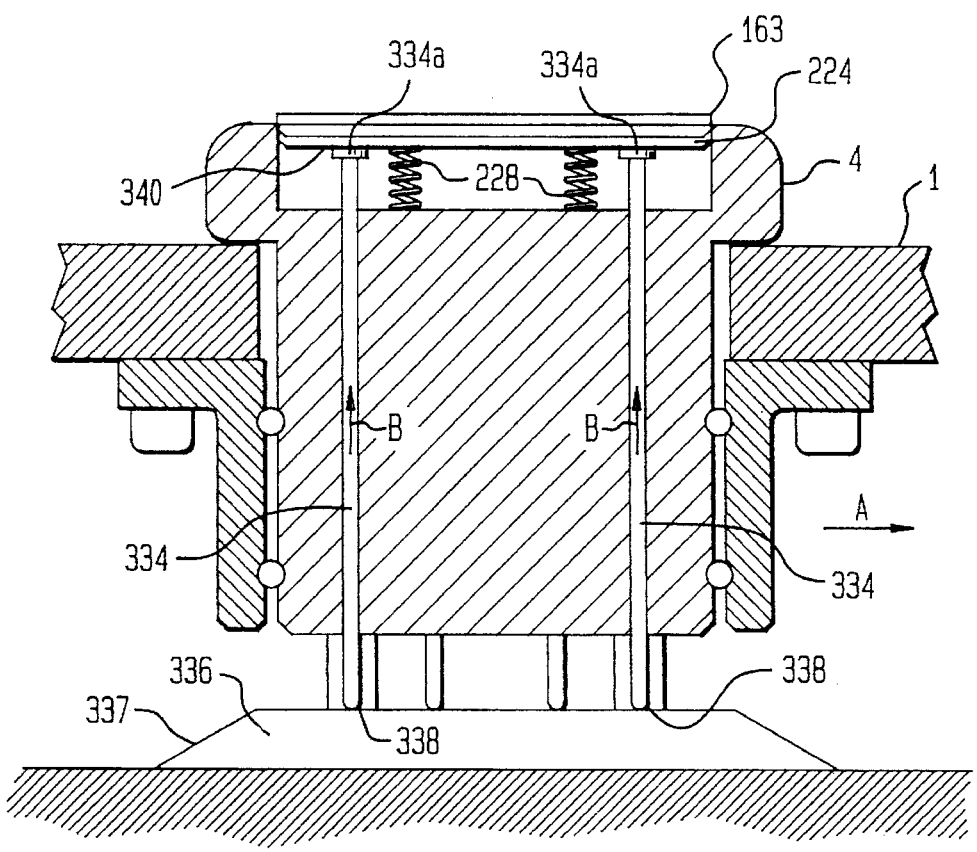

The downward staking force, as applied to package 12 in FIG. 56, is transmitted to lower tooling platform 224 which provides support therebelow. Referring to FIG. 58A, which illustrates only the tooling related to label attachment, platform 224 is, at all other machine stations, supported on springs 228 to provide a resiliency to nest 4 lower tooling. Deflection resulting from this spring support during the staking of tabs 72 is eliminated by lock up rods 334, extending from the area below tool nest 4 to the internal cavity 335 therewithin. When tool nest 4 is positioned by turret 1 at station VI, for label placement, as illustrated in FIG. 58, it moves in the direction of arrow A relative to stationary cam 336 mounted fixedly to the machine frame. As the dwell position for station VI, is approached, the upper ends 334a of lock up rods 334 are cammed upward, in the direction of arrows B, by the entrance ramp 337 of cam 336. This upward displacement results in the upper ends 334a of rods 334 bearing against the lower surface 340 of platform 224, thereby resisting the tendency of springs 228 to deflect, and assuring a rigidly supported platform 224 for the staking operation to be performed thereon.

Station (VII)

No operations are performed at station VII.

Station (VIII)

The function of machine station VIII illustrated in FIG. 59, is to unload the completed package 73 from tool nest 4 and place it into a product handling magazine tray 64. The function is also to reject, to a scrap container, any packages for which a fault was detected during the machine assembly sequence, based on an appropriate signal from the control computer. Still another function is to deliver, responding to a manually actuated command, the completed package, to a suitable pickup location easily and safely accessible to the person requesting it.

Figure 60A:
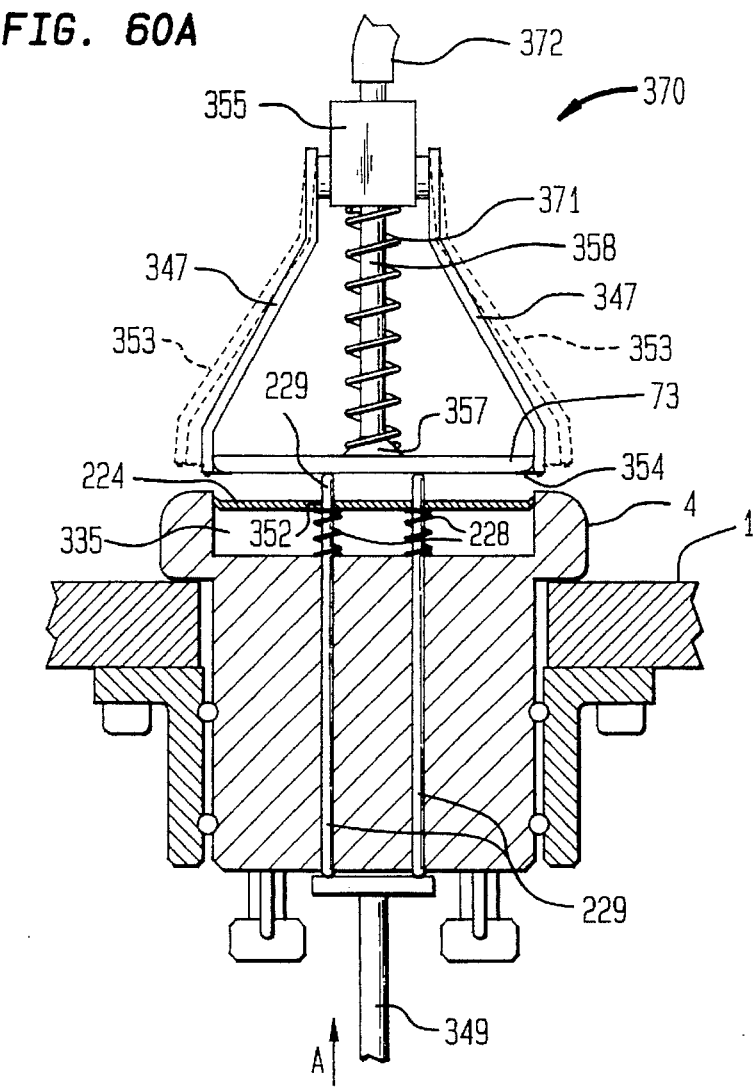
FIGS. 60A and B illustrate a sectioned elevation view of the mechanical pick-up gripper arms and interaction with the tool nest ejector pin function.

FIG. 59 illustrates a rectilinear slide assembly of similar construction and actuation as the assembly 285 illustrated in FIG. 46 for label placement. Mounted thereon are three gripper assemblies 348, 362, and 365, comprised of a commercially purchased pneumatically operated gripping module 355, a pair of gripping arms 347 attached thereto custom designed to accommodate the length of package 73, and vacuum cup and pipe assembly 370. Referring to FIG. 60A, gripper assembly 370 is comprised of rigid pipe 358 mounted slideably in body 355. The lower end of pipe 358 extends downwardly to a length generally coplanar with the lower ends of grippers 347, where vacuum cup 357 is attached thereto. A light spring 371 is assembled over pipe 358 to assist gravity in assuring that pipe 358 always slides to its lowest point of travel when vacuum cup 357 is not in contact with an object.

Figure 60B:
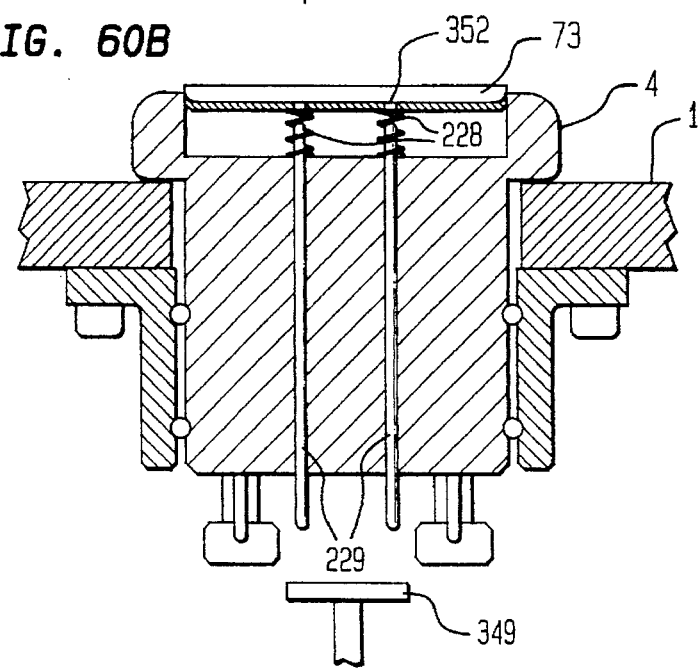

FIGS. 60A illustrates the interaction of gripper assembly 370 and tool nest 4 at the point of impending pickup of package 73. FIG. 60B illustrates the configuration of tool nest 4 as it is indexed into the machine station VIII position prior to the station off-load cycle in FIG. 60A. Initiating the off load cycle, in FIG. 60A, a "T" lifter 349, slidingly mounted in a housing in the machine frame (not shown) has been elevated to the position shown, in the direction of arrow A, by a cam operated in vertical displacement in the base of the machine. The "T" lifter 349 causes a corresponding vertical lift of ejector rods 229, slidingly mounted in tool nest body 351. Ejector rods 229 extend, at their upper ends 351, through clearance holes 352 in lower tool platform 224, and bear against the underside of package 73, thereby lifting it off of lower tool platform 224 so that gripper arms 347 can move from the open position 353 shown in dashed line, and grip around and below the package tray bottom as illustrated at 354 by closing to the position indicated by solid lines 347. Simultaneously, vacuum cup 357, mounted on vacuum pipe 358, is configured to grip the top surface of package 73. Gripper body 355 is, at the point illustrated in FIG. 60A, ready to be raised and thereby remove the package 73 from tool nest 4. Referring to FIG. 59, slide plate 356 has three gripper assemblies, 348, 362, and 373 attached thereto. The gripper assemblies are essentially identical in the gripping function described for FIG. 60A, but differ in mounting arrangement. Assembly 348 is mounted fixedly to slide plate 356 and oriented such that the open spread of gripper arms 347 is aligned with the arrow G, parallel with the long dimension of package 73 on tool nest 4. Gripper assembly 362 is mounted rotatably in block 364, rotatable about axis 363, and controlled in rotational orientation by link arm 365 and radius arm 366 such that the open spread of gripper arms 374 is initially aligned with arrow G. FIG. 59a illustrates the relative motion of the assembly, and when slide plate 356 has been displaced as indicated by arrow D to the left hand Stroke position "I", and the assembly 362 is rotated 90° or perpendicular to arrow G when displaced as indicated by arrow A to the right hand stroke position "II". This rotational capability enables gripper 362 to pick up a package from station 359 and deposit it in a rotated 90° orientation at station 360. An array of tapered pins 344 is fixedly mounted at the location 360 loosely beyond the periphery of package 345 to assure stability therein. An electronic demagnetizing element under package 345, represented in FIG. 59 by dashed outline 343, is configured to remove any residual magnetism in the needle within package 73b. Gripper assembly 373 is fixedly mounted on slide plate 356 oriented rotationally so that the open spread of gripper arms 375 are aligned 90° with arrow G, and thereby aligned with the longitudinal dimension of cavity 361 in magazine transport tray 64.

Referring to FIG. 59a, slide plate 356 is driven in a rectilinear motion pattern indicated by arrows A, B, C, D, E, F. This motion, in concert with synchronized gripping and releasing, results in one sequential advancement of the unloaded package 73, for each machine cycle, in the direction of arrow A, to first the select/reject station 359, then to pre-positionfor magazine load station 360, and finally into magazine tray cavity 361.

Select/reject station platform 359 is configured, on command from the control computer, to slide in the direction of arrow H, driven by a pneumatic cylinder, not shown, such that the package released by grippers 374 will drop into scrap chute 376 leading to a scrap container under the machine. This function is enabled when a package that has failed any of the quality tests performed automatically by sensors and vision systems described hereinabove is transferred through this station.

Platform 369 will also, on command of the machine control computer, slide in the direction of arrow H after a package has been there deposited and is cradled within the array of pins 399, and deliver it to a pickup spot and manually removed.

Figure 61:
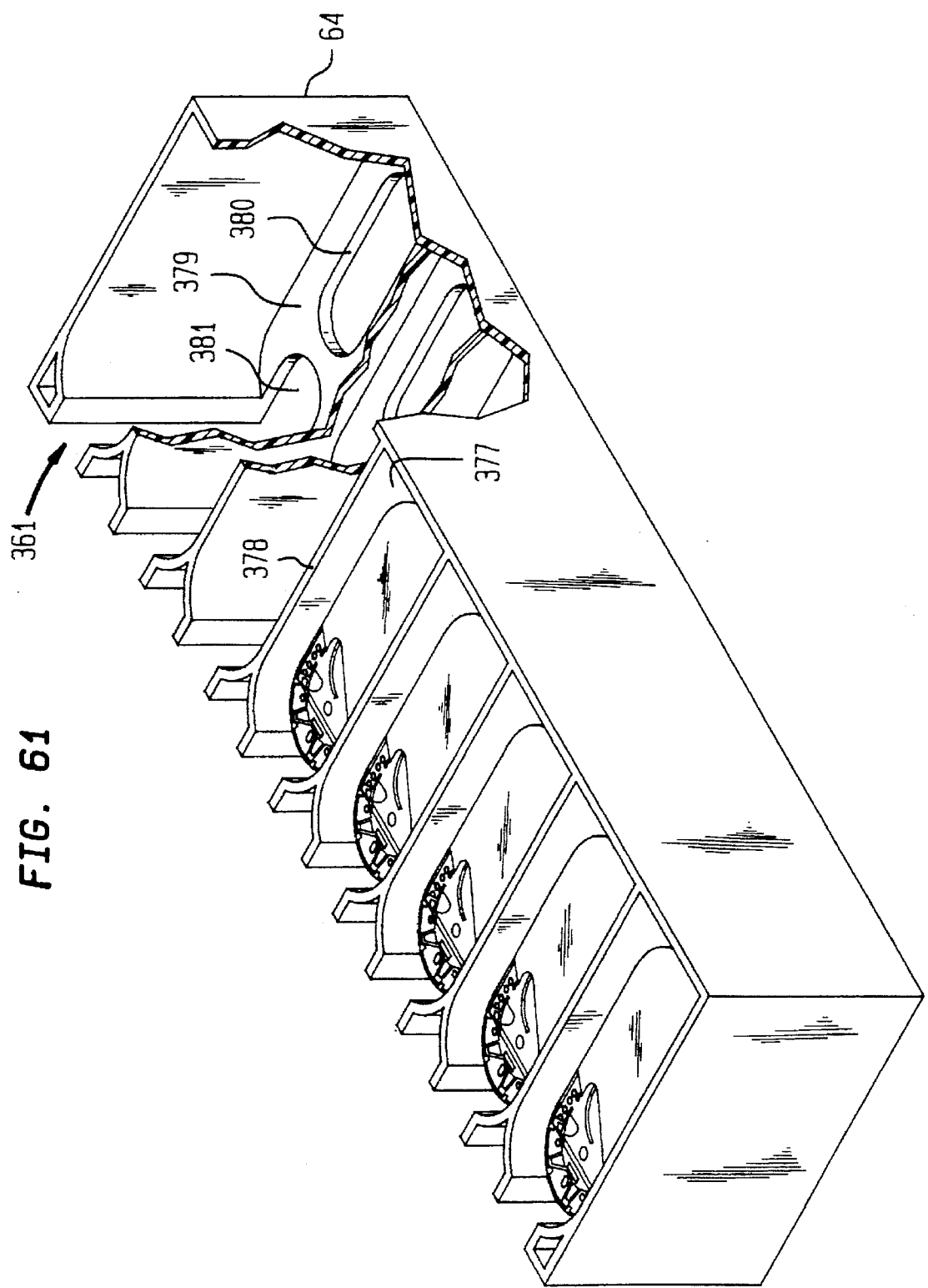
FIG. 61 illustrates the machine off-load magazine tray.

Select/reject station platform 359 will normally remain stationarily positioned as illustrated in FIG. 59, and the package there deposited picked up by gripper assembly 373 and placed in the magazine tray 64 with other finished product. The magazine tray 64, illustrated in FIG. 61 is used to protect assembled suture package trays and retain them in a properly oriented position for automated processing through the production operations that follow the machine described hereinabove. Tray 64 is comprised of a plurality of cells 377 defined by vertical walls 378, and a floor 379 with two access openings 380 and 381 therein. Opening 380 provides clearance for a bottom lifting elevator if needed for automatic feeding of subsequent operations. Opening 381 provides finger grip access for manual feeding of subsequent operations. The underside (not shown) has a downwardly projecting cross rib for each cell to enable accurate position registration by downstream automated production equipment fed from this magazine tray. The arrangement of the magazine automatic loading system in the winding machine described hereinabove is illustrated in FIG. 10. Empty magazines are loaded in single height in-feed conveyor row 382 where they are moved in the direction of arrow H by conveyor 383. Empty magazines 64 that reach point 384 are engaged by a cross feed system 385 that advances magazine trays laterally, in the direction of arrow G, one cell at a time, for the loading operation illustrated in FIG. 59. When full, magazine trays continue to be advanced laterally in the direction of arrow G until reaching point 386, whereupon exit conveyor 387 moves them in the direction of arrow J, for manual unloading therefrom.

OPERATION OF THE MACHINE FOR THE AUTOMATED PACKAGING OF NEEDLES WITH ATTACHED SUTURES

The following description is directed toward operation of the foregoing mechanisms, starting with loading an empty molded package tray and bundle of unwound sutures, and ending with off-load of the magazine tray containing assembled and complete packages therein.

Operation of Machine Station (I)

The machine operator 63, illustrated in FIG. 9, obtains stacks of empty package trays 12 received from the molding supplier, and loads the tray carrousel 30, as illustrated and described with respect to FIG. 15, by opening the doors 36 and 37, and lowering stacks 31 of trays into the vertical chambers 32 that are positioned near the doors 36 and 37.

The operator 63 manually initiates the carrousel transmission drive motor with a control switch (not shown) which causes an incremental rotary index of carrousel about axis 33 clockwise, as indicated by arrow D, thereby bringing the next empty vertical chamber 35. The operator loads chamber 35 and continues in this index and load sequence until all chambers from door 36 to and including the chamber in position 5 are filled. The operator 63 initiates the cycle start control (not shown), causing turret 1, illustrated in FIG. 9, to incrementally index counterclockwise about axis 2 until tool nest 4 is opposite the tray loading carrousel and the dispensing mechanism associated therewith. The control computer activates the tray shuttle 39, illustrated in FIG. 16A, to extend as illustrated, in the right hand direction of arrow A, carrying a short stack 47 of trays 12 in the shuttle pocket 123 to a position under vacuum cup assembly 53. The slide assembly 69 lowers vacuum cup assembly 53 so that the vacuum cup 48 thereon contacts and grips the top tray in pocket 123, illustrated in FIG. 16B. The slide assembly 69, translates vacuum cup assembly 53 and tray 12 gripped thereon in the direction of arrow C as illustrated in FIG. 16c to a position over tool nest 4 on turret 1. The slide assembly 69 descends, indicated by arrow D, in FIG. 16D, and presses the tray 47 onto tool nest 4, pressing the pilot hole 205 illustrated in FIG. 2 in tray 12 interferingly over the enlarged base of the pilot pin 203 (shown in detail in FIG. 14B) and the tooling thereon illustrated in FIGS. 14A and B. Simultaneously, the shuttle 39 is translated to the left, indicated by arrow E, into the carrousel base 40, enabling the tray stack 31 to drop, in the direction of arrow F, thereby replacing the tray just removed from the shuttle pocket 123, to enable the assembly to repeat the foregoing cycle. As tray stacks are emptied, the carrousel indexes filled replacements over the shuttle 39, and the operator re-fills the empty tray chambers when they are adjacent to re-fill doors 36 or 37 as illustrated in FIG. 15.

Operation of Machine Station (II)

Figure 19:
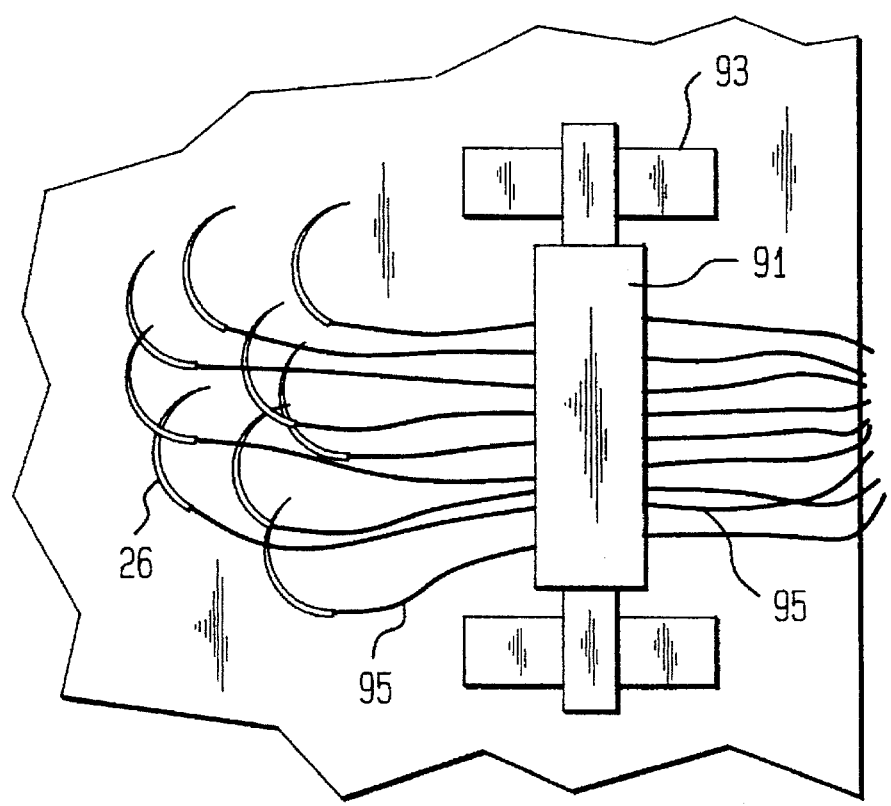
FIG. 19 is a plan view of the suture bundle tensioner illustrated in FIG. 18.

Referring to FIGS. 9 and 17, the machine operator 63 places a bundle Of surgical needles and attached sutures 95 into bundle tensioner 67 so that the needles 26 lay generally flat, but not precisely oriented, on loader plate 68. The operator 63 places tensioner weight 91 into slot 92 of tensioner body 93 causing resilient surface 94 to bear against suture strands 95, as illustrated in FIGS. 18 and 19. One single needle 26 with an attached suture is identified by operator 63 and slidingly moved, by finger or pencil like instrument (not shown) across the loader plate 68 toward needle pocket 97, and placed therein.

Imprecise placement of the needle 26 in the t5 needle recess 102, as illustrated in FIG. 21, results in gap 112 between needle end stop 104 and needle butt end 27. A vacuum opening 111 in suture groove 105, ported to a vacuum source below needle wheel 98 (not shown), engages and secures the suture 28 in the suture groove 105. As the needle wheel 98 advances in incremental clockwise rotation, suture displacement slide 106, illustrated in FIG. 22, is cammed radially outward in the direction of arrow A, causing the suture displacement pin 107, to pull taut any slackness in suture strand 28 between the needle 26 and the bundle tensioner 67 as illustrated in FIG. 17. Continued radial displacement of the pin 107 exerts a pulling force on the needle 26, causing it to slide rotatingly counterclockwise in needle recess 102 until needle butt end 27 comes to rest upon the needle end stop 104. The needle 26 is now precisely positioned in the recess 102 for needle pickup and insertion in package tray as described hereinbelow.

As continued incremental clockwise rotation of the needle wheel 98 results in the needle pocket 97 reaching about the 4 o'clock position of FIG. 17, a suture displacing device 119 plunges roller 120 over the span of suture strand between adjacent slides 106 and 107, and descends downwardly with sufficient stroke to form a loop in the suture 118 spanning therebetween, fully withdrawing the trailing end of the suture out of bundle tensioner 67 and avoiding potential tangles that can occur in the suture bundle if an excessive number is being withdrawn at the same time.

After the needle pocket 97 has advanced rotationally on the needle wheel 98 to the position indicated by pocket 132, the needle with attached suture 25 therein is ready for transfer, by the transfer bar assembly 125, to the molded tray 12 on the tool nest 4 on turret 1. A magnetic metal detector 110 senses any empty needle pockets 97, and causes the computer control system to initiate additional index cycles of the needle wheel 98 until a needle with attached suture is present in the needle pocket 132 in preparation for transfer to turret 1.

Referring to FIG. 23, the cross bar 275 of transfer bar assembly 125 descends in the direction of arrow C, causing the needle grippers 126, FIG. 27, to enter the needle pocket clearance grooves 108 and straddle the needle 26. The vertical closing rod 129 illustrated in FIG. 24A rotates clockwise, causing the radius arm 130 fixed thereto to rotate in the direction of arrow A, to laterally displace the closing push rod 156 to the right, indicated by arrow C. Referring to FIG. 24B, looking from the opposite side of transfer bar 125, the closing push rod 156 in this view is displaced to the left, in the direction of arrow E, causing the push rod rack 150, engaged with the gripper operating gear 140, to rotate the gripper cam 139 90°, thereby enabling the gripper spring 131 to move the gripper block 135, slidingly along shaft 136, to the right, in a direction opposite arrow C. An identical, but in mirror image, motion is imparted to gripper block 145. The needle grippers 126 are resultingly closed, by spring force, on the needle 26.

The transfer bar 125 elevates, in the direction opposite to arrow C in FIG. 23, and rotates 180° counterclockwise, in the direction of arrow B, as the main turret 1 simultaneously indexes in the direction of arrow A, thereby advancing the tool nest 4 from the tray loading station 1 to the needle loading station 2 illustrated in FIG. 23. The transfer bar assembly descends, as illustrated in FIG. 24A, arrow B, and the gripped needle 157 enters the needle park of the package tray 12. The downward thrust of the needle grippers 126 forces the needle 26 into the plastic needle park 84 of tray 12 sufficiently to deform the blades 85, as illustrated in FIG. 5, thereby securing the needle 26. As illustrated in FIG. 24A, the needle grippers 126 are opened, resulting from rotation of opening rod 159 causing radius arm 160 to press the opening plunger 147, bearing on the face 166 thereof, and the transfer bar raised as in the foregoing description.

Operation of Machine Station (III)

Figure 30:
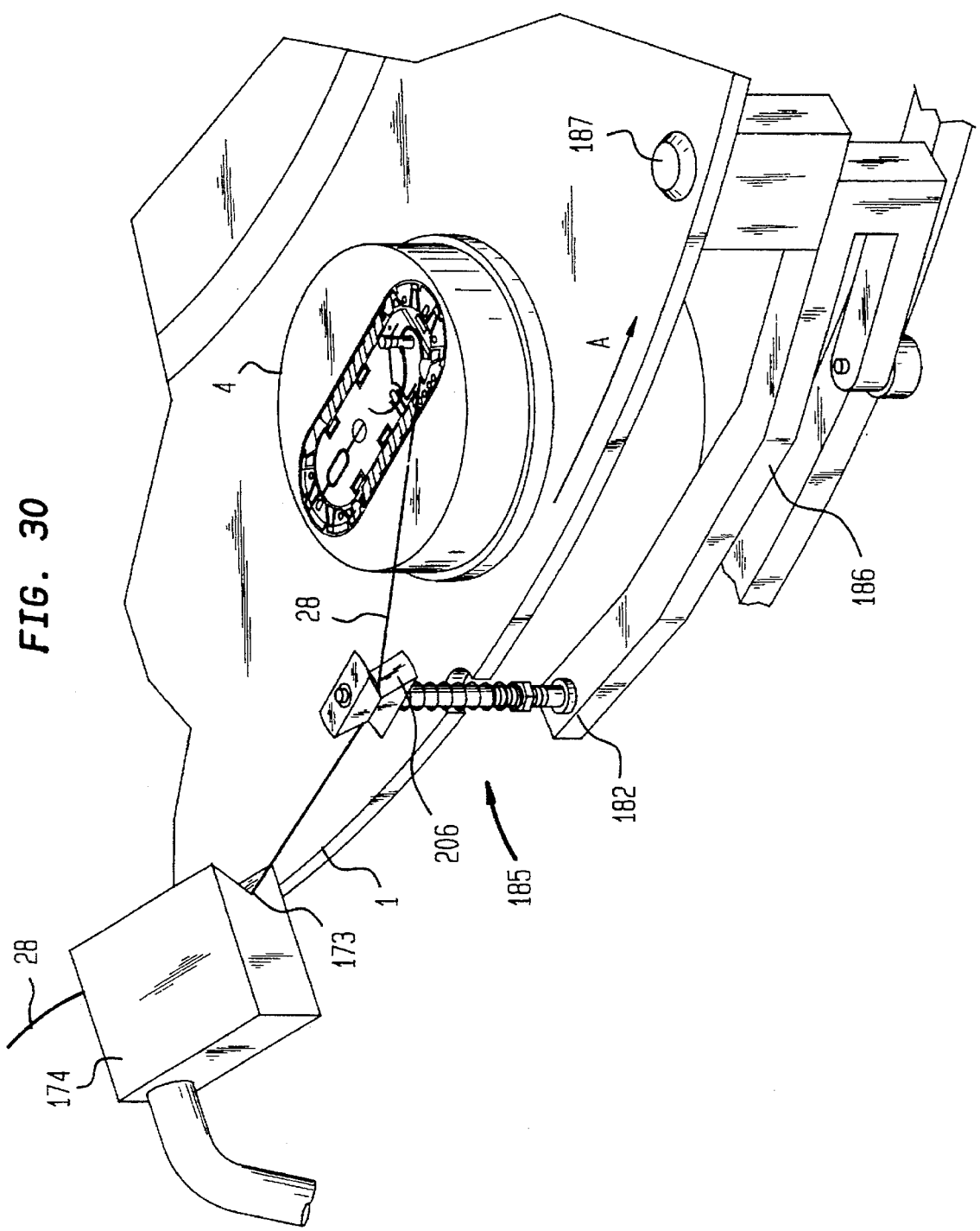
FIG. 30 illustrates an isometric view of machine station III and the post tensioner arm arrangement.

Referring to FIG. 23, as the main turret 1 incrementally indexes the tool nest 4 from station II to station III, the trailing suture length 28, is pulled axially by the needle 26, now secured in the needle park of tray 12, from a path which extends, rearwardly, across a suture protective pan 170 and, in a rearward direction with respect to its movement, along the peripheral region 171 of the needle wheel 98. During this index of the turret 1 from station II to station III, and the resultant pulling of the suture 28 therefrom, the path of the suture 28 is led under a stationary guide 172, and into the "V" of the vacuum tensioner 174. With reference to FIGS. 29, 30, 31 as described in detail hereinbelow, the path of the suture 28 has at this point of travel become essentially tangential to turret 1, by virtue of the indexed incremental rotation of the mail turret 1, entering it into the lead-in conical surfaces 206 of the post tensioner 185, which moves in indexed rotation therewith. As the post tensioner 185 sweeps toward turret position (3), in the direction of arrow A, the plunger 191 thereatop comes in contact with a stationary cam 184 (FIG. 31), thereby opening the lower tension cone 192, causing the suture 28, in tension due to the drag force of the vacuum tensioner 174, to enter between the parallel cone faces 199 and 200. As turret 1 continues in rotational index, the plunger 191 of the tensioner 185 moves out from under the stationary cam 184, and the suture 28 is thereby exposed to the frictional tension force of the bottom cone 192 pressure imparted by the spring 195.

Figure 33:
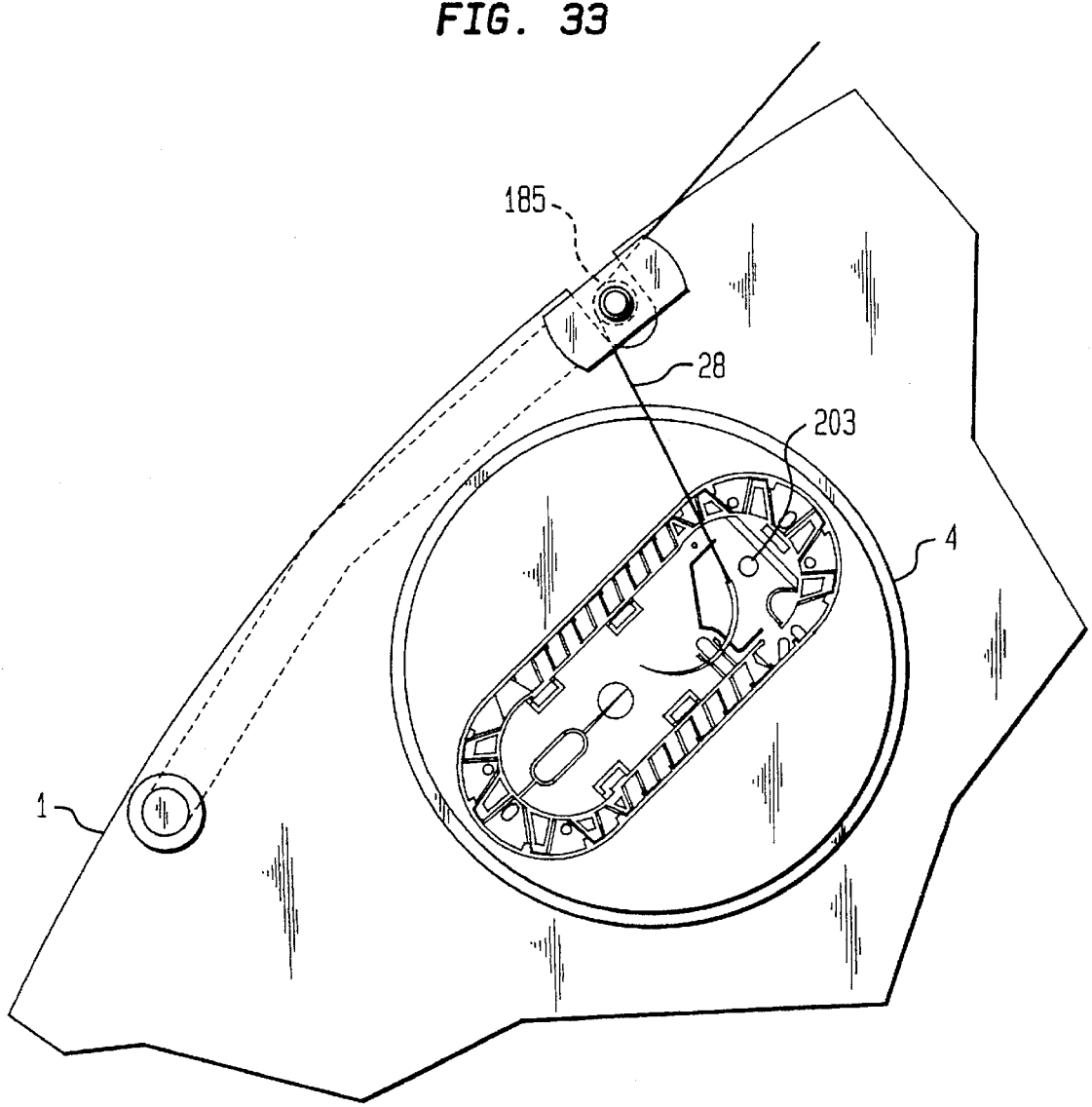
FIGS. 33, 34, and 35 illustrate three successive steps of the 180° pre-wind sequence at station III.

The main turret 1 completes its index cycle, causing the tool nest 4 to dwell at machine station III as illustrated in FIG. 33. A 180° counterclockwise rotation of tool nest 4 is initiated to the position illustrated in FIG. 34, stopping in the configuration of FIG. 35. This wraps the suture 28 around the pilot pin 203, and positions the suture span therefrom to the tensioner 185 approximately in line with the entrance gap 81 in the suture channel 79 of the tray 12, thereby preparing it for the winding operation to follow. A digitizing camera 207, illustrated in FIG. 29, working in concert with image analysis electronics in the machine control cabinet 65, automatically inspects the tool nest 4 for presence of a molded tray 12 and presence of a needle 26 in the needle park 85, as illustrated in FIG. 27.

Operation of Machine Station (IV)

As illustrated in FIG. 36, the main turret 1 indexes the tool nest 4 into position for completion of the wind. This illustration is a plan view, with the winding station hardware above the turret removed for visual clarity. The winding tooling 230 and 235 above the tool nest 4 is open, as illustrated in FIG. 41, in that upper tool platform 230 is not down and in contact with the tool nest 4 surface. As the index of turret 1 comes to rest at this station, a cam follower 213 attached integrally to the tensioner arm 186 is cammed up the entrance ramp 212 of stationary cam 211, thereby causing the arm 186 to rotate in the direction of arrow G pivotally about point 215 in turret 1. The foregoing movement of tensioner arm 186 and post tensioner 185 mounted thereon, with respect to the pilot pin 218 in tool nest 4 aligns the suture span therebetween precisely within the gap 81 in the suture channel 79 of the tray 12.

Referring to FIG. 42, the plate cam 390 is continuously driven when the machine is in operation. The electronic vision system of station III has verified that a tray 12 is on the tool nest 4, after indexing the control computer signals to initiate a winding cycle at station IV, and resultingly the station lockout pneumatic cylinder 394 to retract piston rod 396 to the position indicated in solid line 395. As the plate cam 390 rotates in the direction of arrow C, the cam follower 392 falls off the rise portion into the low point 391, thereby causing lever 254 to descend, resulting from tension in the operating spring 183, in the direction of arrow B, pivoting about its mounting pin 256. This downward motion is transmitted through the connecting link 255 to the vertical slide rod 253, and also to the horizontal yoke 252 affixed thereto, causing the upper winding tooling 230 and 235, mounted rotatingly thereon, to descend and close on the tray 12 in the tool nest 4. The resulting interaction of upper and lower winding tooling is illustrated schematically in FIG.

38. As the upper tooling platform 230 is lowered onto the lower tooling platform 224, a portion of the underside 282 of the upper platform contacts the tray 12 (contact point not shown), causing it to also descend in the direction of arrow B, resultingly causing the tip 223 of the blade 225 to plastically deflect the upper channel finger 86 up, in the open position, hingedly about its anchor point 66. The downward travel of the upper tool platform 230 also brings its contoured surface 271 near the opposing contoured surface 272 of the lower tool platform 224, so as to result in a gap 283 of greater than one but less than two suture diameters therebetween. The control computer energizes the servomotor (not shown) driving the rotation of the tool nest 4 by the arrangement previously described. As the tool nest 4 rotates, the suture 29 is pulled through the post tensioner 185 illustrated in FIG. 36 and wound in flat, layered loops 219 (shown also in FIG. 5). The resulting tension in the suture 28, during winding, is partially shunted from the needle 26 by a spring loaded foot 266, as described with respect to FIG. 40A, clampingly bearing on the suture 28 within the gap 268 therebeneath. This foot also assures the suture entry loop 270 is close to and drawn under the tray shelf 221 by vacuum induced air entering through the slot 269 in the tray 12. Dislodging of the needle 26 which may result from tension transmitted from the suture 28, is prevented by a second "C" shaped pressure foot 264, bearing downwardly thereon, and acting to further seat the needle 26 in the needle park 85.

Referring to FIG. 38, as the winding operation draws the full length of the suture 29 into the package, the trailing end of the suture pulls free of the post tensioner 185, causing the lower projection 208 of the distal end of the tail tucking stylus 233, engaged in the lower stylus groove 284, to plow the trailing end into the suture channel 79 of the tray 12. Control of the trailing end of the suture 26 is assisted by air velocity, in the direction of arrow A, resulting from vacuum piped to the underside of the tool nest 4. At the end of the winding operation, the winding plate cam 390, illustrated in FIG. 42, rotates toward the rise lobe and begins to vertically open the winding tooling by lifting the cam follower 392 and the arm 254 attached thereto in the direction of arrow A. Simultaneously, a push rod 247, illustrated in FIG. 41, is raised by a second cam (not shown) causing an operating lever 248 to pivot about a pivot shaft 249 and resultingly cause a cam roller 250 attached on the distal end of the lever 248 to displace downward a plate 238 mounted on a vertical rod 245 mounted slidingly in a mounting structure 246. Downward movement of this plate 238 causes corresponding downward travel of closing pins 232, illustrated in FIG. 38, which press package channel finger 86 down, thereby assuring the final position thereof is at or below its original horizontal orientation with respect to the opposing structure 76 of the suture channel 79 in the tray 4. The plate cam 390, illustrated in FIG. 42, continues to open the winding upper tooling by the foregoing described sequence. The tool nest 4 at this point has a wound package 163 thereon at the assembly stage, and is ready to be indexed by the main turret 1 to the next operation. During this index of the turret 1, the re-set mechanism illustrated in FIG. 45 rotates the upper winding tooling 180° in preparation for the next winding cycle.

Operation of Machine Station (V)

The machine station V has a digitizing camera aimed vertically downward, similar to camera 207 in FIG. 29, producing a plan view of the tool nest 4 for electronic inspection. Detectable faults are a missing needle 26, a missing package tray 12, any portion of the suture loop 270 not under the suture track shelf 221 or outside the overall perimeter of the tray 12. A detected fault will cause rejection of the package at machine station VIII.

Operation of Machine Station (VI)

Prior to starting production on the packaging machine, the operator or other designated individual will have filled a stack of label covers 71, into a label magazine 286, as illustrated in FIG. 47, placed it in the magazine shuttle 291, illustrated in FIG. 46, and electrically activated machine station VI. The shuttle 291 moves the magazine 286 to the position illustrated. The slide assembly 285 moves the first vacuum cup assembly 315 over the magazine 286, descends in the direction of arrow A, secures a vacuum grip on the top label 71, raises in the direction of arrow A, translates in the direction of arrow B, and lowers the label 71 on the intermediate station 287. Vacuum is maintained on the cup assembly 315 and a stronger vacuum on the station 287. As the slide assembly 285 raises to repeat the motion for the next cycle, the intermediate station 287 is exposed to two opposing vacuum grips, thereby separating the labels if two are stuck together at this point of the station operation. On the next index cycle of slide assembly 285, as illustrated in FIG. 54, the vacuum cup assembly 314 is lowered over the intermediate station 287 and grips the label 319 therein, and repeating the foregoing rectilinear motion, transfers the label 71b to the pre-form station 288.

On the next cycle of the slide assembly 285, illustrated in FIG. 57A, vacuum pickup assembly 313 descends on the pre-form station 288 and, progresses with a limited downward stroke indicated by arrow A, in FIG. 57B, causing the stripper plate 323 to clampingly engage the anvil 329 with the label 71 therebetween. The staking punches 325 break the tabs 72 free of the flat material of the label 71, and displace them partially into the anvil wells 333. Vacuum through hose 341 is supplied to pipe 342 and the label 71 is thereby gripped by the stripper plate 323 as the upper tool block 326 is raised by the slide assembly. The stripper springs 331 assure that the punches 325 are withdrawn, thereby not interfering with the vacuum grip on the label 71. The slide assembly 285, illustrated in FIG. 56 raises, translates in the direction of arrow B, and descends in the direction of arrow A, on the wound package 163 on the tool nest 4. The tab staking operation is similar to the pre-form operation above, with the exception that the molded tab pockets 165 in the package molding 12 of wound package 163 are in the place of the anvil wells 333, and the downward staking stroke, arrow A, is greater, causing the staking punches 325, to fully set the tabs 72 to the latched configuration illustrated in FIG. 57D and described and illustrated for FIG. 8. The completed package 73 resulting from the label assembly operation performed by station 6 is illustrated in FIG. 7. The index of the tool nest 4 into station VI by the main turret 1 causes lockup rods 334 illustrated in FIG. 58B, to rise on the stationary cam 336 positioned for this purpose, and vertically support the lower tool platform 224, thereby preventing deflection of the platform springs 228 from the staking operation downward forces.

Operation of Machine Station (VII)

No operations are performed at machine station VII.

Operation of Machine Station (VIII)

Referring to FIG. 59, the slide assembly at station VIII operates in a similar rectilinear motion pattern to station VI.

The first gripper assembly 348 descends over the tool nest 4 with the assembled package 73 thereon. The package is lifted from the tool nest 4 as illustrated in FIG. 60A. A cam driven mechanical motion within the machine base (not shown) elevates "T" lifter 349, indicated by arrow A, thereby elevating ejector rods 229 in tool nest 4, which rise through the clearance holes 352 in the lower tool platform 224, vertically lifting the package 73 therefrom. Simultaneously the gripper body 355 is lowered by the slide assembly 346, so as to position the gripper arms 353 attached thereto in proximity of the long dimension peripheral edge of package 73. The gripper arms close and clamp thereon, indicated by solid lines 347, as vacuum cup 357 simultaneously grips the top surface of the package 73.

Referring to FIG. 59 and 59A, the slide assembly raises through a vertical stroke, arrow F, translates through a horizontal stroke, arrow A, and descends, arrow B. The package 73 is deposited on select/reject station 359 by reversing the gripping procedure (i.e., opening) and interrupting the vacuum source on cup assembly 370. If the package 73 has failed an automatic inspection any place in the assembly processes upstream, a signal will cause the station platform 359 to translate in the direction of arrow H, thereby causing the package 73 released by gripper assembly 348 to drop into scrap chute 376 and a collection bin therebelow. If a sample is requested by a control button command, platform 359 slides in the direction of arrow H after the package 73 is deposited thereon, and parks in a suitable location for manual removal. Otherwise, the package 73 will remain on the platform 359 and be picked up by the second gripper assembly 373, rotated 90° as the slide assembly 346 translates in the direction of arrow A, causing the link 365 to rotate the arm 366 and the gripper body 362 through the vertical shaft 369 attached thereto. The package 736 in the last station 360 is picked up by the third gripper assembly, and deposited in the magazine tray cavity 361 of the magazine 364.

Prior to starting production in the machine, an operator or other designated individual loads empty magazine trays 64 into the infeed section 382 illustrated in FIG. 10 of the magazine shuttle and load system. The infeed conveyor advances empty magazines in the direction of arrow H until they back up against a stop surface at 384. A cross feed tray advance system 385 indexes the magazines 64 in the direction of arrow G, one cavity at a time, activated by a control system that responds when the correct count of packages is loaded in the cavity. Full trays advance in the direction of arrow G until reaching the end of lateral travel 386, signaling exit conveyor 387 to advance the magazine in the direction of arrow J. When the exit magazine row is filled with loaded magazines, they are manually removed.

While several embodiments and variations of the present invention for an automated rotary packaging machine are described in detail herein, it should be apparent that the disclosure and teachings of the present invention will suggest many alternative designs to those skilled in the art, and that the present invention is defined by the following claims.

We claim:

1. A semi-automated machine for assisting an operator in singulating and feeding a needle having a suture attached thereto to an automated workstation, said machine comprising:

(a) a first horizontal work surface for receiving a plurality of needles having sutures attached thereto;

(b) a horizontal and planar rotatable feed wheel for assisting an operator in singulating a needle and attached suture from said plurality, said feed wheel having a plurality of needle receiving pockets formed about an outer circumference thereof;

(c) a robotic needle handling device for picking needles and attached sutures from said rotatable feed wheel, and positioning said needle and attached suture at a defined location for subsequent operations by an automated workstation;

(d) means for synchronizing the rotation of said rotatable feed wheel with the picking of said robotic needle handling device;

whereby an operator at said machine may slide individual needles from said horizontal work surface to a needle receiving pocket on said feed wheel as said feed wheel is rotated.

2. A semi-automated machine as claimed in claim 1, wherein said robotic needle handling device includes a rotatable tower with a gripping means for inserting one of said needles and attached suture into a package tray carried by said automated workstation.

3. A semi-automated machine as claimed in claim 2, wherein said rotatable tower includes first and second gripping members for successively gripping, engaging and conveying individual needles in successive sequence towards individual package trays in synchronism with the automated workstation.

4. A semi-automated machine as claimed in claim 3, wherein said first and second gripping members each include cam driven needle clamping jaws.

5. A semi-automated machine as claimed in claim 4, wherein said cam driven needle clamping jaws are spring biased to a closed position, and opened by a cam.

6. A semi-automated machine as claimed in claim 5, wherein said cam is driven and said tower is rotated by a single drive means.

7. A semi-automated machine as claimed in claim 1, wherein said first worksurface defines a planar worksurface that is coplanar with a plane defined by said rotatable feed wheel.

8. A semi-automated machine as claimed in claim 7, wherein said first worksurface includes an arcuate edge which matches a circumference of the rotatable feed wheel and is positioned adjacent thereto.

9. A semi-automated machine as claimed in claim 8, wherein said arcuate edge and circumference of the rotatable feed wheel define a gap therebetween that is less than a diameter of the needles to be singulated, so that the operator may slide needles from the first horizontal work surface to the horizontal rotatable feed wheel when the needles are singulated.

10. A semi-automated machine as claimed in claim 1, wherein said machine further comprises a bundle tensioner mounted on said first worksurface for receiving a bundle of the plurality of sutures attached to said plurality of needles.

11. A semi-automated machine as claimed in claim 10, wherein said bundle tensioner includes a weighted member which is placed on said plurality of sutures to tension a suture when the needle to which the suture is attached is singulated by said operator and advanced by said rotatable feed wheel.

12. A semi-automated machine as claimed in claim 1, wherein said needle receiving pockets are removable from said rotatable feed wheel.

13. A semi-automated machine as claimed in claim 12, wherein said needle receiving pockets are provided in matched sets for said rotatable feed wheel, with the pockets of each set having a needle receiving recess which is needle size specific and corresponds to a range of sizes of needles to be singulated.

14. A semi-automated machine as claimed in claim 13, wherein each of the needle receiving recesses in a set defines a loose needle clearance for the range of sizes of needles to be singulated which will allow imprecise placement by the operator when the needle is singulated.

15. A semi-automated machine as claimed in claim 14, wherein each of said needle receiving recesses defines a registration point for a needle placed in the recess.

16. A semi-automated machine as claimed in claim 15, wherein said pocket further defines a suture recess which opens into said needle receiving recess, and said registration point is a needle stop formed at a juncture of said needle receiving recess and said suture recess.

17. A semi-automated machine as claimed in claim 15, wherein said rotatable feed wheel includes a reciprocal suture tensioner for each needle pocket which reciprocates in synchronization with rotation of the rotatable feed wheel to draw the needle to the registration point within said recess.

18. A semi-automated machine as claimed in claim 17, wherein said machine further comprises a bundle tensioner mounted on said first worksurface for receiving a bundle of the plurality of sutures attached to said plurality of needles.

19. A semi-automated machine as claimed in claim 18, wherein said bundle tensioner includes a weighted member which is placed on said plurality of sutures to tension a suture when the needle to which the suture is attached is singulated by said operator and advanced by said rotatable feed wheel, said bundle tensioner and said suture tensioner cooperating to draw said needle to said registration point at a predetermined point of rotation of said rotatable feed wheel.

20. A semi-automated machine as claimed in claim 1, wherein each of said needle receiving pockets are formed of plastic, and said machine includes a needle-detecting device in a path of rotation of said needle receiving pockets, said needle-detecting device providing a signal to a control means for said robotic needle handling device, to allow said rotatable feed wheel to index one position between needle picks when the needle-detecting device determines that no needle is present in the needle receiving pocket.

21. A semi-automated machine as claimed in claim 20, wherein said needle detecting device is a metal sensor.

22. The combination of a needle feed wheel and a needle transfer mechanism, said combination comprising:
 (a) a worksurface for receiving a plurality of needles and attached sutures from a supply source, said worksurface providing a horizontal work surface for an operator to singulate a single needle and attached suture for semi-automatic placement,
 (b) a horizontal and rotatable needle feed wheel having a plurality of needle pockets spaced about an outer circumference thereof for sequentially receiving a plurality of needles and attached sutures as they are singulated from said supply source,
 (c) a needle transfer mechanism having first and second gripping members for sequentially removing an individual needle and suture from one of said needle pockets and inserting said needle into a needle-clamping member formed in a packaging tray for subsequent packaging.

23. The combination as claimed in claim 22 which further includes a bundle tensioner mounted on the worksurface for receiving a bundle of the plurality of sutures attached to said plurality of needles.

24. The combination as claimed in claim 23 which further includes a plurality of reciprocal suture tensioners mounted on said needle feed wheel with a single tensioner for each needle pocket, each of said suture tensioners reciprocating in synchronization with rotation of the needle feed wheel and a drag exerted by said bundle tensioner to draw the needle in said pocket to a registration point within said pocket.

25. The combination as claimed in claim 24 wherein said needle receiving pockets are provided in matched sets for said needle feed wheel, with the pockets of each set having a needle receiving recess which is needle size specific and corresponds to a range of sizes of needles to be singulated.

26. The combination as claimed in claim 25, wherein each of the needle receiving recesses in said matched set defines a loose needle clearance for the range of sizes of needles to be singulated, which clearance will allow imprecise placement by the operator when the needle is singulated.

27. The combination as claimed in claim 26, wherein each of said needle receiving recesses includes a needle end stop to define said registration point for a needle placed in the pocket.

28. The combination as claimed in claim 22 in which the needle feed wheel is incrementally rotated in a step wise manner and said needle transfer mechanism includes a rotatable tower with a transverse arm having first and second ends, with said first gripping member mounted on said first end and said second gripping member mounted on said second end, wherein said tower is rotated 180° for each incremental step rotation of the needle feed wheel.

29. The combination as claimed in claim 28, wherein said first and second gripping members successively grip, lift and convey individual needles in successive sequence to individual package trays in synchronism with the rotation of the needle feed wheel.

30. The combination as claimed in claim 29, wherein said first and second gripping members each include a pair of cam driven needle clamping jaws.

31. The combination as claimed in claim 30 wherein said cam driven needle clamping jaws are spring biased to a closed position, and opened by a cam.

32. The combination as claimed in claim 31, wherein said cam is driven and said tower is rotated by a single drive.

33. The combination as claimed in claim 29, wherein each of said needle pockets define at least one needle recess for receiving a needle and a jaw receiving recess transverse to the needle receiving recess, said jaw receiving recess enabling said tower to drop one of said gripping members into said needle pocket to engage said needle and lift it from said needle recess and said pocket.

34. The combination as claimed in claim 33 in which a vertical movement of said tower enables said first gripping member to park a needle in said package tray while said second gripping member is engaging a needle in a needle pocket.

35. The combination as claimed in claim 33 wherein said pocket defines three recesses and each of said gripping members includes three jaws, with a single jaw on one side of said needle recess and a pair of jaws on the opposite side of the needle recess.

36. The combination as claimed in claim 22 wherein said worksurface defines a planar worksurface that is coplanar with a plane defined by said needle feed wheel, said worksurface defining an arcuate edge which matches a circumference of the rotatable feed wheel and is positioned adjacent thereto.

37. The combination as claimed in claim 36, wherein said arcuate edge and circumference of the rotatable feed wheel define a gap therebetween that is less than a diameter of the needles to be singulated, so that the operator may slide needles from the worksurface to the needle feed wheel as the needles are singulated.

38. A method of semi-automatically singulating needles having attached sutures for subsequent packaging in a tray to form suture packages, said method comprising the steps of:
   (a) arranging a plurality of needles on a horizontal work surface while gathering the sutures into a bundle for tensioning;
   (b) singulating one of said needles and its suture and sliding the needle across said worksurface to a rotating needle feed wheel;
   (c) semi-automatically sliding and inserting the singulated needle with attached suture into a pocket formed on said rotating needle feed wheel, and advancing the needle feed wheel;
   (d) imparting axial tension to the suture to register the needle in said pocket;
   (e) automatically gripping, lifting said needle with a robotic handling device, and then indexing the robotic handling device to advance said needle from said pocket to a package tray.

39. A method as claimed in claim 38, which further includes the step of inserting a needle into a package tray with a first gripping member while simultaneously gripping a second needle in a needle pocket with a second gripping member.

40. A method as claimed in claim 39, wherein said sliding step is preformed partially on said worksurface, and partially on said needle feed wheel, said worksurface and said feed wheel being coplanar.

41. A method as claimed in claim 38 which includes the step of incrementally pausing and advancing the needle feed wheel for inserting and removing needles therefrom.

42. A method as claimed in claim 38 which includes the step of verifying a presence of a needle in a needle pocket before indexing the robotic handling device.

43. A method as claimed in claim 38 which includes the step of sequentially singulating a plurality of needles with attached sutures and sliding them one at a time into successive needle pockets on said rotating needle feed wheel as said wheel is rotated.

44. A method as claimed in claim 43, in which said sutures are sequentially tensioned by individual reciprocating members mounted on said needle wheel as said needle wheel is rotated, and said step of sequentially tensioning said sutures registers the needles for subsequent automatic robotic gripping.

45. A method as claimed in claim 44 which further includes the step of pulling the suture free of the bundle held in tension prior to insertion of the needle in the package tray.

* * * * *